(12) United States Patent
Battrell et al.

(10) Patent No.: US 10,436,713 B2
(45) Date of Patent: Oct. 8, 2019

(54) PORTABLE FLUORESCENCE DETECTION SYSTEM AND MICROASSAY CARTRIDGE

(71) Applicant: Micronics, Inc., Redmond, WA (US)

(72) Inventors: C. Frederick Battrell, Wenatchee, WA (US); Troy D. Daiber, Auburn, WA (US); William Samuel Hunter, Jan Juc (AU)

(73) Assignee: MICRONICS, INC., Redmond, WA (US)

( * ) Notice: Subject to any disclaimer, the term of this patent is extended or adjusted under 35 U.S.C. 154(b) by 0 days.

(21) Appl. No.: 15/804,869

(22) Filed: Nov. 6, 2017

(65) Prior Publication Data

US 2018/0292319 A1 Oct. 11, 2018

Related U.S. Application Data

(63) Continuation of application No. 14/653,726, filed as application No. PCT/US2013/077244 on Dec. 20, 2013, now abandoned.

(60) Provisional application No. 61/745,329, filed on Dec. 21, 2012.

(51) Int. Cl.
*G01N 21/64* (2006.01)
*B01L 3/00* (2006.01)
*B01L 7/00* (2006.01)

(52) U.S. Cl.
CPC .... *G01N 21/6428* (2013.01); *B01L 3/502715* (2013.01); *B01L 7/52* (2013.01); *G01N 21/645* (2013.01); *B01L 2200/0684* (2013.01); *B01L 2300/0816* (2013.01); *B01L 2300/168* (2013.01); *B01L 2300/1827* (2013.01); *B01L 2300/1844* (2013.01); *B01L 2400/0487* (2013.01); *G01N 2201/062* (2013.01); *G01N 2201/12* (2013.01); *Y02A 90/26* (2018.01)

(58) Field of Classification Search
CPC ...................... G01N 21/6428; B01L 3/502715
See application file for complete search history.

(56) References Cited

U.S. PATENT DOCUMENTS

| | | |
|---|---|---|
| 3,013,467 A | 12/1961 | Minsky |
| 3,799,742 A | 3/1974 | Coleman |
| 3,996,345 A | 12/1976 | Ullman et al. |
| 4,104,029 A | 8/1978 | Maier, Jr. |
| 4,235,960 A | 11/1980 | Sasse et al. |
| 4,304,257 A | 12/1981 | Webster |
| 4,366,241 A | 12/1982 | Tom et al. |
| 4,373,932 A | 2/1983 | Gribnau et al. |
| 4,610,678 A | 9/1986 | Weisman et al. |
| 4,683,195 A | 7/1987 | Mullis et al. |
| 4,683,202 A | 7/1987 | Mullis |
| 4,788,729 A | 12/1988 | Walker |
| 4,798,703 A | 1/1989 | Minekane |
| 4,800,159 A | 1/1989 | Mullis et al. |
| 4,810,630 A | 3/1989 | Craig et al. |
| 4,833,332 A | 5/1989 | Robertson, Jr. et al. |
| 4,837,168 A | 6/1989 | de Jaeger et al. |
| 4,848,722 A | 7/1989 | Webster |
| 4,855,240 A | 8/1989 | Rosenstein et al. |
| 4,869,282 A | 9/1989 | Sittler et al. |
| 4,883,750 A | 11/1989 | Whiteley et al. |
| 4,889,818 A | 12/1989 | Gelfand et al. |
| 4,943,522 A | 7/1990 | Eisinger et al. |
| 4,956,302 A | 9/1990 | Gordon et al. |
| 4,965,188 A | 10/1990 | Mullis et al. |
| 5,038,852 A | 8/1991 | Johnson et al. |
| 5,075,078 A | 12/1991 | Osikowicz et al. |
| 5,075,212 A | 12/1991 | Rotbart |
| 5,100,626 A | 3/1992 | Levin |
| 5,120,643 A | 6/1992 | Ching et al. |

(Continued)

FOREIGN PATENT DOCUMENTS

| | | |
|---|---|---|
| CN | 1146017 A | 3/1997 |
| CN | 1253625 A | 5/2000 |

(Continued)

OTHER PUBLICATIONS

Al Zahrani et al., "Accuracy and Utility of Commercially Available Amplification and Serologic Tests for the Diagnosis of Minimal Pulmonary Tuberculosis," *Am J Respir Crit Care Med* 162:1323-1329, 2000.

Aoki et al., "Serine Repeat Antigen (SERA5) Is Predominantly Expressed among the SERA Multigene Family of Plasmodium falciparum, and the Acquired Antibody Titers Correlate with Serum Inhibition of the Parasite Growth," *The Journal of Biological Chemistry* 277(49):47533-47540, Dec. 2002.

Arar et al., "Synthesis and Antiviral Activity of Peptide-Oligonucleotide Conjugates Prepared by Using $N_\alpha$-(Bromoacetyl)peptides," *Bioconjugate Chem.* 6(5):573-577, 1995.

Arikan et al., "Anti-Kp 90 IgA Antibodies in the Diagnosis of Active Tuberculosis," *CHEST* 114(5): 1253-1257, Nov. 1998.

(Continued)

*Primary Examiner* — Narayan K Bhat
(74) *Attorney, Agent, or Firm* — Seed IP Law Group LLP

(57) ABSTRACT

A compact, microprocessor-controlled instrument for fluorometric assays in liquid samples has a floating stage with docking bay for receiving a microfluidic cartridge and a scanning detector head with on-board embedded microprocessor controlled by an optical data acquisition and processing daemon within the detector head for controlling source LEDs, emission signal amplification and filtering in an isolated, low noise, high-gain environment within the detector head. Multiple optical channels may be incorporated in the scanning head. The assay ma be validated using dual channel optics for monitoring a first fluorophore associated with a target analyte and a second fluorophore associated with a control. Molecular biological assays use PCR amplification of target nucleic acids and fluorometric assays, which may require temperature control during detection. Sensitivity and resistance to bubble interference during scanning are improved using a heating block with reflective mirror face in contact with a thermo-optical window enclosing the liquid sample.

9 Claims, 36 Drawing Sheets

(56) References Cited

U.S. PATENT DOCUMENTS

| | | |
|---|---|---|
| 5,130,238 A | 7/1992 | Malek et al. |
| 5,141,850 A | 8/1992 | Cole et al. |
| 5,145,578 A | 9/1992 | Tokubo et al. |
| 5,160,701 A | 11/1992 | Brown, III et al. |
| 5,192,980 A | 3/1993 | Dixon et al. |
| 5,225,163 A | 7/1993 | Andrews |
| 5,234,809 A | 8/1993 | Boom et al. |
| 5,252,459 A | 10/1993 | Tarcha et al. |
| 5,270,183 A | 12/1993 | Corbett et al. |
| 5,275,785 A | 1/1994 | May et al. |
| 5,296,703 A | 3/1994 | Tsien |
| 5,304,487 A | 4/1994 | Wilding et al. |
| 5,354,668 A | 10/1994 | Auerbach |
| 5,415,994 A | 5/1995 | Imrich et al. |
| 5,420,016 A | 5/1995 | Boguslaski et al. |
| 5,427,930 A | 6/1995 | Birkenmeyer et al. |
| 5,443,890 A | 8/1995 | Öhman |
| 5,447,440 A | 9/1995 | Davis et al. |
| 5,455,166 A | 10/1995 | Walker |
| 5,486,335 A | 1/1996 | Wilding et al. |
| 5,498,392 A | 3/1996 | Wilding et al. |
| 5,504,013 A | 4/1996 | Senior |
| 5,543,026 A | 8/1996 | Hoff et al. |
| 5,578,818 A | 11/1996 | Kain et al. |
| 5,582,989 A | 12/1996 | Caskey et al. |
| 5,587,128 A | 12/1996 | Wilding et al. |
| 5,591,645 A | 1/1997 | Rosenstein |
| 5,593,824 A | 1/1997 | Treml et al. |
| 5,602,040 A | 2/1997 | May et al. |
| 5,622,871 A | 4/1997 | May et al. |
| 5,631,734 A | 5/1997 | Stern et al. |
| 5,635,358 A | 6/1997 | Wilding et al. |
| 5,635,602 A | 6/1997 | Cantor et al. |
| 5,639,428 A | 6/1997 | Cottingham |
| 5,656,503 A | 8/1997 | May et al. |
| 5,658,723 A | 8/1997 | Oberhardt |
| 5,660,370 A | 8/1997 | Webster |
| 5,660,990 A | 8/1997 | Rao et al. |
| 5,670,381 A | 9/1997 | Jou et al. |
| 5,707,516 A | 1/1998 | Tomizawa et al. |
| 5,707,807 A | 1/1998 | Kato |
| 5,716,842 A | 2/1998 | Baier et al. |
| 5,716,852 A | 2/1998 | Yager et al. |
| 5,718,567 A | 2/1998 | Rapp et al. |
| 5,724,404 A | 3/1998 | Garcia et al. |
| 5,726,026 A | 3/1998 | Wilding et al. |
| 5,726,404 A | 3/1998 | Brody |
| 5,726,751 A | 3/1998 | Altendorf et al. |
| 5,730,850 A | 3/1998 | Kambara et al. |
| 5,747,349 A | 5/1998 | van den Engh et al. |
| 5,748,827 A | 5/1998 | Holl et al. |
| 5,759,014 A | 6/1998 | Van Lintel |
| 5,770,460 A | 6/1998 | Pawlak et al. |
| 5,798,273 A | 8/1998 | Shuler et al. |
| 5,856,174 A | 1/1999 | Lipshutz et al. |
| 5,863,502 A | 1/1999 | Southgate et al. |
| 5,863,801 A | 1/1999 | Southgate et al. |
| 5,872,710 A | 2/1999 | Kameyama |
| 5,906,602 A | 5/1999 | Weber et al. |
| 5,922,210 A | 7/1999 | Brody et al. |
| 5,922,591 A | 7/1999 | Anderson et al. |
| 5,932,100 A | 8/1999 | Yager et al. |
| 5,932,799 A | 8/1999 | Moles |
| 5,948,684 A | 9/1999 | Weigl et al. |
| 5,955,029 A | 9/1999 | Wilding et al. |
| 5,965,410 A | 10/1999 | Chow et al. |
| 5,971,158 A | 10/1999 | Yager et al. |
| 5,971,355 A | 10/1999 | Biegelsen et al. |
| 5,972,710 A | 10/1999 | Weigl et al. |
| 5,972,721 A | 10/1999 | Bruno et al. |
| 5,974,867 A | 11/1999 | Forster et al. |
| 5,989,813 A | 11/1999 | Gerdes |
| 6,001,307 A | 12/1999 | Naka et al. |
| 6,007,309 A | 12/1999 | Hartley |
| 6,007,775 A | 12/1999 | Yager |
| 6,018,616 A | 1/2000 | Schaper |
| 6,020,187 A | 2/2000 | Tam |
| 6,037,168 A | 3/2000 | Brown |
| 6,057,167 A | 5/2000 | Shieh et al. |
| 6,068,752 A | 5/2000 | Dubrow et al. |
| 6,086,740 A | 7/2000 | Kennedy |
| 6,158,712 A | 12/2000 | Craig |
| 6,168,948 B1 | 1/2001 | Anderson et al. |
| 6,171,865 B1 | 1/2001 | Weigl et al. |
| 6,184,029 B1 | 2/2001 | Wilding et al. |
| 6,210,514 B1 | 4/2001 | Cheung et al. |
| 6,210,882 B1 | 4/2001 | Landers et al. |
| 6,272,939 B1 | 8/2001 | Frye et al. |
| 6,287,850 B1 | 9/2001 | Besemer et al. |
| 6,303,389 B1 | 10/2001 | Levin et al. |
| 6,309,875 B1 | 10/2001 | Gordon |
| 6,325,975 B1 | 12/2001 | Naka et al. |
| 6,326,211 B1 | 12/2001 | Anderson et al. |
| 6,368,876 B1 | 4/2002 | Huang et al. |
| 6,387,290 B1 | 5/2002 | Brody et al. |
| 6,390,791 B1 | 5/2002 | Maillefer et al. |
| 6,399,398 B1 | 6/2002 | Cunningham et al. |
| 6,418,968 B1 | 7/2002 | Pezzuto et al. |
| 6,431,212 B1 | 8/2002 | Hayenga et al. |
| 6,439,036 B1 | 8/2002 | Mansky |
| 6,468,807 B1 | 10/2002 | Svensson et al. |
| 6,472,161 B1 | 10/2002 | Baugh |
| 6,488,896 B2 | 12/2002 | Weigl et al. |
| 6,506,346 B1 | 1/2003 | Monro |
| 6,541,213 B1 | 4/2003 | Weigl et al. |
| 6,541,274 B2 | 4/2003 | Nagle et al. |
| 6,562,209 B1 | 5/2003 | Sullivan et al. |
| 6,569,674 B1 | 5/2003 | McGarry et al. |
| 6,576,459 B2 | 6/2003 | Miles et al. |
| 6,581,899 B2 | 6/2003 | Williams |
| 6,614,030 B2 | 9/2003 | Maher et al. |
| 6,620,273 B2 | 9/2003 | Dai et al. |
| 6,632,655 B1 | 10/2003 | Mehta et al. |
| 6,635,487 B1 | 10/2003 | Lee et al. |
| 6,637,463 B1 | 10/2003 | Lei et al. |
| 6,664,104 B2 | 12/2003 | Pourahmadi et al. |
| 6,720,411 B2 | 4/2004 | Mirkin et al. |
| 6,729,352 B2 | 5/2004 | O'Connor et al. |
| 6,731,178 B2 | 5/2004 | Gailhard et al. |
| 6,731,781 B1 | 5/2004 | Shams et al. |
| 6,743,399 B1 | 6/2004 | Weigl et al. |
| 6,748,975 B2 | 6/2004 | Hartshorne et al. |
| 6,758,107 B2 | 7/2004 | Cabuz |
| 6,767,194 B2 | 7/2004 | Jeon et al. |
| 6,787,338 B2 | 9/2004 | Wittwer et al. |
| 6,793,753 B2 | 9/2004 | Unger et al. |
| 6,815,160 B1 | 11/2004 | Chien et al. |
| 6,843,263 B2 | 1/2005 | Kuo et al. |
| 6,872,566 B2 | 3/2005 | Vischer et al. |
| 6,901,949 B2 | 6/2005 | Cox et al. |
| 6,916,113 B2 | 7/2005 | Van de Goor et al. |
| 6,951,632 B2 | 10/2005 | Unger et al. |
| 6,953,675 B2 | 10/2005 | Leung et al. |
| 6,953,676 B1 | 10/2005 | Wilding et al. |
| 6,955,738 B2 | 10/2005 | Derand et al. |
| 6,974,119 B2 | 12/2005 | Brendle et al. |
| 6,974,669 B2 | 12/2005 | Mirkin et al. |
| 7,010,391 B2 | 3/2006 | Handique et al. |
| 7,052,594 B2 | 5/2006 | Pelrine et al. |
| 7,087,414 B2 | 8/2006 | Gerdes et al. |
| 7,141,416 B2 | 11/2006 | Krutzik |
| 7,153,673 B2 | 12/2006 | Stern |
| 7,223,363 B2 | 5/2007 | McNeely et al. |
| 7,223,371 B2 | 5/2007 | Hayenga et al. |
| 7,226,562 B2 | 6/2007 | Holl et al. |
| 7,235,400 B2 | 6/2007 | Adey |
| 7,318,913 B2 | 1/2008 | Loeffler et al. |
| 7,416,892 B2 | 8/2008 | Battrell et al. |
| 7,445,926 B2 | 11/2008 | Mathies et al. |
| 7,514,212 B2 | 4/2009 | Prudent et al. |
| 7,517,651 B2 | 4/2009 | Marshall et al. |
| 7,541,147 B2 | 6/2009 | Marshall et al. |
| 7,544,506 B2 | 6/2009 | Breidford et al. |
| 7,607,641 B1 | 10/2009 | Yuan |

(56) References Cited

U.S. PATENT DOCUMENTS

| | | |
|---|---|---|
| 7,615,370 B2 | 11/2009 | Streit et al. |
| 7,648,835 B2 | 1/2010 | Breidford et al. |
| 7,695,683 B2 | 4/2010 | Quan et al. |
| 7,749,444 B2 | 7/2010 | Yamada et al. |
| 7,763,453 B2 | 7/2010 | Clemmens et al. |
| 7,785,776 B2 | 8/2010 | Wittwer et al. |
| 7,832,429 B2 | 11/2010 | Young et al. |
| 7,906,317 B2 | 3/2011 | Lee et al. |
| 7,955,836 B2 | 6/2011 | Clemmens et al. |
| 8,104,497 B2 | 1/2012 | Unger et al. |
| 8,104,514 B2 | 1/2012 | Fernandes et al. |
| 8,110,392 B2 | 2/2012 | Battrell et al. |
| 8,222,023 B2 | 7/2012 | Battrell et al. |
| 8,329,453 B2 | 12/2012 | Battrell et al. |
| 8,431,389 B2 | 4/2013 | Battrell et al. |
| 8,716,007 B2 | 5/2014 | Battrell et al. |
| 8,747,779 B2 | 6/2014 | Sprague et al. |
| 8,772,017 B2 | 7/2014 | Battrell et al. |
| 9,056,291 B2 | 6/2015 | Battrell et al. |
| 9,132,423 B2 | 9/2015 | Battrell et al. |
| 9,272,280 B2 | 3/2016 | Viola et al. |
| 9,895,692 B2 | 2/2018 | Battrell et al. |
| 10,065,186 B2 | 9/2018 | Kolb et al. |
| 10,087,440 B2 | 10/2018 | Lofquist et al. |
| 10,190,153 B2 | 1/2019 | Bouzek |
| 2001/0046701 A1 | 11/2001 | Schulte et al. |
| 2002/0081934 A1 | 6/2002 | Murao et al. |
| 2002/0086443 A1 | 7/2002 | Bamdad |
| 2002/0137196 A1 | 9/2002 | Miles et al. |
| 2002/0160518 A1 | 10/2002 | Hayenga et al. |
| 2002/0192676 A1 | 12/2002 | Madonna et al. |
| 2002/0195152 A1 | 12/2002 | Fernandes et al. |
| 2003/0008308 A1 | 1/2003 | Enzelberger et al. |
| 2003/0013184 A1 | 1/2003 | Streit et al. |
| 2003/0032028 A1 | 2/2003 | Dace et al. |
| 2003/0073229 A1 | 4/2003 | Greenstein et al. |
| 2003/0124619 A1 | 7/2003 | Weigl et al. |
| 2003/0129756 A1 | 7/2003 | Thorne et al. |
| 2003/0136178 A1 | 7/2003 | Cabuz |
| 2003/0152927 A1 | 8/2003 | Jakobsen et al. |
| 2003/0152994 A1 | 8/2003 | Woudenberg et al. |
| 2003/0153686 A1 | 8/2003 | Onoe et al. |
| 2003/0175990 A1 | 9/2003 | Hayenga et al. |
| 2003/0215818 A1 | 11/2003 | Lorenz |
| 2003/0215825 A1 | 11/2003 | Tong |
| 2003/0224434 A1 | 12/2003 | Wittwer et al. |
| 2004/0005718 A1 | 1/2004 | Fukushima |
| 2004/0018611 A1 | 1/2004 | Ward et al. |
| 2004/0024051 A1 | 2/2004 | Holton |
| 2004/0037739 A1 | 2/2004 | McNeely et al. |
| 2004/0081997 A1 | 4/2004 | Stern |
| 2004/0115094 A1 | 6/2004 | Gumbrecht et al. |
| 2004/0121364 A1 | 6/2004 | Chee et al. |
| 2004/0124384 A1 | 7/2004 | Biegelsen et al. |
| 2004/0189311 A1 | 9/2004 | Glezer et al. |
| 2004/0209354 A1 | 10/2004 | Mathies et al. |
| 2004/0224339 A1 | 11/2004 | Numajiri et al. |
| 2004/0226348 A1 | 11/2004 | Bruce, III et al. |
| 2004/0248167 A1 | 12/2004 | Quake et al. |
| 2005/0013732 A1 | 1/2005 | Battrell et al. |
| 2005/0019792 A1 | 1/2005 | McBride et al. |
| 2005/0019898 A1 | 1/2005 | Adey et al. |
| 2005/0037397 A1 | 2/2005 | Mirkin et al. |
| 2005/0106066 A1 | 5/2005 | Saltsman et al. |
| 2005/0106742 A1 | 5/2005 | Wahl et al. |
| 2005/0118570 A1 | 6/2005 | Hollis et al. |
| 2005/0129582 A1 | 6/2005 | Breidford et al. |
| 2005/0136552 A1 | 6/2005 | Buechler |
| 2005/0142582 A1 | 6/2005 | Doyle et al. |
| 2005/0157301 A1 | 7/2005 | Chediak et al. |
| 2005/0161669 A1 | 7/2005 | Jovanovich et al. |
| 2005/0164373 A1 | 7/2005 | Oldham et al. |
| 2005/0186585 A1 | 8/2005 | Juncosa et al. |
| 2005/0205816 A1 | 9/2005 | Hayenga et al. |
| 2005/0217741 A1 | 10/2005 | Bohm |
| 2005/0221281 A1 | 10/2005 | Ho |
| 2005/0284817 A1 | 12/2005 | Fernandez et al. |
| 2006/0003440 A1 | 1/2006 | Streit et al. |
| 2006/0073484 A1 | 4/2006 | Mathies et al. |
| 2006/0076068 A1 | 4/2006 | Young et al. |
| 2006/0127886 A1 | 6/2006 | Kaylor et al. |
| 2006/0166375 A1 | 7/2006 | Hawkins et al. |
| 2006/0178568 A1 | 8/2006 | Danna et al. |
| 2006/0246575 A1 | 11/2006 | Lancaster et al. |
| 2006/0254916 A1 | 11/2006 | Hernandez et al. |
| 2006/0263816 A1 | 11/2006 | Laikhter et al. |
| 2006/0264782 A1 | 11/2006 | Holmes et al. |
| 2006/0275852 A1 | 12/2006 | Montagu et al. |
| 2006/0275893 A1 | 12/2006 | Ishii et al. |
| 2006/0292588 A1 | 12/2006 | Chou et al. |
| 2006/0292630 A1 | 12/2006 | Fukumoto |
| 2007/0008536 A1 | 1/2007 | Mitani et al. |
| 2007/0009383 A1 | 1/2007 | Bedingham et al. |
| 2007/0014695 A1 | 1/2007 | Yue et al. |
| 2007/0042427 A1 | 2/2007 | Gerdes et al. |
| 2007/0125947 A1 | 6/2007 | Sprinzak et al. |
| 2007/0154895 A1 | 7/2007 | Spaid et al. |
| 2007/0183935 A1 | 8/2007 | Clemmens et al. |
| 2007/0190525 A1 | 8/2007 | Gu et al. |
| 2007/0219366 A1 | 9/2007 | Gumbrecht et al. |
| 2007/0234785 A1 | 10/2007 | Beerling et al. |
| 2007/0243603 A1 | 10/2007 | Einsle et al. |
| 2007/0280856 A1 | 12/2007 | Ulmanella et al. |
| 2007/0292858 A1 | 12/2007 | Chen et al. |
| 2008/0050283 A1 | 2/2008 | Chou et al. |
| 2008/0081341 A1 | 4/2008 | Maher et al. |
| 2008/0124749 A1 | 5/2008 | Farnam et al. |
| 2008/0226500 A1 | 9/2008 | Shikida et al. |
| 2008/0260586 A1 | 10/2008 | Boamfa |
| 2008/0274511 A1 | 11/2008 | Tan et al. |
| 2008/0297792 A1 | 12/2008 | Kim et al. |
| 2009/0000678 A1 | 1/2009 | Therriault et al. |
| 2009/0017483 A1 | 1/2009 | Yamaoka et al. |
| 2009/0047713 A1 | 2/2009 | Handique |
| 2009/0061450 A1 | 3/2009 | Hunter |
| 2009/0111159 A1 | 4/2009 | Brolaski et al. |
| 2009/0148847 A1 | 6/2009 | Kokoris et al. |
| 2009/0148933 A1 | 7/2009 | Battrell et al. |
| 2009/0181411 A1 | 7/2009 | Battrell et al. |
| 2009/0298059 A1 | 12/2009 | Gumbrecht et al. |
| 2009/0325203 A1 | 12/2009 | Jenny et al. |
| 2009/0325276 A1 | 12/2009 | Battrell et al. |
| 2010/0041049 A1 | 2/2010 | Smith et al. |
| 2010/0112723 A1 | 5/2010 | Battrell et al. |
| 2010/0120129 A1 | 5/2010 | Amshey et al. |
| 2010/0291588 A1 | 11/2010 | McDevitt et al. |
| 2010/0303687 A1 | 12/2010 | Blaga et al. |
| 2011/0151479 A1 | 6/2011 | Stevens et al. |
| 2011/0207621 A1 | 8/2011 | Montagu et al. |
| 2012/0028342 A1 | 2/2012 | Ismagilov et al. |
| 2012/0064597 A1 | 3/2012 | Clemmens et al. |
| 2012/0071342 A1 | 3/2012 | Lochhead et al. |
| 2012/0115214 A1 | 5/2012 | Battrell et al. |
| 2012/0135511 A1 | 5/2012 | Battrell et al. |
| 2012/0156750 A1 | 6/2012 | Battrell et al. |
| 2012/0164383 A1 | 6/2012 | Sollmann |
| 2012/0164627 A1 | 6/2012 | Battrell et al. |
| 2012/0177543 A1 | 7/2012 | Battrell et al. |
| 2012/0329142 A1 | 12/2012 | Battrell et al. |
| 2013/0011912 A1 | 1/2013 | Battrell et al. |
| 2013/0017552 A1 | 1/2013 | Rudorfer |
| 2013/0032235 A1 | 2/2013 | Johnstone et al. |
| 2013/0115607 A1 | 5/2013 | Nielsen et al. |
| 2013/0130262 A1 | 5/2013 | Battrell et al. |
| 2014/0349381 A1 | 11/2014 | Battrell et al. |
| 2015/0158026 A1 | 6/2015 | Battrell et al. |
| 2015/0321193 A1 | 11/2015 | Sprague et al. |
| 2015/0346097 A1 | 12/2015 | Battrell et al. |
| 2015/0352549 A1 | 12/2015 | Kolb et al. |
| 2016/0090588 A1 | 3/2016 | Lofquist et al. |
| 2016/0102340 A1 | 4/2016 | Bouzek |

(56) References Cited

U.S. PATENT DOCUMENTS

| | | | |
|---|---|---|---|
| 2016/0193603 A1 | 7/2016 | Battrell et al. | |
| 2017/0113221 A1 | 4/2017 | Hoffman et al. | |

FOREIGN PATENT DOCUMENTS

| | | |
|---|---|---|
| CN | 102203605 A | 9/2011 |
| CN | 102602087 A | 7/2012 |
| DE | 20 2004 012 163 U1 | 11/2004 |
| EP | 0 320 308 A2 | 6/1989 |
| EP | 0 329 822 A2 | 8/1989 |
| EP | 0 399 859 A1 | 11/1990 |
| EP | 0 517 631 A1 | 12/1992 |
| EP | 1 180 135 B1 | 8/2005 |
| EP | 1 659 405 A1 | 5/2006 |
| EP | 1 707 965 A1 | 10/2006 |
| EP | 1 726 940 A1 | 11/2006 |
| EP | 1 792 654 A2 | 6/2007 |
| EP | 2 202 328 A1 | 6/2010 |
| GB | 2 202 328 A | 9/1988 |
| JP | 52-55679 A | 5/1977 |
| JP | 61-137066 A | 6/1986 |
| JP | 7-151101 A | 6/1995 |
| JP | 2520468 Y2 | 12/1996 |
| JP | 10-82773 A | 3/1998 |
| JP | 10-504916 A | 5/1998 |
| JP | 11-508347 A | 7/1999 |
| JP | 2000-314719 A | 11/2000 |
| JP | 2003-166910 A | 6/2003 |
| JP | 2003-207454 A | 7/2003 |
| JP | 2004-028589 A | 1/2004 |
| JP | 2004-333452 A | 11/2004 |
| JP | 2005-512071 A | 4/2005 |
| JP | 2005-527303 A | 9/2005 |
| JP | 2005-531006 A | 10/2005 |
| JP | 2005-345378 A | 12/2005 |
| JP | 2006-73371 A | 3/2006 |
| JP | 2006-84459 A | 3/2006 |
| JP | 2006-90774 A | 4/2006 |
| JP | 2006-512092 A | 4/2006 |
| JP | 2006-122743 A | 5/2006 |
| JP | 2006-517029 A | 7/2006 |
| JP | 2006-227301 A | 8/2006 |
| JP | 2006-246777 A | 9/2006 |
| JP | 2006-520190 A | 9/2006 |
| JP | 2007-514142 A | 5/2007 |
| JP | 2007-532918 A | 11/2007 |
| JP | 2008-503722 A | 2/2008 |
| JP | 2008-89597 A | 4/2008 |
| JP | 2008-96375 A | 4/2008 |
| JP | 2008-537063 A | 9/2008 |
| JP | 2009-14529 A | 1/2009 |
| JP | 2009-019962 A | 1/2009 |
| JP | 2009-510337 A | 3/2009 |
| JP | 2009-513966 A | 4/2009 |
| JP | 2009-539883 A | 8/2009 |
| JP | 2009-255083 A | 11/2009 |
| JP | 2010-78508 A | 4/2010 |
| JP | 2010-519463 A | 6/2010 |
| JP | 2010-535346 A | 11/2010 |
| JP | 2010-516455 A | 7/2012 |
| JP | 2013-518289 A | 5/2013 |
| JP | 2015-510111 A | 4/2015 |
| JP | 2016-508197 A | 3/2016 |
| WO | 86/06488 A1 | 11/1986 |
| WO | 88/08534 A1 | 11/1988 |
| WO | 88/10315 A1 | 12/1988 |
| WO | 89/06700 A1 | 7/1989 |
| WO | 89/09284 A1 | 10/1989 |
| WO | 91/12336 A1 | 8/1991 |
| WO | 96/33399 A1 | 10/1996 |
| WO | 97/01055 A1 | 1/1997 |
| WO | 98/49543 A1 | 11/1998 |
| WO | 00/63670 A1 | 10/2000 |
| WO | 01/70381 A2 | 9/2001 |
| WO | 02/01184 A1 | 1/2002 |
| WO | 02/12896 A1 | 2/2002 |
| WO | 02/41994 A2 | 5/2002 |
| WO | 02/072262 A1 | 9/2002 |
| WO | 02/081934 A2 | 10/2002 |
| WO | 03/015923 A1 | 2/2003 |
| WO | 03/031997 A2 | 4/2003 |
| WO | 03/049860 A1 | 6/2003 |
| WO | 03/054523 A2 | 7/2003 |
| WO | 03/097831 A1 | 11/2003 |
| WO | 03/099355 A2 | 12/2003 |
| WO | 03/101887 A2 | 12/2003 |
| WO | 03/102546 A2 | 12/2003 |
| WO | 2004/055198 A2 | 7/2004 |
| WO | 2004/061085 A2 | 7/2004 |
| WO | 2004/065010 A2 | 8/2004 |
| WO | 2004/065930 A2 | 8/2004 |
| WO | 2005/016529 A1 | 2/2005 |
| WO | 2005/022154 A1 | 3/2005 |
| WO | 2005/066638 A1 | 7/2005 |
| WO | 2005/069015 A1 | 7/2005 |
| WO | 2005/088280 A1 | 9/2005 |
| WO | 2005/102682 A2 | 11/2005 |
| WO | 2005/106024 A2 | 11/2005 |
| WO | 2005/118849 A1 | 12/2005 |
| WO | 2006/018811 A1 | 2/2006 |
| WO | 2006/035830 A1 | 4/2006 |
| WO | 2006/052652 A2 | 5/2006 |
| WO | 2006/076567 A2 | 7/2006 |
| WO | 2006/083833 A2 | 8/2006 |
| WO | 2006/125767 A1 | 11/2006 |
| WO | 2007/049009 A1 | 5/2007 |
| WO | 2007/064635 A1 | 6/2007 |
| WO | 2007/106579 A2 | 9/2007 |
| WO | 2007/106580 A2 | 9/2007 |
| WO | 2007/109584 A1 | 9/2007 |
| WO | 2007/137291 A1 | 11/2007 |
| WO | 2008/002462 A2 | 1/2008 |
| WO | 2008/036544 A1 | 3/2008 |
| WO | 2008/070198 A2 | 6/2008 |
| WO | 2008/101732 A1 | 8/2008 |
| WO | 2008/147382 A1 | 12/2008 |
| WO | 2009/018473 A1 | 2/2009 |
| WO | 2009/037361 A1 | 3/2009 |
| WO | 2009/105711 A1 | 8/2009 |
| WO | 2010/025302 A2 | 3/2010 |
| WO | 2010/088514 A1 | 8/2010 |
| WO | 2011/094577 A2 | 8/2011 |
| WO | 2012/071069 A1 | 5/2012 |
| WO | 2013/010674 A1 | 1/2013 |
| WO | 2013/052318 A1 | 4/2013 |
| WO | 2014/100732 A1 | 6/2014 |
| WO | 2014/182831 A1 | 11/2014 |
| WO | 2014/182847 A1 | 11/2014 |

OTHER PUBLICATIONS

Birkelund, "The molecular biology and diagnostics of Chlamydia trachomatis," *Danish Medical Bulletin* 39(4):304-320, Aug. 1992.

Bongartz et al., "Improved biological activity of antisense oligonucleotides conjugated to a fusogenic peptide," *Nucleic Acids Research* 22(22):4681-4688, 1994.

Bowden et al., "Using Self-Administered Tampons to Diagnose STDs," *AIDS Patient Care and STDs* 12(1):29-32, 1998.

Cady, "Quantum dot Molecular Beacons for DNA Detection," in *Micro and Nano Technologies in Bioanalysis*, Lee et al., (eds.), Humana Press, 2009, pp. 367-379.

Cai et al., "Interactions of DNA with Clay Minerals and Soil Colloidal Particles and Protection against Degradation by DNase," *Environ. Sci. Technol.* 40:2971-2976, 2006.

Carmona et al., "The use of fluorescence resonance energy transfer (FRET) peptides for measurement of clinically important proteolytic enzymes," *An Acad Bras Cienc* 81(3):381-392.

Chan et al., "Polymer surface modification by plasmas and photons," *Surface Science Reports* 24:1-54, 1996.

Chernesky et al., "Clinical Evaluation of the Sensitivity and Specificity of a Commercially Available Enzyme Immunoassay for

(56) References Cited

OTHER PUBLICATIONS

Detection of Rubella Virus-Specific Immunoglobulin M," *J. Clin. Microbiol.* 20(3):400-404, Sep. 1984.

Chernesky et al., "Detection of Chlamydia trachomatis Antigens by Enzyme Immunoassay and Immunofluorescence in Genital Specimens from Symptomatic and Asymptomatic Men and Women," *The Journal of Infectious Diseases* 154(1):141-148, Jul. 1986.

Chou et al., "Prevention of pre-PCR mis-priming and primer dimerization improves low-copy-number amplifications," *Nucleic Acids Research* 20(7):1717-1723, 1992.

Cissell et al., "Resonance energy transfer methods of RNA detection," *Analytical and Bioanalytical Chemistry* 393(1):125-135, 2009.

Crotchfelt et al., "Detection of Neisseria gonorrhoeae and Chlamydia trachomatis in Genitourinary Specimens from Men and Women by a Coamplification PCR Assay," *J. Clin. Microbiol.* 35(6):1536-1540, Jun. 1997.

Cuzzubbo et al., "Use of Recombinant Envelope Proteins for Serological Diagnosis of Dengue Virus Infection in an Immunochromatographic Assay," *Clin. Diagn. Lab. Immunol.* 8(6):1150-1155, 2001.

D'Aquila et al., "Maximizing sensitivity and specificity of PCR by pre-amplification heating," *Nucleic Acids Research* 19(13):3749, 1991.

Dean et al., "Comprehensive human genome amplification using multiple displacement amplification," *PNAS* 99(8):5261-5266, Apr. 2002.

Detter et al., "Isothermal Strand-Displacement Amplification Applications for High-Throughput Genomics," *Genomics* 80(6):691-698, Dec. 2002.

Edelstein et al., "The BARC biosensor applied to the detection of biological warfare agents," *Biosensors & Bioelectronics* 14:805-813, 2000.

Egger et al., "Reverse Transcription Multiplex PCR for Differentiation between Polio- and Enteroviruses from Clinical and Environmental Samples," *Journal of Clinical Microbiology* 33(6):1442-1447, Jun. 1995.

Eritja et al., "Synthesis of Defined Peptide-Oligonucleotide Hybrids Containing a Nuclear Transport Signal Sequence," *Tetrahedron* 47(24):4113-4120, 1991.

Fontana et al., "Performance of Strand Displacement Amplification Assay in the Detection of Chlamydia trachomatis and Neisseria gonorrhoeae," *Jpn. J. Infect. Dis.* 58:283-288, 2005.

Frame et al., "Identification and Typing of Herpes Simplex Virus by Enzyme Immunoassay with Monoclonal Antibodies," *J. Clin. Microbiol.* 20(2):162-166, Aug. 1984.

Franchi et al., "Cations as Mediators of the Adsorption of Nucleic Acids on Clay Surfaces in Prebiotic Environments," *Origins of Life and Evolution of the Biosphere* 33:1-16, Feb. 2003.

Freund et al., (eds.), "Film buckling, bulging, and peeling," in *Thin Film Materials: Stress, Defect Formation and Surface Evolution*, Cambridge, UK, The University of Cambridge, 2003, pp. 312-386.

Frohman, "Race: Rapid Amplification of cDNA Ends," in *PCR Protocols: A Guide to Methods and Applications*, Innis et al., (eds.), New York, Academic Press, Inc., 1990, pp. 28-38.

Gallo et al., "Study of viral integration of HPV-16 in young patients with LSIL," *J Clin Pathol* 56:532-536, 2003.

Garbassi et al., *Polymer Surfaces-From Physics to Technology*, John Wiley and Sons, Baltimore, Md., 1998, pp. 223-240. (20 pages).

Genovese et al., "Virus Variability and Its Impact on HIV and Hepatitis Therapy," *Advances in Virology* 2012:1-3, Dec. 2012.

Ghai et al., "Identification, expression, and functional characterization of MAEBL, a sporozoite and asexual blood stage chimeric erythrocyte-binding protein of Plasmodium falciparum," *Molecular & Biochemical Parasitology* 123:35-45, 2002.

Gijs, "Magnetic bead handling on-chip: new opportunities for analytical applications," *Microfluid Nanofluid* 1:22-40, 2004.

Gomes et al., "Immunoreactivity and differential developmental expression of known and putative Chlamydia trachomatis membrane proteins for biologically variant serovars representing distinct disease groups," *Microbes and Infection* 7:410-420, 2005.

Graham et al., "Magnetoresistive-based biosensors and biochips," *Trends in Biotechnology* 22(9):455-462, Sep. 2004.

Graves et al., "Development of Antibody to Measles Virus Polypeptides During Complicated and Uncomplicated Measles Virus Infections," *Journal of Virology* 49(2):409-412, Feb. 1984.

Grover et al., "Monolithic membrane valves and diaphragm pumps for practical large-scale integration into glass microfluidic devices," *Sensors and Actuators B* 89:315-323, 2003.

Hardt et al., "Passive micromixers for applications in the microreactor and mTAS fields," *Microfluid Nanofluid* 1:108-118, 2005.

Harris et al., "Typing of Dengue Viruses in Clinical Specimens and Mosquitoes by Single-Tube Multiplex Reverse Transcriptase PCR," *J. Clin. Microbiol.* 36(9):2634-2639, Sep. 1998.

Harrison et al., "Synthesis and hybridization analysis of a small library of peptide—oligonucleotide conjugates," *Nucleic Acids Research* 26(13):3136-3145, 1998.

Huft et al., "Fabrication of High-Quality Microfluidic Solid-Phase Chromatography Columns," *Anal. Chem.* 85:1797-1802, 2013.

Hummel et al., "Development of quantitative gene-specific real-time RT-PCR assays for the detection of measles virus in clinical specimens," *Journal of Virological Methods* 132:166-173, 2006.

Hung et al., "A specificity enhancer for polymerase chain reaction," *Nucleic Acids Research* 18(16):4953, Jun. 1990.

Innis et al., (eds.), *PCR Protocols: A Guide to Methods and Applications*, Academic Press, Inc., San Diego, California, 1990, 480 pages.

Jacobs et al., "Detection of Streptococcus pneumoniae Antigen in Bronchoalveolar Lavage Fluid Samples by a Rapid Immunochromatographic Membrane Assay," *J. Clin. Microbiol.* 43(8):4037-4040, 2005.

Joung et al., "Micropumps Based on Alternating High-Gradient Magnetic Fields," *IEEE Transactions on Magnetics* 36(4):2012-2014, Jul. 2000.

Kanehisa, "Use of statistical criteria for screening potential homologies in nucleic acid sequences," *Nucleic Acids Research* 12(1):203-213, Jan. 1984.

Kellogg et al., "TaqStart Antibody: "Hot Start" PCR Facilitated by a Neutralizing Monoclonal Antibody Directed Against Taq DNA Polymerase," *BioTechniques* 16(6):1134-1137, Jun. 1994.

Kennedy et al., "Protein-Protein Coupling Reactions and the Applications of Protein Conjugates," *Clinica Chimica Acta* 70(1):1-31, Jul. 1976.

Khan et al., "Antibiotic Resistance, Virulence Gene, and Molecular Profiles of Shiga Toxin-Producing *Escherichia coli* Isolates from Diverse Sources in Calcutta, India," *J. Clin. Microbiol.* 40(6):2009-2015, Jun. 2002.

Khan et al., "Prevalence and Genetic Profiling of Virulence Determinants of Non-O157 Shiga Toxin-Producing *Escherichia coli* Isolated from Cattle, Beef, and Humans, Calcutta, India," *Emerging Infectious Diseases* 8(1):54-62, Jan. 2002.

Khanna et al., "Transformation of *Bacillus subtilis* by DNA Bound on Montmorillonite and Effect of DNase on the Transforming Ability of Bound DNA," *Applied and Environmental Microbiology* 58(6):1930-1939, Jun. 1992.

Kittigul et al., "Use of a Rapid Immunochromatographic Test for Early Diagnosis of Dengue Virus Infection," *Eur. J. Clin. Microbiol. Infect. Dis.* 21(3):224-226, Mar. 2002.

Knox et al., "Evaluation of Self-Collected Samples in Contrast to Practitioner-Collected Samples for Detection of Chlamydia trachomatis, Neisseria gonorrhoeae, and Trichomonas vaginalis by Polymerase Chain Reaction Among Women Living in Remote Areas," *Sexually Transmitted Diseases* 29(11):647-654, Nov. 2002.

Krasnoperov et al., "Luminescent Probes for Ultrasensitive Detection of Nucleic Acids," *Bioconjug. Chem.* 21(2):319-327, Feb. 2010.

Kremer et al., "Measles Virus Genotyping by Nucleotide-Specific Multiplex PCR," *J. Clin. Microbiol.* 42(7):3017-3022, Jul. 2004.

Kuipers et al., "Detection of Chlamydia trachomatis in peripheral blood leukocytes of reactive arthritis patients by polymerase chain reaction," *Arthritis & Rheumatism* 41(10):1894-1895, Oct. 1998.

Kuipers et al., "Sensitivities of PCR, MicroTrak, ChlamydiaEIA, IDEIA, and PACE 2 for Purified Chlamydia trachomatis Elementary

(56) References Cited

OTHER PUBLICATIONS

Bodies in Urine, Peripheral Blood, Peripheral Blood Leukocytes, and Synovial Fluid," *J. Clin. Microbiol.* 33(12):3186-3190, Dec. 1995.

Kuno, "Universal diagnostic RT-PCR protocol for arboviruses," *Journal of Virological Methods* 72:27-41, 1998.

Kwoh et al., "Transcription-based amplification system and detection of amplified human immunodeficiency virus type 1 with a bead-based sandwich hybridization format," *Proc. Natl. Acad. Sci. U.S.A.* 86:1173-1177, Feb. 1989.

Lage et al., "Whole Genome Analysis of Genetic Alterations in Small DNA Samples Using Hyperbranched Strand Displacement Amplification and Array-CGH," *Genome Research* 13:294-307, 2003.

Lanciotti et al., "Rapid Detection and Typing of Dengue Viruses from Clinical Samples by Using Reverse Transcriptase-Polymerase Chain Reaction," *J. Clin. Microbiol.* 30(3):545-551, Mar. 1992.

Leclerc et al., "Meager genetic variability of the human malaria agent Plasmodium vivax," *PNAS* 101(40):14455-14460, Oct. 5, 2004.

Lee et al., "Implementation of Force Differentiation in the Immunoassay," *Analytical Biochemistry* 287:261-271, 2000.

Leung et al., "Rapid antigen detection testing in diagnosing group A b-hemolytic streptococcal pharyngitis," *Expert. Rev. Mol. Diagn.* 6(5):761-766, 2006.

Li et al., "Molecular Beacons: an optimal multifunctional biological probe," *Biochemical and Biophysical Research Communications* 373:457-461, 2008.

Lindegren et al., "Optimized Diagnosis of Acute Dengue Fever in Swedish Travelers by a Combination of Reverse Transcription-PCR and Immunoglobulin M Detection," *J. Clin. Microbiol.* 43(6):2850-2855, Jun. 2005.

Ling et al., "The Plasmodium falciparum clag9 gene encodes a rhoptry protein that is transferred to the host erythrocyte upon invasion," *Molecular Microbiology* 52(1):107-118, 2004.

Lundquist et al., "Human Recombinant Antibodies against Plasmodium falciparum Merozoite Surface Protein 3 Cloned from Peripheral Blood Leukocytes of Individuals with Immunity to Malaria Demonstrate Antiparasitic Properties," *Infect. Immun.* 74(6):3222-3231, Jun. 2006.

Luxton et al., "Use of External Magnetic Fields to Reduce Reaction Times in an Immunoassay Using Micrometer-Sized Paramagnetic Particles as Labels (Magnetoimmunoassay)," *Anal. Chem.* 76(6):1715-1719, Mar. 2004.

Mahony et al., "Chlamydia trachomatis confirmatory testing of PCR-positive genitourinary specimens using a second set of plasmid primers," *Molecular and Cellular Probes* 6:381-388, 1992.

Mahony et al., "Comparison of Plasmid- and Chromosome-Based Polymerase Chain Reaction Assays for Detecting Chlamydia trachomatis Nucleic Acids," *J. Clin. Microbiol.* 31(7):1753-1758, Jul. 1993.

Mahony et al., "Detection of Antichlamydial Immunoglobulin G and M Antibodies by Enzyme-Linked Immunosorbent Assay," *J. Clin. Microbiol.* 18(2):270-275, Aug. 1983.

Mahony et al., "Multiplex PCR for Detection of Chlamydia trachomatis and Neisseria gonorrhoeae in Genitourinary Specimens," *J. Clin. Microbiol.* 33(11):3049-3053, Nov. 1995.

Mahony, "Multiplex Polymerase Chain Reaction for the Diagnosis of Sexually Transmitted Diseases," *Clinics in Laboratory Medicine* 16(1):61-71, Mar. 1996.

Mayta et al., "Use of a reliable PCR assay for the detection of Neisseria gonorrhoeae in Peruvian patients," *Clinical Microbiology and Infection* 12(8):809-812, Aug. 2006.

Michon et al., "Naturally Acquired and Vaccine-Elicited Antibodies Block Erythrocyte Cytoadherence of the Plasmodium vivax Duffy Binding Protein," *Infect. Immun.* 68(6):3164-3171, Jun. 2000.

Migot-Nabias et al., "Immune Responses Against Plasmodium Falciparum Asexual Blood-Stage Antigens and Disease Susceptibility in Gabonese and Cameroonian Children," *Am. J. Trop. Med. Hyg.* 61(3):488-494, 1999.

Mitrani-Rosenbaum et al., "Simultaneous detection of three common sexually transmitted agents by polymerase chain reaction," *Am J Obstet Gynecol* 171(3):784-790, Sep. 1994.

Mohmmed et al., "Identification of karyopherin b as an immunogenic antigen of the malaria parasite using immune mice and human sera," *Parasite Immunology* 27:197-203, 2005.

Monis et al., "Nucleic acid amplification-based techniques for pathogen detection and identification," *Infection, Genetics and Evolution* 6:2-12, 2006.

Morré et al., "RNA Amplification by Nucleic Acid Sequence-Based Amplification with an Internal Standard Enables Reliable Detection of Chlamydia trachomatis in Cervical Scrapings and Urine Samples," *J. Clin. Microbiol.* 34(12):3108-3114, Dec. 1996.

Narum et al., "A novel Plasmodium falciparum erythrocyte binding protein-2 (EBP2/BAEBL) involved in erythrocyte receptor binding," *Molecular & Biochemical Parasitology* 119:159-168, 2002.

NCBI Database, GenBank Accession No. ACOL01000910, Jun. 9, 2009.

NCBI Database, GenBank Accession No. ACOL01004315, Jun. 9, 2009.

NCBI Database, GenBank Accession No. ACOL01004318, Jun. 9, 2009.

NCBI Database, GenBank Accession No. ACOL01004329, Jun. 9, 2009.

NCBI Database, GenBank Accession No. ACOL01004331, Jun. 9, 2009.

NCBI Database, GenBank Accession No. NP_473155, Jan. 3, 2007.

Nielsen et al., "Detection of Immunoglobulin G Antibodies to Cytomegalovirus Antigens by Antibody Capture Enzyme-Linked Immunosorbent Assay," *J. Clin. Microbiol.* 24(6):998-1003, Dec. 1986.

Notomi et al., "Loop-mediated isothermal amplification of DNA," *Nucleic Acids Research* 28(12):2-7, 2000.

Oeuvray et al., "Merozoite Surface Protein-3: A Malaria Protein Inducing Antibodies that Promote Plasmodium falciparum Killing by Cooperation With Blood Monocytes," *Blood* 84(5):1594-1602, Sep. 1994.

Ohara et al., "One-sided polymerase chain reaction: The amplification of cDNA," *Proc. Natl. Acad. Sci. U.S.A.* 86:5673-5677, Aug. 1989.

Ohta et al., "Enzyme-Linked Immunosorbent Assay of Influenza Specific IgA Antibody in Nasal Mucus," *Acta Paediatr. Jpn.* 33(5):617-622, Oct. 1991.

Østergaard et al., "A novel approach to the automation of clinical chemistry by controlled manipulation of magnetic particles," *Journal of Magnetism and Magnetic Materials* 194:156-162, 1999.

Ozoemena et al., "Comparative Evaluation of Measles Virus Specific TaqMan PCR and Conventional PCR Using Synthetic and Natural RNA Templates," *Journal of Medical Virology* 73:79-84, 2004.

Park et al., "Polymorphisms of p53, p21 and IRF-1 and cervical cancer susceptibility in Korean women," *Proceedings of the American Association of Cancer Research* 44, Second Edition, p. 1081, Jul. 2003.

Pfyffer et al., "Diagnostic Performance of Amplified *Mycobacterium tuberculosis* Direct Test with Cerebrospinal Fluid, Other Nonrespiratory, and Respiratory Specimens," *Journal of Clinical Microbiology* 34(4):834-841, Apr. 1996.

Pinder et al., "Immunoglobulin G Antibodies to Merozoite Surface Antigens Are Associated with Recovery from Choroquine-Resistant Plasmodium falciparum in Gambian Children," *Infect. Immun.* 74(5):2887-2893, May 2006.

Pingle et al., "Multiplexed Identification of Blood-Borne Bacterial Pathogens by Use of a Novel 16S rRNA Gene PCR-Ligase Detection Reaction-Capillary Electrophoresis Assay," *J. Clin. Microbiol.* 45(6):1927-1935, Jun. 2007.

Polley et al., "Vaccination for vivax malaria: targeting the invaders," *TRENDS in Parasitology* 20(3):99-102, Mar. 2004.

Porstmann et al., "Comparison of Chromogens for the Determination of Horseradish Peroxidase as a Marker in Enzyme Immunoassay," *J. Clin. Chem. Clin. Biochem.* 19(7):435-439, 1981.

(56) References Cited

OTHER PUBLICATIONS

Ramchandran et al., "Dry-reagent storage for disposable lab-on-acard diagnosis of enteric pathogens" Proceedings of the 1st Deistributed Diagnosis and Home Healthcare (D2H2) Conference, Arlington, Virginia, Apr. 2-4, 2006.
Ranjan et al., "Mapping regions containing binding residues within functional domains of Plasmodium vivax and Plasmodium knowlesi erythrocyte-binding proteins," *PNAS* 96(24):14067-14072, Nov. 1999.
Rida et al., "Long-range transport of magnetic microbeads using simple planar coils placed in a uniform magnetostatic field," *Applied Physics Letters* 83(12):2396-2398, Sep. 2003.
Roosendaal et al., "Comparison of different primer sets for detection of Chlamydia trachomatis by the polymerase chain reaction," *J. Med. Microbiol.* 38:426-433, 1993.
Schachter et al., "Ligase Chain Reaction to Detect Chlamydia trachomatis Infection of the Cervix," *J. Clin. Microbiol.* 32(10):2540-2543, Oct. 1994.
Shi et al., "Fabrication and optimization of the multiplex PCR-based oligonucleotide microarray for detection of Neisseria gonorrhoeae, Chlamydia trachomatis and Ureaplasma urealyticum," *Journal of Microbiological Methods* 62:245-256, 2005.
Shi et al., "Natural Immune Response to the C-Terminal 19-Kilodalton Domain of Plasmodium falciparum Merozoite Surface Protein 1," *Infect. Immun.* 64(7):2716-2723, Jul. 1996.
Shu et al., "Development of Group- and Serotype-Specific One-Step SYBR Green I-Based Real-Time Reverse Transcription-PCR Assay for Dengue Virus," *J. Clin. Microbiol.* 41(6):2408-2416, Jun. 2003.
Snounou et al., "High sensitivity of detection of human malaria parasites by the use of nested polymerase chain reaction," *Molecular and Biochemical Parasitology* 61:315-320, 1993.
Soukchareun et al., "Use of Na-Fmoc-cysteine(S-thiobutyl) Derivatized Oligodeoxynucleotides for the Preparation of Oligodeoxynucleotide—Peptide Hybrid Molecules," *Bioconjugate Chem.* 9:466-475, 1998.
Staben et al., "Particle transport in Poiseuille flow in narrow channels," *International Journal of Multiphase Flow* 31:529-547, 2005.
Stetsenko et al., "Efficient Conjugation of Peptides to Oligonucleotides by 'Native Ligation'," *J. Org. Chem.* 65:4900-4908, 2000.
Sturm et al., "Vaginal tampons as specimen collection device for the molecular diagnosis of non-ulcerative sexually transmitted infections in antenatal clinic attendees," *International Journal of STD & AIDS* 15:94-98, Feb. 2004.
Tai et al., "Artificial Receptors in Serologic Tests for the Early Diagnosis of Dengue Virus Infection," *Clinical Chemistry* 52(8):1486-1491, 2006.
Tamim et al., "Cervicovaginal coinfections with human papillomavirus and chlamydia trachomatis," *Diagnostic Microbiology and Infectious Disease* 43:277-281, 2002.
TechNote 303, "Lateral Flow Tests," Bangs Laboratories, Inc., Rev. #002, Apr. 11, 2008, pp. 1-7.
Tongren et al., "Target Antigen, Age, and Duration of Antigen Exposure Independently Regulate Immunoglobulin G Subclass Switching in Malaria," *Infect. Immun.* 74(1):257-264, Jan. 2006.
Trenholme et al., "Antibody Reactivity to Linear Epitopes of Plasmodium Falciparum Cytoadherence-linked asexual gene 9 in asymptomatic children and adults from Papua New Guinea," *Am. J. Trop. Med. Hyg.* 72(6):708-713, 2005.
Tung et al., "Preparation and Applications of Peptide—Oligonucleotide Conjugates," *Bioconjugate Chem.* 11(5):605-618, Sep./Oct. 2000.
Tung et al., "Preparation of Oligonucleotide-Peptide Conjugates," *Bioconjugate Chem.* 2:464-465, 1991.
Unger et al., "Monolithic Microfabricated Valves and Pumps by Multilayer Soft Lithography," *Science* 288:113-116, Apr. 2000.
Van Gemen et al., "Quantification of HIV-1 RNA in plasma using NASBAä during HIV-1 primary infection," *Journal of Virological Methods* 43:177-188, 1993.
Van Lintel, "A Piezoelectric Micropump Based on Micromachining of Silicon," *Sensors and Actuators* 15:153-167, 1988.
Vinayagamoorthy et al., "Nucleotide Sequence-Based Multitarget Identification," *J. Clin. Microbiol.* 41(7):3284-3292, Jul. 2003.
Vivès et al., "Selective Coupling of a Highly Basic Peptide to an Oligonucleotide," *Tetrahedron Letters* 38(7):1183-1186, 1997.
Walker et al., "Strand displacement amplification—an isothermal, in vitro DNA amplification technique," *Nucleic Acids Research* 20(7):1691-1696, 1992.
Walker, "Empirical Aspects of Strand Displacement Amplification," *PCR Methods and Applications* 3:1-6, 1993.
Wang et al., "Molecular engineering of DNA: molecular beacons," *Angew Chem Int Ed Engl* 48(5):856-870, 2009.
Watson et al., Molecular Biology of the Gene, 4th Ed., Benjamin Cummings Publishing Company, Menlo Park, California, Jan. 1987.
Weigl et al., "Fully integrated multiplexed lab-on-a-card assay for enteric pathogens," Proceedings of SPIE—The International Society for Optical Engineering, 2006, vol. 6112 Microfluidics, BioMEMS and Medical Microsystems IV—San Jose, CA, United States.
Weinstock et al., "Sexually Transmitted Diseases Among American Youth: Incidence and Prevalence Estimates, 2000," *Perspectives on Sexual and Reproductive Heath* 36(1):6-10, Jan./Feb. 2004.
Whiley et al., "Comparison of three in-house multiplex PCR assays for the detection of Neisseria gonorrhoeae and Chlamydia trachomatis using real-time and conventional detection methodologies," *Pathology* 37(5):364-370, Oct. 2005.
Witkin et al., "Detection of Chlamydia trachomatis by the polymerase chain reaction in the cervices of women with acute salpingitis," *Am J Obstet Gynecol* 168(5):1438-1442, May 1993.
Woehlbier et al., "Analysis of Antibodies Directed against Merozoite Surface Protein 1 of the Human Malaria Parasite *Plasmodium falciparum*," *Infect. Immun.* 74(2):1313-1322, Feb. 2006.
Wu et al., "The Ligation Amplification Reaction (LAR)—Amplification of Specific DNA Sequences Using Sequential Rounds of Template-Dependent Ligation," *Genomics* 4:560-569, 1989.
Yogi et al., "Clinical Evaluation of the Bladder Tumor Marker "TU-MARK-BTA"," *Hinyokika Kiyo* 37(4):335-339, Apr. 1991.
Zhang et al., "Synthesis of clay minerals," *Applied Clay Science* 50:1-11, 2010.

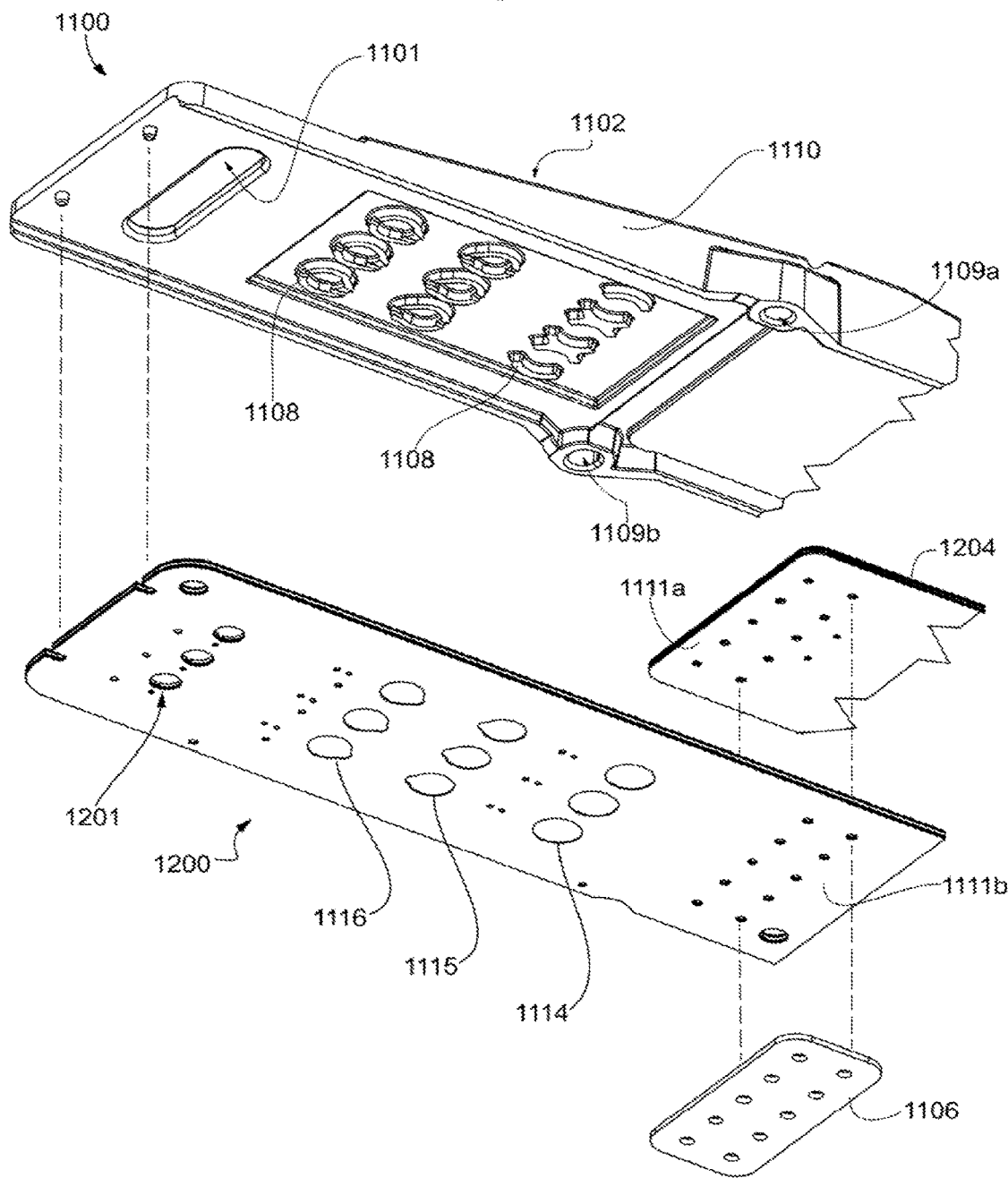

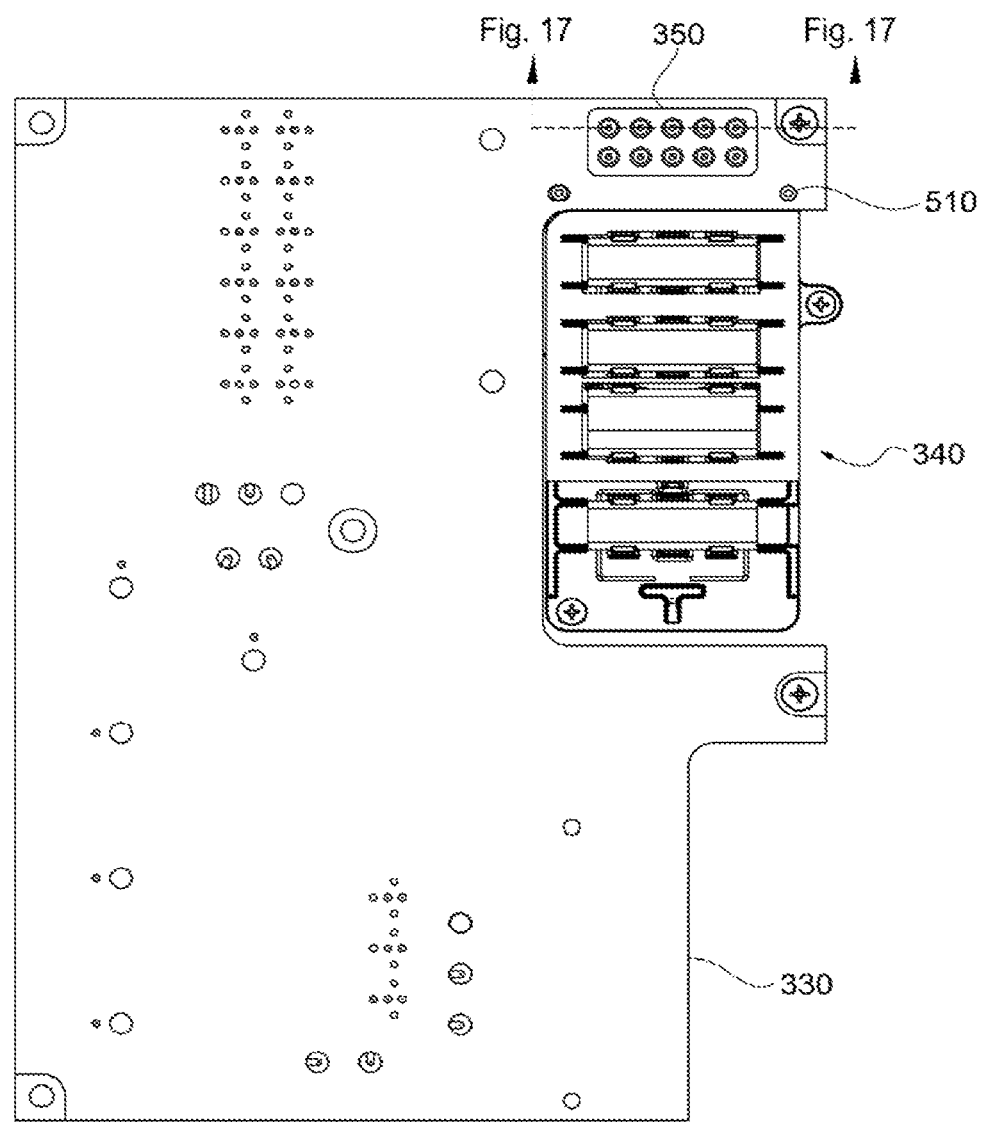

PORTABLE FLUORESCENCE DETECTION SYSTEM AND MICROASSAY CARTRIDGE

TECHNICAL FIELD

The present invention generally relates to a compact fluorescence detection instrument with optical, thermal, mechanical and pneumohydraulic systems for use in diagnostic assays performed in a microassay cartridge.

DESCRIPTION OF THE RELATED ART

Although the benefits of the use of fluorophores as probes for in-vitro diagnostic assays are well known, the most commonly available forms of equipment for such assays are large, complex to use, relatively slow and rely on expensive confocal optics. These attributes make much equipment unsuitable for fully integrated "sample-to-answer" testing in remote locales and on-site at the point of care, where such equipment is required to be rugged, fast, compact, inexpensive, and easy to use. Although automated nucleic acid amplification in a microfluidic cartridge was first proposed some years ago (see Wilding: U.S. Pat. Nos. 5,304,487 and 5,635,358), detection of fluorescent assay targets outside controlled laboratory conditions is still hampered by the lack of portable and robust equipment. Two decades since their inception, molecular diagnostics are still relatively uncommon in the absence of advanced laboratory facilities because of these and other unsolved problems.

Needed to promote broader access to molecular diagnostics are self-contained assay systems designed to operate outside specialized laboratory facilities. Nucleic acid assays are rapidly becoming the "gold standard" for the detection of many different disease types, including infectious diseases, because they offer both higher sensitivity and specificity. Such assays have proven highly specific to a broad range of pathogenic conditions and are useful for tracking genetic strains of a particular disease as is fundamental to epidemiology, for example in discriminating H5N1 avian influenza from other types of influenza A or B, in determining whether a particular pathogen target is of a drug-resistant strain or not, and in detecting toxigenic strains of an enteric isolate such as E. coli O157:H7. Fluorescence-based assays have also been shown to be useful for monitoring conditions such as diabetes, cardiopathies, coagulopathies, immunoassays in general, and for detection of endotoxin in foods or drug products for example. Improved equipment is particularly needed for the large numbers of remote health clinics in the developing world where access to health care is limited and many infectious diseases are endemic, and health and life expectancy are poor.

In a typical fluorescence assay system, a fluorescent probe or fluorophore absorbs light having a wavelength or range of wavelengths and becomes excited; and the fluorophore then emits a fluorescent signal. The activity or inactivity of the fluorophore is indicative of the assay result. The emission signal has a wavelength or range of wavelengths that is generally longer than the exciting light (but may be shorter as in "up-converting fluorophores"). A dichroic beam splitter or band-pass filter, or combination thereof, is then used to separate the fluorescent signal from other light, and the signal is passed to a sensor. The sensor is often a photodiode, and generates an electrical signal that can be used to score the assay. Qualitative and quantitative assays using real time or endpoint fluorometry are feasible.

In such systems, a liquid sample is conveyed via a microfluidic channel into a detection chamber or channel of a microfluidic cartridge where a fluorescent probe admixed with or native to the sample is excited by an excitation source. Controls may be run in parallel or multiplexed in the assay channel. Emitted light is measured to determine the presence or absence of a target. A plurality of detection channels may be arranged in the detection region of the microfluidic cartridge. Assays involve making one or more measurements of fluorescence; fluorophores may be used as markers for nucleic acid amplicons formed in an amplification step, or more generally for the presence or absence of a fluorescent assay target. Real time fluorometry, FRET, qPCR, thermal melt curves, kinetic and rate endpoints for assay scoring and validation are also known in the art.

Known fluorescence detectors typically employ relatively expensive optical components (such as confocal optics, lasers and aspheric lenses) in order to pick up and localize fluorescent emissions present within a microfluidic cartridge or microarray. WO 98/049543 to Juncosa, for example, teaches three dichroic beam splitters in a single optical train, one for controlling excitation source power and another for controlling reflectance signal; the third dichroic beam splitter is used for discriminating probe-specific fluorescent emission. One or more lenses serve to focus the excitation beam on the sample. Juncosa further teaches use of an aperture at the inlet of a photomultiplier and optical objective lens components of a confocal microscope for controlling an imaging beam with a resolution of "microlocations" at about fifty microns. "By restricting the scope of the illumination to the area of a given microlocation, or a fraction thereof, coupled with restricting the field of view of the detector to the region of illumination, preferably through use of an aperture, significant improvements in signal-to-noise ratio may be achieved." [p 7, lines 10-15]. These teachings are presaged by U.S. Pat. No. 3,013,467 to Minsky, U.S. Pat. No. 5,296,703 to Tsien, U.S. Pat. No. 5,192,980 to Dixon, U.S. Pat. No. 5,631,734 to Stern, U.S. Pat. No. 5,730,850 to Kambara, and are reiterated in U.S. Pat. No. 6,614,030 to Maher and U.S. Pat. No. 6,731,781 to Shams, among others. Maher uses lasers, fiber optics, a quartz plate and aspherical lenses with mini-confocal optical system in order to optimize focusing and emission at a ten micron-sized spot at the center of the microfluidic chamber.

Similarly, in U.S. Pat. No. 6,635,487, Lee affirms that focusing the cone of the excitation beam on the plane of the sample "provides the greatest intensity to enhance analytical detection measurements on the assay chips.". This teaching thus encapsulates the prior art.

In a more recent filing, US Patent Application 2008/0297792 to Kim teaches that an image of an LED serving as a light source for fluorescence detection in a microfluidic chip is projected onto a sample as an "optical spot" by an objective lens. The optical spot is focused at the middle of the depth of a fluid in a chamber in the microfluidic chip. Fluorescence emitted by the sample is collimated as nearly as possible to parallel rays by the objective lens and focused on an avalanche photodiode. The requirement for high precision in alignment relates to the dichroic mirror because the stopband will be shifted for light rays that do not enter the mirror at a 45° angle, as is well known. Thus the teachings of Kim reflect the generally recognized state of the art.

In PCT Publication WO2008/101732 to Gruler, where is described a fluorescence detector head for multiplexing multiple excitation and detection wavelengths in a single light path, it is stated that, "A confocal measurement means that the focus of the illumination optics or the source, respectively intrinsically is the same as the focus of the detection optics or sensor, respectively.". Gruler goes on to state, "The confocal optics [of the invention] . . . secures highest signal and lowest background intrinsic features of confocal design", i.e., according to Gruler the highest possible signal and lowest noise are obtained with confocal optics.

While the consensus teaching of the prior art arose out of the specialized use of confocal optics for epifluorescence microscopy, the teaching has been widely and uncritically applied to microfluidic, lateral flow, capillary electrophoresis and microarray applications. However, we have found that this approach is not well suited to liquid phase microfluidic diagnostic assays where detection of one or more molecular probes in a fluid-filled channel is required. Due to effects such as photoquenching, thermo-convection, and the occasional presence of bubbles or gradients in a fluid-filled channel, colocalizing the focal point of the excitation beam and emission cone in the plane of the sample chamber can lead to unacceptable instability, loss of signal, quenching, noise, irreproducibility and overall loss of sensitivity in the results. Because of the higher temperatures of PCR, for example, outgassing of reagents and sample is not an uncommon problem, and interference from bubbles entrained in the liquid sample is a frequent problem. The conventional approach also requires more expensive optical components and thus is disadvantageous for widespread application outside advanced clinical laboratories.

A second problem is assay validation. Current standards for validation of infectious disease assays by PCR, for example, have come to rely on use of spiked nucleic acid templates or more preferably, co-detection of endogenous normal flora, for example ubiquitous non-pathogenic *Escherichia coli* in stools where pathogens such as *Salmonella typhi* or *E. coli* O157 are suspected. Another ubiquitous endogenous template is human 18S rRNA, which is associated with higher quality respiratory and blood samples. Co-amplification and detection of an endogenous template ensures confidence in the assay results but is difficult to achieve in practice because of possible crosstalk between the fluorophores used as markers. When using high gain amplification, some level of crossover in the spectra of the excitation and emission of fluorophores commonly selected for multiplex PCR is typical and expected. Thus a solution that would isolate fluorescent signals with spectrally overlapping shoulders by using separate optical channels within a scanning detector head having shared low-noise electronics for downstream processing would be a technological advance of benefit in the art.

A third problem is portability. Use of disposable cartridges has proved beneficial because cross-contamination due to shared reagent reservoirs and shared fluid-contacting surfaces is avoided. However, configuring a precision optical instrument platform for accepting disposable cartridges is problematic. Problems include inaccuracies and stackup in mechanical tolerances that affect cartridge alignment and detector head positioning, the need for forming a highly conductive thermal interface between the plastic disposable cartridges and heating sources in the instrument, the need for sealing the pneumatic interface between control servos on the apparatus and microvalves on the cartridge, and the necessarily shorter light path available in a microfluidic cartridge (typically about or less than 1 millimeter), which without optimization can lead to loss in sensitivity. A simultaneous solution of these interlocking problems is only achieved by extensive experimentation and development, most often guided by trial and error in this highly unpredictable art. Thus there is a need in the art for numerous improvements, elements of which are the subject of the disclosure herein.

BRIEF SUMMARY

The present invention addresses the problem of reliable and sensitive detection of fluorescent probes, tags, fluorophores and analytes in a microfluidic cartridge in the presence of bubbles and other interfering inhomogeneities in a liquid sample, in a first aspect of the invention, by providing a reflective mirror face formed on a heating block that contactingly interfaces with a thermo-optical window on the underside of the detection channel or chamber containing the liquid sample. The mirror face is formed on the top surface of a heating block and contacts the lower optical window of the detection chamber during use, avoiding the complexity and expense of manufacturing an integral mirror on the bottom of each disposable cartridge, and allowing us to use thinner, more compliant films with lower resistance to heat transfer and transparent optical characteristics for the thermo-optical window of the cartridge. The mirror face is optically flat and polished to improve both heat transfer and fluorescence emission capture. A scanning objective lens is positioned above an upper optical window on the top of the microfluidic cartridge. Excitation light is transmitted through both the upper optical window and the lower thermo-optical window before striking the mirror and reflecting back. Direct and reflected emissions are collected by the objective lens and focused on a detection sensor such as a photodiode, photocell, photovoltaic device, CMOS or CCD chip.

Also, and starkly in contrast to the teachings of the prior art, the problem of fluorescence detection is shown to be solved by configuring the optics so that the excitation optics are decoupled from the emission optics on a common optical path. In a preferred embodiment, by trial and error, when using the back mirror, we have found that it is advantageous to place the focal point of the excitation cone near or behind the plane of the reflective mirror and to independently position the emission cone so that emissions are preferentially focused on the detection sensor. Optionally, the excitation cone can be refocused in the near field by directing a convergent source beam on the objective lens. Surprisingly, decoupling increases sensitivity, improves limits of detection, and reduces noise or interference of bubbles and other inhomogeneities in the sample.

Contrary to the teachings of the prior art, we find that the conventional confocal localization of the excitation and emission signal is less effective in generating a robust signal over a wide range of sample and operating conditions. Therefore, in one aspect of the invention, it was found that optimization of signal detection may be improved by displacement of the focal point of the excitation light from the plane of the sample to a point behind the sample, a technological advance in the field of low cost optics for use with microfluidic fluorescence assays. Decoupling of excitation and emission optics (i.e., different focal points for excitation light and emission signals) flies against decades of prior art dedicated to the principles (first espoused by Minsky in U.S. Pat. No. 3,013,467) that form the foundation of conventional practice in confocal microscopy, epifluorescence detection, and microfluidic fluorescence assays. The prior art teachings have lead to the use of aspherical lenses, laser diodes, and precise parfocal alignment of the detection optics with the excitation optics. In contrast, the optics required for delocalized focus of the excitation cone as described here are fortuitously of very low cost and do not require precision assembly or maintenance, as is desirable for manufacturing a low cost, portable instrument.

The mirror face on the top surface of the heating block under the detection chamber is used to increase sensitivity by improving the light-gathering capacity of the objective lens. As the objective lens is placed closer to the detection chamber, a lens of defined angular aperture and numerical aperture becomes more efficient in collecting emissions. Without the back mirror, collection efficiency of a typical system of the prior art is less than 2.5% (assuming for example a 5 mm planoconvex lens). Adding a back mirror can improve this by as much as 200%, and theoretically as much as 400%. And focusing the excitation beam behind the sample chamber can add synergically to any gain in sensitivity by increasing the excitation pathlength by using a mirror. We have found that this is especially advantageous in low aspect ratio microfluidic cartridges, where the optical path length on a z-axis of a cartridge is typically sub-millimeter in length, a significant reduction relative to a standard optical cuvette. Happily, this combination was also found to reduce interferences due to irregularities in the sample chamber such as the presence of small bubbles.

In one embodiment, the mirror is a chromed or polished metal surface on an aluminum or copper heating block, and is also used to transmit heat or cooling for temperature controlled assays, thus achieving another synergy of design. In a preferred embodiment, the mirror is an electropolished chrome surface on an optically flat aluminum block, the aluminum selected for its superior heat transfer characteristics and scaleable thermal inertia. The block is heated by a resistive heating element in contact with the base of the block. The smoothness and flatness of the mirror face favors optimal heat transfer. In this aspect of the invention, the mirrored face is the upper surface of the heating element used for example for FRET detection or thermal melting analysis of fluorescent probes for PCR amplicons. In one embodiment, a combined application of the optical and thermal properties of the mirror-faced heating block is illustrated by construction of FRET melt curves taken by monitoring fluorescence while ramping the temperature of the assay fluid. In another embodiment, the mirror faced heating block is used to adjust or control a reaction temperature in the detection chamber of a microfluidic card while the cartridge is scanned for fluorescence emission. A mirror-faced heating block for use with microfluidic cartridges in real-time and temperature modulated fluorescence assays demonstrates a technical advance in the art.

According to another aspect of the present invention, we have employed a high gain multi-stage amplifier with noise elimination augmented through the use of downstream signal processing firmware compactly mounted in the scanning head. Very high gain amplification and out-of-plane delocalization of the excitation light cone were found to be synergic in optimizing assay discrimination and sensitivity, even in the presence of bubbles which disrupt specular reflection from the mirror face behind the liquid sample, and happily were implemented with no increase in cost.

The complete optical path uses three lenses, the first for collimating excitation from a light source, the second for projecting the excitation source onto the mirror and for collecting a fluorescent emission from any fluorophore in the sample as collimated emissions, and the third for focusing the emissions on a detector. Each fluorophore is optically isolated by a separate optical channel for measurement. A combination of spectrally-specific LEDs, dichroic mirrors, and barrier filters are used to achieve near monochromatic excitation light in each optical channel. The lenses and related optical components, including the dichroic mirror intersecting the light path for separating excitation and emissions wavelengths and filters, are provided in a guiderail-mounted scanning head that moves laterally across the detection chambers. To minimize noise, the head also includes all electronic components for amplifying the signal and an on-board embedded microprocessor for analog and digital signal processing. Even in the presence of bubble foam interferences that defeat signal averaging and baseline subtraction methods of data acquisition, assay scanning data from each optical channel may be accurately evaluated and reported by conversion to a single bit output (i.e., a 1 or a 0). This has been found to be a simple and remarkably effective means for qualitative scoring for the presence or absence of a signal from a particular fluorophore in a liquid sample mixture while the detector head is scanned over the detection chamber or chambers and across the mirror face.

The scanning head and rails are configured with a drive chain coupled to a stepper motor for accurate spatial resolution during scanning. The entire microfluidic cartridge docking bay and optical bench is mounted in an instrument housing at a pitched angle, which we have found advantageous in decreasing bubble entrainment and improving venting during loading, wetout, and mixing operations on the microfluidic cartridge. In a preferred embodiment, the entire optical bench is mounted at an angle of about 15 degrees so that bubbles are displaced from the microfluidic circuitry, necessitating a complete suspension mount for the floating optical bench and the docking bay, and a spring-biased clamping mechanism to ensure active formation of a thermoconductive interface between on-board heating elements mounted in the docking bay on the bottom of the optical bench assembly and the insertable cartridge when the cartridge is loaded into the instrument. A sealed interface between the angled cartridge and a gasketed pneumatic interface port must also be established during docking.

The detector head may be scanned across the detection chamber, or conversely, the microfluidic cartridge may be scanned across the detector. As implemented here, the detector is mounted with a worm gear- or rack and pinion gear-driven stage under control of a stepper motor on twin, paired guiderails. Samples may be scanned on demand by synchronizing data acquisition with motor control; this may be performed using an on-board or external host controller in communication with the embedded microprocessor in the detector head. Surprisingly, such a detector head with integral co-processor, mounted on a linear motion stage for sampling, filtering and averaging measurements on the fly, improved the capability of the system to validate and report assay results despite many potential interferences.

It was expected that there will be variations in fluorescent intensity across the sample well, detection chamber, detection channel or field, which can be a millimeter to several millimeters in width. These variations arise, for example, as a result of inhomogeneities in mixing, from differences in well thickness, from imperfections in the optical windows, from small temperature variations (which can cause accompanying variations in hybridization-dependent fluorescence of amplicons being detected, for example) and from bubbles or foam which may arise from degassing and mixing. It was found that these variations can be minimized by signal digitization over a sampling transect across the detection chamber. A threshold may be used to discriminate positive and negative test results, as will be described further below.

In order to further provide noise elimination, extraneous noise is removed by strobing the excitation beam at a frequency known to prevent interference by AC line fluctuations and other ambient electric or RF interference; resulting in cleaner signal modulation, a modulated signal that also can be filtered to remove the effects of any ambient light leaking into the instrument housing. We have achieved this result by configuring the optics printed circuit board with a dedicated co-processor, and using independent clock frequency and firmware, which efficiently minimizes traffic on a databus connected to the host instrument. The on-board optical signal processor has dedicated instructions stored in EEPROM resident on the optics card, and synchronizes pulses sent to the source LED with interrogation of the sensor photodiode at a frequency selected to limit electromagnetic interference. The firmware is designed to evaluate the difference in signal between strobe illumination bursts of excitation light and background between strobe bursts, and any background due to ambient or extraneous light is readily subtracted by this method.

The resulting optics modules are packaged in a sealed detector housing and can be expanded as a series of optics modules with multiple optical channels for simultaneously scanning multiple samples or fluorophores in series or in parallel. Signal processing is routed to an autonomous co-processor embedded in the detector head, and from there to the host instrument controller. Thus the invention comprises single head/single channel embodiments, dual head/dual channel embodiments, and multi-head/multichannel embodiments and may perform single and multiplex assays on single samples or on multiple samples in parallel.

In general, the assay system comprises a mechanical system enabled for scanning the detector head across the sample, the detector head housing at least one detection channel, and more preferentially a plurality of detection channels, each detection channel comprising an objective lens and optoelectronic circuit elements configured to capture and amplify optical signals received by the objective lens, wherein the mechanical system is operated by a controller and circuitry external to the detector head and the optoelectronic elements are under control of an autonomous daemon resident in firmware associated with a microprocessor embedded within said detector head. Advantageously, segregation of the optical signal acquisition and processing within a shielded detector head where all the components are in close proximity realizes a system for multi-stage amplification with negligible signal noise that would otherwise be associated with the analog functions occurring in the host instrument outside the detector head. The optoelectronic circuit elements are operated in electronic isolation from any external circuitry in the host instrument; including optoelectronic elements configured for signal processing and/or signal digitization under control of the autonomous daemon. We believe that this is an advance in the art.

The detectors were found to function well when housed as dual head and multi-head detectors, where two or more channels in a single housing were configured with fully independent optics, fluorophore-specific filters, dichroic mirrors and source LEDs, reducing crosstalk between multiple fluorophores. The head thus will optionally contain a plurality of light sources mounted on a first circuit board and a plurality of objective lens and associated detectors mounted on a second circuit board, and will collect signals for each of a plurality of fluorophores independently using shared signal processing capability and firmware embedded in the detector head. To reduce noise, no analog signals are transmitted from the detector head to the host instrument.

In this way, light sources for excitation in each channel can be matched to the individual fluorophores. It is no longer necessary to provide white light and an excitation filter to ensure a narrow pass beam of excitation light striking the sample. This simplification proved useful in assay protocols calling for paired collection of "biplex" or multiplex target and control signals. Where, as for FDA CLIA waiver requirements, both target and control templates are amplified, a positive control signal must be present before an assay result on a test sample can be reported or billed. In the absence of a detectable control signal, any target signal detected is not a valid result. In order to meet CLIA waiver requirements, it is necessary that the fluorescence detector be able to detect not only the presence, for example, of a target infectious organism amplified by PCR but also of an endogenous human control organism co-existing with the target and amplified by the same PCR reaction or a PCR reaction conducted in parallel in the instrument, for example.

Such an approach preferably requires that the fluorescent detector have the capacity to determine the presence of both the target and the control fluorophores as a "biplex" ("duplex") amplification reaction mixture in a common detection chamber. A positive amplification control fluorophore is typically used which has fluorescent excitation and emission spectra which is shifted (in wavelength) to be well resolved by selective band pass filters from the fluorescent excitation and emission spectra for the target fluorophore (see FIG. 25 for example). However, according to the present invention, it proved possible to achieve superior resolution by using a dual head detector and by scanning each detection chamber twice in series, once with each optical channel, detecting first the control fluorescence signature, then the test sample fluorescence signature—each scanning pass utilizing separate excitation and emission optics as described above.

A benefit was found by configuring these detectors with fully separated and independent light paths. In this aspect of the invention, the use of a duplex head design ensures that the presence of an amplification control fluorophore in a sample does not inadvertently create a signal in the target channel due to "crosstalk". Such a situation would result in the sample being classed as a "false positive". Conversely, it is also important that there is no crosstalk from the target channel to the control channel, which is likely when multiple signals share a common optical path. Such a situation could result in the positive amplification control being inadvertently deemed present, when this may not be the case, and would lead to reporting of an invalid assay, an unacceptable outcome.

These principles are exemplified by the use of fluorescein or equivalent fluorophore as a molecular probe for the target, and Texas Red or equivalent fluorophores as a molecular probe for the control. A dual head detector, with one detection channel optimized for detection of fluorescein and the other detection channel optimized for Texas Red, each with separate excitation and detection optics, was found to be surprisingly sensitive, accurate and robust. The detector head was moved to position each optical channel in turn over the sample and separate fluorescence readings were made. Surprisingly, this improved resolution and minimized cross talk but did not contribute to higher noise or loss of sensitivity due to the mechanics of moving the head. Because excitation is not performed with white light, but is instead performed at a wavelength specific for an individual fluorophore, quenching of the second fluorophore is not an issue.

In another aspect of the invention, we have found that multiple microfluidic channels can be scanned by sequential traverse of a multihead detector across multiple sample wells, each head being configured with independent optics for excitation and emission of a single fluorophore. Although the excitation and detection optics are separated for each optical channel, signal processing is performed in circuitry shared within the detector head. The detector head perform scans under control of an external controller, while the daemon in the detector head autonomously constructs a map of the sample wells encountered during the scan, the map having datapairs expressing signal intensity as a function of location relative to at least one reference point. In one instance the reference point is a spatial coordinate on a defined scanning path taken by the detector head, where the reference point is associated with a registration feature of said cartridge body, and may be associated with a feature that triggers a mechanical, electrical or optical switch, for example. Sample wells are detected by a change in optical signal strength associated with a wall or edge of the well, or other fiducial that identifies the well edge. In some instances, the reference point is taken as a first edge of a first well, and the map includes information about the width from a first edge to a second edge of each of the wells, so that when liquid is introduced, a background scan for each map point can be subtracted from any optical signals associated with the sample.

Thus in yet another embodiment the invention provides a robust multi-head independent channel fluorescent detection system for a point of care molecular diagnostic assay which has a high degree of specificity directed towards the presence of both a target and an nucleic acid amplification control co-existing in a common or parallel detection chamber. The cleaner signals permit higher gain electronic amplification without a corresponding decrease in signal-to-noise ratio. A first embodiment in this invention realizes a fluorescence detection system having more than two channels, for example to detect target and control mixed in a single detection chamber, and having multiple assay channels for detection of multiple targets. Optionally, the heads may be positioned side-by-side, in an array, or radially, as in a cylinder.

Use of the independent optical pathways fortuitously resulted in reduced need for precision in assembly of lenses, dichroic beam splitters, and associated filter elements, improving the manufacturability of the apparatus. Embodiments of the present invention incorporate inexpensive non-precision optics, plastic lenses, a mirror on the heating block behind the sample window, moveable stage elements, strobed excitation and emission, noise suppression, on-board continuous signal processing over a movable detection field, and more than one optical channel for biplex assay validation by use of paired target and control fluorophores. Despite its high amplification gain, the instrument has proven advantageously resistant to interferences such as electrical noise and bubbles in the detection chamber.

BRIEF DESCRIPTION OF THE SEVERAL VIEWS OF THE DRAWINGS

FIG. 9B illustrates the worm drive operation on the clamping gear rack.

FIG. 10B illustrates the worm drive operation of the clamping gear rack and the platen arm.

FIG. 15 is an exploded view of the microassay cartridge nose with central pneumatic inlet port array.

FIG. 16 is a plan view of the mounting plate with microassay cartridge, showing the position of a sectional view through the pneumatic interface multiport.

DETAILED DESCRIPTION

Figure 1:
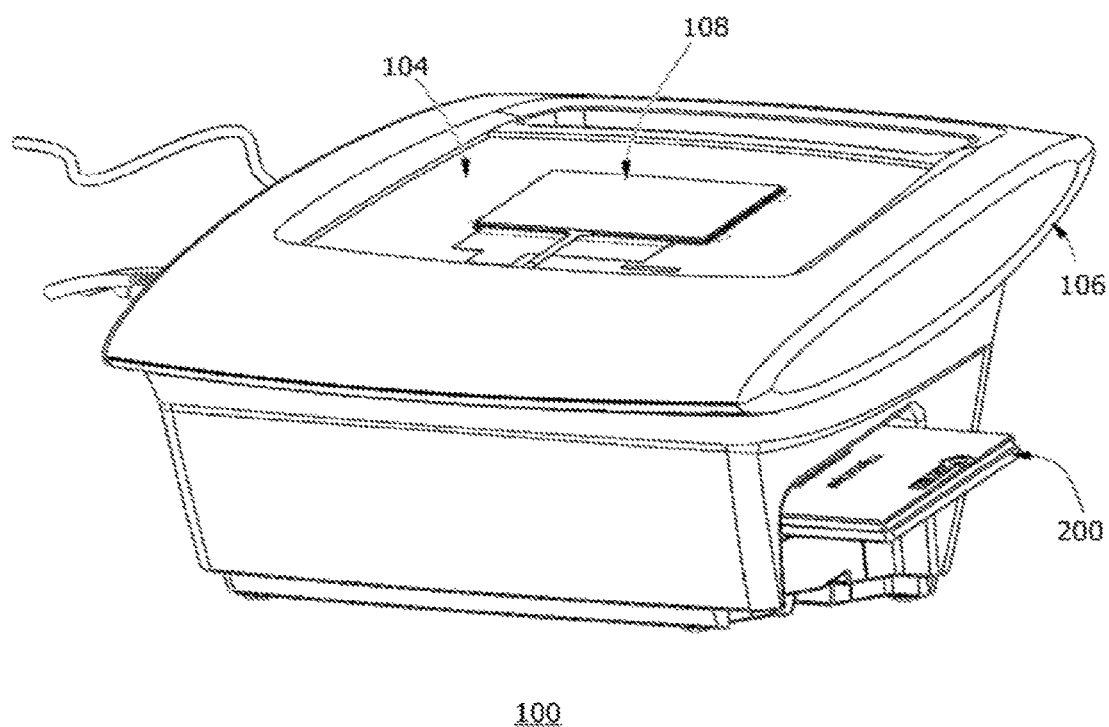
FIG. 1 is a perspective view of an instrument of the invention and a microfluidic cartridge in the docking bay.

Although the following detailed description contains specific details for the purposes of illustration, one of skill in the art will appreciate that many variations and alterations to the following details are within the scope of the claimed invention. The following definitions are set forth as an aid in explaining the invention as claimed.

Definitions

"Daemon" refers herein to a programmable instruction set for optical data acquisition and processing (ODAP) that is stored in firmware which is executed by an embedded microprocessor as an autonomous background process rather than under the direct control of an interactive user or by the host controller. The daemon can be viewed as a virtual machine which operates and controls electronic circuitry that is electronically isolated from noise and is localized in the detector head. Conditioned outputs from multiple amplifiers associated with the detection optics are conditioned and amplified in a tri-stage amplifier, and one of the three amplifier outputs is selected for digitization followed by signal processing and tabulation with positional data. The daemon then compares optical data with background scans and makes a complex determination as to whether the fluorescence is a positive assay result before reporting data to the host system for display to the user. During operation, the host system multitasks to perform various assay functions such as temperature and pneumatics control, detector head scanning, user interface operability, and fault monitoring, and the tasks related to emission signal acquisition and processing are delegated to the daemon, herein termed an "ODAP daemon".

"Angular aperture"—is the angle between the most divergent rays from a single point that can enter the objective lens and participate in image formation.

"Back focal length"—is defined for a lens with an incident beam of collimated light entering the lens as the distance L from the back surface of the lens to the focal point of a cone of focused light. "Back focal positions" indicates that non-collimated rays may be focused at alternate distances from the back of the lens by decoupling the optics from the native focal length of a lens.

Target analyte: or "analyte of interest", or "target molecule", may include a nucleic acid, a protein, an antigen, an antibody, a carbohydrate, a cell component, a lipid, a receptor ligand, a small molecule such as a drug, and so forth. Target nucleic acids include genes, portions of genes, regulatory sequences of genes, mRNAs, rRNAs, tRNAs, siRNAs, cDNA and may be single stranded, double stranded or triple stranded. Some nucleic acid targets have polymorphisms, deletions and alternate splice sequences. Multiple target domains may exist in a single molecule, for example an immunogen may include multiple antigenic determinants. An antibody includes variable regions, constant regions, and the Fc region, which is of value in immobilizing antibodies. Target analytes are not generally provided with the cartridge as manufactured, but are contained in the liquid sample to be assayed; in contrast, "control analytes" are typically provided with the cartridge and are assayed in order to ensure proper performance of the assay. Spiked samples containing target assay may be used in certain quality control testing and for calibration, as is well known in the art.

Means for Amplifying: The grandfather technique was the polymerase chain reaction (referred to as PCR) which is described in detail in U.S. Pat. Nos. 4,683,195, 4,683,202 and 4,800,159, Ausubel et al. Current Protocols in Molecular Biology, John Wiley and Sons, Baltimore, Md. (1989), and in Innis et al., ("PCR Protocols", Academic Press, Inc., San Diego Calif., 1990). Polymerase chain reaction methodologies require thermocycling and are well known in the art. Briefly, in PCR, two primer sequences are prepared that are complementary to regions on opposite complementary strands of a target sequence. An excess of deoxynucleoside triphosphates are added to a reaction mixture along with a DNA polymerase, e.g., Taq polymerase. If the target sequence is present in a sample, the primers will bind to the target and the polymerase will cause the primers to be extended along the marker sequence by adding on nucleotides. By raising and lowering the temperature of the reaction mixture, the extended primers will dissociate from the template to form reaction products, excess primers will bind to the template and to the reaction products and the process is repeated. By adding fluorescent intercalating agents, PCR products can be detected in real time.

Other amplification protocols include LAMP (loop-mediated isothermal amplification of DNA) reverse transcription polymerase chain reaction (RT-PCR), ligase chain reaction ("LCR"), transcription-based amplification systems (TAS), including nucleic acid sequence based amplification (NASBA), "Rolling Circle", "RACE" and "one-sided PCR", also termed "asymmetrical PCR" may also be used, having the advantage that the strand complementary to a detectable probe is synthesized in excess.

These various non-PCR amplification protocols have various advantages in diagnostic assays, but PCR remains the workhorse in the molecular biology laboratory and in clinical diagnostics. Embodiments disclosed here for microfluidic PCR should be considered representative and exemplary of a general class of microfluidic devices capable of executing one or various amplification protocols.

Typically, nucleic acid amplification or extension involves mixing one or more target nucleic acids which can have different sequences with a "master mix" containing the reaction components for performing the amplification reaction and subjecting this reaction mixture to temperature conditions that allow for the amplification of the target nucleic acid. The reaction components in the master mix can include a buffer which regulates the pH of the reaction mixture, one or more of the natural nucleotides (corresponding to A, C, G, and T or U—often present in equal concentrations), that provide the energy and nucleotides necessary for the synthesis of nucleic acids, primers or primer pairs that bind to the template in order to facilitate the initiation of nucleic acid synthesis and a polymerase that adds the nucleotides to the complementary nucleic acid strand being synthesized. However, means for amplication also include the use of modified or "non-standard" or "non-natural" bases such as described in U.S. Pat. No. 7,514,212 to Prudent and U.S. Pat. Nos. 7,517,651 and 7,541,147 to Marshall as an aid to detecting a nucleic acid target.

"Means for detection": as used herein, refers to an apparatus for displaying an endpoint, i.e., the result of an assay, and may include an instrument equipped with a spectrophotometer, fluorometer, luminometer, photomultiplier tube, photodiode, nephlometer, photon counter, voltmeter, ammeter, pH meter, capacitive sensor, radio-frequency transmitter, magnetoresistometer, or Hall-effect device. Magnifying lenses in the cover plate, optical filters, colored fluids and labeled probes may be used to improve detection and interpretation of assay results. "Labels" or "tags" include, but not limited to, dyes such as chromophores and fluorophores; and chemoluminescence as is known in the prior art. QDots, such as CdSe coated with ZnS, decorated on magnetic beads, or amalgamations of QDots and paramagnetic Fe3O4 microparticles, are a convenient method of improving the sensitivity of an assay of the present invention. Fluorescence quenching detection endpoints are also anticipated. A variety of substrate and product chromophores associated with enzyme-linked immunoassays are also well known in the art and provide a means for amplifying a detection signal to improve the sensitivity of the assay, for example "up-converting" fluorophores. Fluorescence and optical detectors may include photodiodes, photovoltaic devices, phototransistors, avalanche photodiodes, photoresistors, CMOS, CCD, CIDs (charge injection devices), photomultipliers, and reverse biased LEDs. Detection systems are optionally qualitative, quantitative or semi-quantitative.

"Molecular beacon"—is a single stranded hairpin-shaped oligonucleotide probe designed to report the presence of specific nucleic acids in a solution. A molecular beacon consists of four components; a stem, hairpin loop, end-labeled fluorophore and opposite end-labeled quencher. When the hairpin-like beacon is not bound to a target, the fluorophore and quencher lie close together and fluorescence is suppressed. In the presence of a complementary target nucleotide sequence, the stem of the beacon opens to hybridize to the target. This separates the fluorophore and quencher, allowing the fluorophore to fluoresce. Alternatively, molecular beacons also include fluorophores that emit in the proximity of an end-labeled donor. 'Wavelength-shifting Molecular Beacons' incorporate an additional harvester fluorophore enabling the fluorophore to emit more strongly. Current reviews of molecular beacons include Wang K et al, 2009, Molecular engineering of DNA:molecular beacons. Angew Chem Int Ed Engl, 48(5):856-870; Cissell K A et al, 2009, Resonance energy transfer methods of RNA detection, Anal Bioanal Chem 393(1):125-35 and Li Y, et al, 2008, Molecular Beacons: an optimal multifunctional biological probe, Biochem Biophys Res Comm 373 (4):457-61. Recent advances include Cady N C, 2009, Quantum dot molecular beacons for DNA detection. Methods Mol Biol 554:367-79.

Fluorescence nucleic acid assays include amplification with tagged primers and probe-based detection chemistries. Fluorescent products can be assayed at the end of the assay, or by measuring the amount of amplified product in real time. While not limiting, TaqMan Probe (Applied Biosystems) which relies on displacement and polymerase-mediated hydrolysis of a 5' reporter dye with 3' quencher construct, FRET hybridization probes, dual oligo FRET-based probes (Roche), minor groove binder-conjugated hybridization probes (MGB probes, Applied Biosystems), Eclipse probes, Locked NA Probes (Exiqon/Roche), Amplifluor primer chemistries, Scorpions primer chemistries, LUX primers, Qzyme primers, RT-PCR, among others, are all suitable in the present invention. Intercalation dyes may also be used. Reverse transcriptase is used to analyze RNA targets and requires a separate step to form cDNA. Recent advances include Krasnoperov L N et al. 2010. Luminescent probes for ultrasensitive detection of nucleic acids. Bioconjug Chem 2010 Jan. 19 epub.

In addition to chemical dyes, probes include green fluorescent proteins, quantum dots, and nanodots, all of which are fluorescent. Molecules such as nucleic acids and antibodies, and other molecules having affinity for an assay target, may be tagged with a fluorophore to form a probe useful in fluorescent assays of the invention.

"FRET" (Fluorescence Resonance Energy Transfer)—is a fluorescence technique that enables investigation of molecular interactions. It depends on the transfer of energy from one fluorophore to another fluorophore (i.e., a donor and a quencher) when the two molecules are in close proximity such a when hybridized. Recent advances include Carmona A K et al [2009, The use of fluorescence resonance energy transfer (FRET) peptides for measurement of clinically important proteolytic enzymes, An Acad Bras Cienc 81(3): 381-92].

Unless the context requires otherwise, throughout the specification and claims which follow, the word "comprise" and variations thereof, such as, "comprises" and "comprising" are to be construed in an open, inclusive sense, that is, as "including, but not limited to". Reference throughout this specification to "one embodiment", "an embodiment", "one aspect", or "an aspect" means that a particular feature, structure or characteristic described in connection with the embodiment or aspect may be included one embodiment but not necessarily all embodiments of the invention. Furthermore, the features, structures, or characteristics of the invention disclosed here may be combined in any suitable manner in one or more embodiments. "Conventional" is a term designating that which is known in the prior art to which this invention relates. "About" and "generally" are broadening expressions of inexactitude, describing a condition of being "more or less", "approximately", or "almost" in the sense of "just about", where variation would be insignificant, obvious, or of equivalent utility or function, and further indicating the existence of obvious minor exceptions to a norm, rule or limit.

"Crosstalk"—in fluorescence imaging occurs when the excitation and/or emission spectra of two or more fluorophores (and/or autofluorescence of a substrate) in a sample well overlap, making it difficult to isolate the activity of one fluorophore alone.

Figure 2:
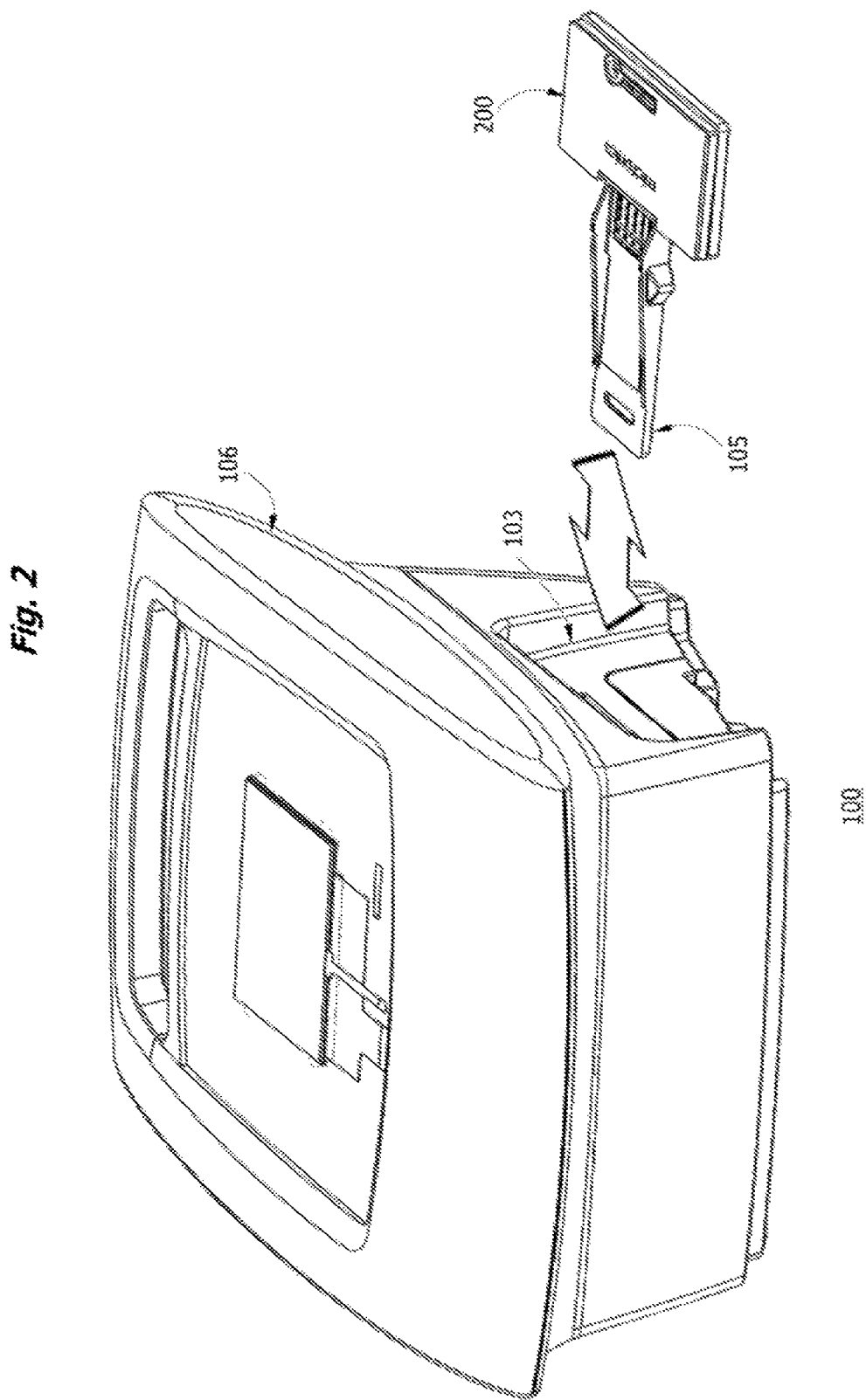
FIG. 2 is an animated view showing the insertion of the microfluidic cartridge in the docking bay.

Turning now to the figures, FIG. 1 is a perspective view of the instrument 100 with a microfluidic cartridge 200 in the docking bay. Shown are membrane panel 104 and touch screen display surface 108 and compact chassis or housing 106. Because all reagents are provided in the microfluidic cartridge, the instrument has full standalone operability. FIG. 2 complements this exterior view by animating the insertion of the microfluidic cartridge anterior nose 105 into the docking bay 103. The docking bay is suspension-mounted and may be tilted at an angle relative to the instrument base, as will be discussed in more detail below.

Figure 3:
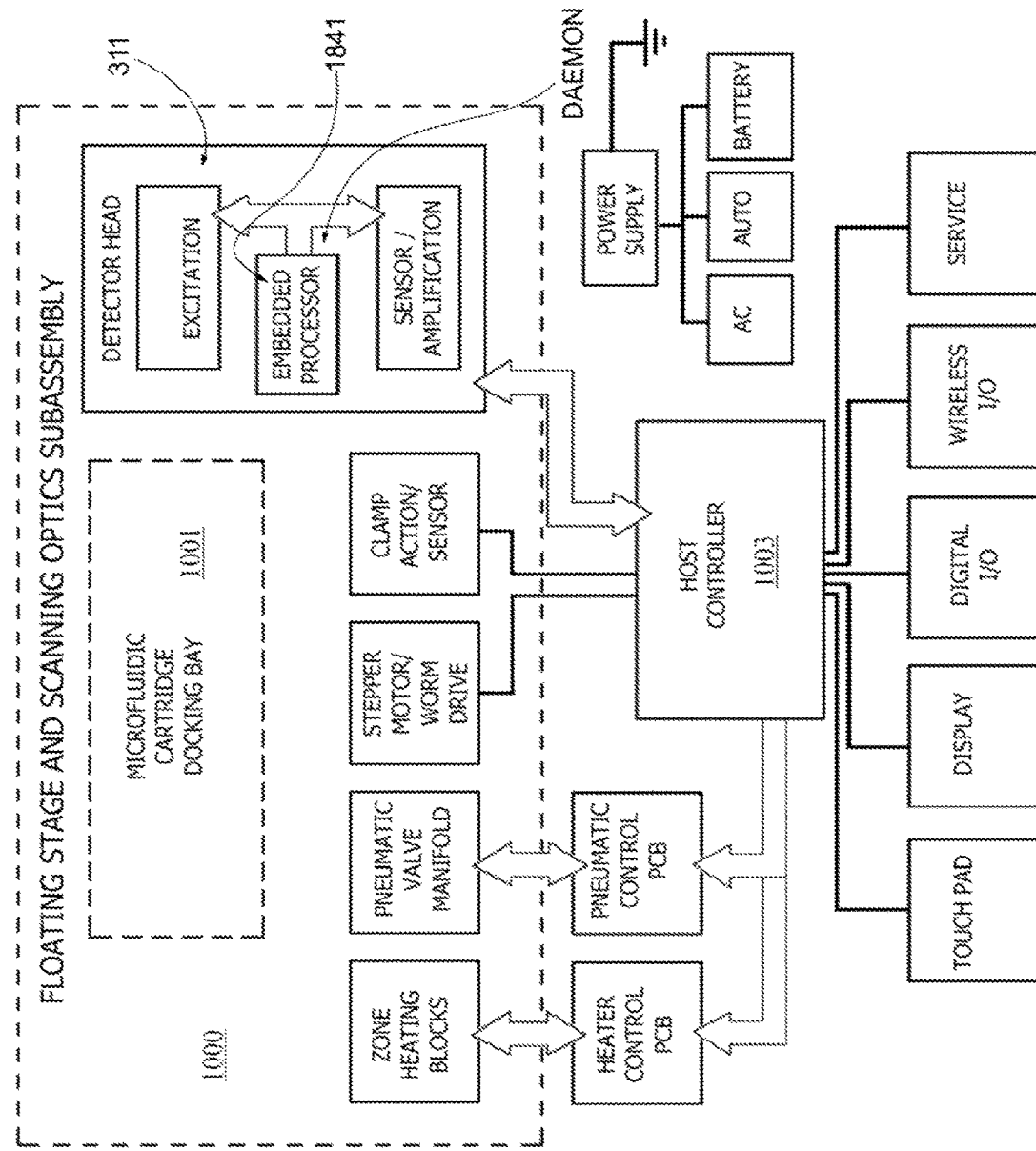
FIG. 3 is a block diagram providing an overview of the functional units, software and firmware of the apparatus.

FIG. 3 is a block diagram providing an overview of the functional units, software and firmware of the assay apparatus. Mechanical, pneumohydraulic, temperature control, optical, and input/output (I/O) systems are coordinated by two digital processors, the first is termed the "host controller", which receives user commands and outputs assay results, and also directs the mechanical, thermal, and pneumohydraulic process steps of an assay, and the second is termed the "embedded microprocessor", which exerts localized control over optical systems, including signal acquisition and processing within the detector head and communicates digital data to the host controller. The optical systems controlled by the embedded processor are shielded within the detector head from the noisy analog circuits within the apparatus housing, permitting high gain amplification in a relatively noiseless environment. Each processor is provided with a separate clock, volatile and non-volatile memory, and performs autonomously of the other.

As an overview, a floating stage (1000, dotted line) within the instrument supports a docking bay (here 1001) for receiving and reversibly clamping a microfluidic cartridge and is provided with a scanning detector head 311. The detector head is scanned across optical windows of the microfluidic cartridge under control of the host controller. The detector head contains subassemblies for providing excitation light and sensors for detecting, amplifying and processing fluorescent emission signals under control of a daemon resident in firmware associated with embedded microprocessor 1841. The floating stage rides on a spring suspension mounted to a stationary baseplate and instrument stand.

Affixed to the stationary baseplate and positioned for interfacing with the floating stage are a heater module with separately controllable heating blocks under control of the host controller 1003, a pneumatics interface connected to pneumatic servos mounted on the base plate 330, which also serves as a pneumatic distribution manifold, a wire harness connecting the stepper motor and the host controller, and wiring harnesses for the clamp motor and related sensors, including pressure switches for measuring the position of the clamp and the microfluidic cartridge, a barcode reader, and temperature monitors. Power is distributed to all systems from a rechargeable battery mounted in the instrument stand, or by direct connection to an AC converter or to a DC source such as an automobile.

The host controller 1003 is mounted on a motherboard which also contains a touch pad panel for operation of the instrument and an LCD display panel. The instrument may transmit data to an outside network or device via a variety of digital serial I/O links, including a wireless networking card or other remote communication device. A special digital junction is provided for service access to the RAM registers and programming, which is software encoded in solid state ROM.

General instructions for operation of the instrument, such as the sequence of pneumatic pulses and valve logic required to operate a particular microassay card having the capability to diagnose a particular disease or pathology from a liquid sample, are provided by programmable software associated with the host controller, which is supplied with volatile and non-volatile memory for executing assays. If for example, the barcode reader detects a particular microassay cartridge, the device is programmed to perform a particular assay recognized from with that barcode and to interpret and display the results in a designated format.

However, the operation of the signal acquisition optics, including modulation of source intensity, signal amplification and filtering, is under control of a daemon resident in the embedded microprocessor 1841 on the sensor PCB within the detector head 311. Thus electrical signals that are highly sensitive to noise are shielded in the detector head from the more noisy environment of the host instrument, and transmission of analog signals from detector head to host A/D converters is completely avoided. This unconventional separation of functions has happily proved highly advantageous in reducing noise susceptibility of the instrument, as is needed for full portability and field operation, and unexpectedly permits use of a high gain tri-stage amplifier in what would be expected to be a noisy electronic environment.

Mechanical Systems

Figure 4A:
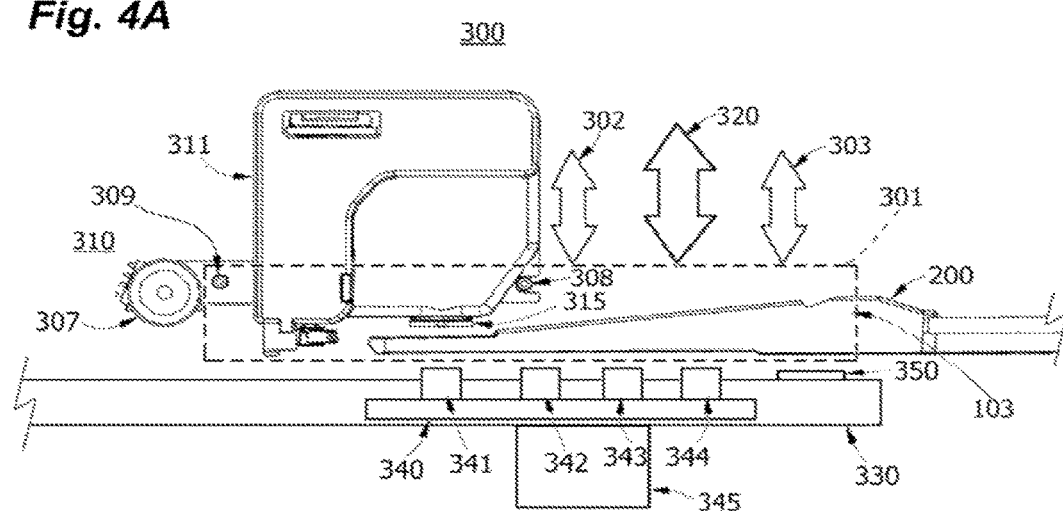
FIG. 4A is a simplified representation of a floating stage with docking bay, optical bench, and clamping mechanism for thermally contacting the microfluidic cartridge with the heater module and scanning the microfluidic cartridge.

The floating stage with on-board optical bench and docking bay is a distinctive feature of the instrument. This feature is introduced conceptually in FIG. 4. FIG. 4A is a conceptual representation of the primary optothermomechanical subsystems of the instrument. The floating stage 300 consists of a tray-like chassis 301 (dashed box) that is suspended on an inclined plane by a four-point spring-mounted suspension (indicated by 302,303) and supports a docking bay 103 for receiving a microfluidic cartridge 200. Also supported on the floating stage 300 is a scanning detector head 311 mounted on paired guiderails (308,309). The cartridge is not part of the instrument 100, but interfaces with the instrument after insertion into the floating docking bay 103.

During operation, the floating stage is clamped (indicated by 320) against a mounting plate (330) and engages contacting surfaces of zone heating blocks (341,342,343,344) of a heater module 340 and associated resistive heating elements and circuits. A fan 345 is provided to dissipate excess heat during cooling. The inclined mounting plate is also provided with a pneumatic interface port 350 for sealedly docking to the base of the microfluidic cartridge. Pneumatic pressure is delivered to the cartridge through the pneumatic interface port from an integral pneumatic distribution "manifold" or system embedded in the inclined mounting plate 330. The pneumatic manifold supplies negative and positive pressure from sources mounted on the inclined mounting plate. A motherboard-mounted, programmable host controller directs pneumatic driving pressure, vacuum, and control pulses to pumps and valves on the cartridge via the internal manifold in the base plate 330 and pneumatic interface port 350.

The detector head 311 is motorized and scanning of the cartridge is performed under the control of the host controller. To scan the detector head along paired guiderails (308, 309) the host controller engages a worm-gear driven by stepper motor 307. The detector head is fitted with an external window with objective lens 315 which scans optical windows in the anterior nose of the microfluidic cartridge and collects raw optical signals. The detector head 311 has its own embedded microprocessor 1841 with resident daemon which functions independently of the host controller for optical signal acquisition. The host controller also regulates temperature in heating elements (341,342,343,344) of heater module 340 and controls a set of solenoid valves and positive pressure and vacuum pump reservoirs linked to the pneumatic interface. The instrument is supplied with a display panel and touch panel for user interactions. Power input is flexible, and is optionally supplied by an AC adaptor, car adaptor, or from a rechargeable battery mounted under the instrument. Also included are optional wireless IO and digital IO ports.

Figure 4B:
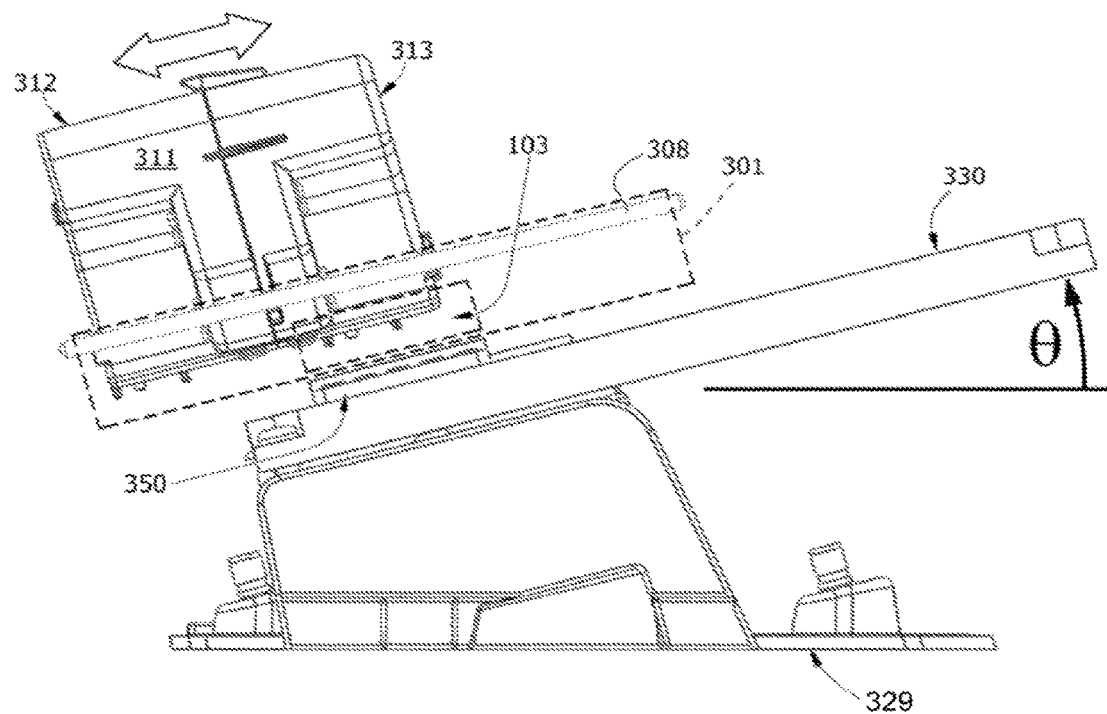
FIG. 4B demonstrates conceptually that the floating stage, docking bay, optical bench and microfluidic cartridge are mounted in the instrument chassis at a defined angle "theta" relative to the ground plane, where the ground plane is horizontal.

FIG. 4B demonstrates conceptually that the floating stage 301, docking bay 103, detector head 311, and microfluidic cartridge 200 may be mounted in the instrument chassis 106 at a defined angle relative to the ground plane. Tilting the cartridge at an angle from the ground plane improves venting during fluid loading and minimizes air entrainment during wetting and mixing operations. Bubble accumulation, which interferes with heat transfer and optical interrogation of assay results, is avoided by this and other innovations disclosed here. The inclined mounting plate 330 establishes the angle of the floating stage 301, cartridge 200, and mechanical components of the clamping 800 and optical scanning 310 subassemblies. We found that bubble accumulation interfered with nucleic acid amplification, and was limited by the angular mount of the stage. This angle "theta" has been found to be advantageous in the range of 10-45 degrees from the ground plane, more preferably 10-20 degrees, and is most preferentially about 15 degrees.

As shown in FIG. 4B, the detector head 311 includes a clamshell housing with mating half shells (312,313). The detector head slides on lateral guide rails 308 and 309 and is under host control of a stepper motor 307 with worm drive. The floating stage chassis 301 is springedly mounted in a four-point suspension and has no direct connection to the inclined mounting plate 330 until clamped. The clamping mechanism is indicated here figuratively by an arrow 320 and will be discussed in more detail below.

One of the two scanning guiderails 308 is readily visible in this view, and is supported at either end by the floating stage chassis or tray 301. The docking bay is indicated by a dashed box (103) and marks the opening for insertion of the nose of the microfluidic cartridge under the detector head 311, which is enabled to scan from side to side as shown (double arrow). The pneumatic interface port 350, shown here as a raised platform under the docking bay, blocks the view of the heater module 340 and heating blocks 341-344 located immediately inferior and in line with the docking bay. Power conditioning, AC adaptors and battery storage functions are mounted beneath the inclined mounting plate 330 above the underside of the instrument stand 329, which is designed to rest on a flat surface.

Figure 5A:
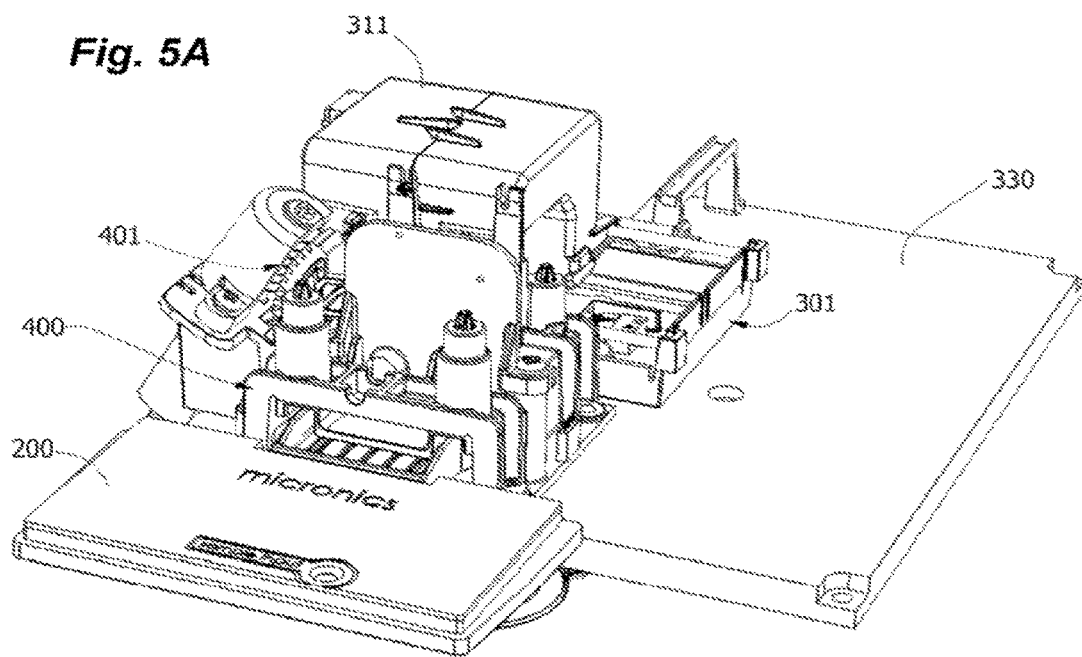
FIGS. 5A and 5B are front and rear interior perspective views from above and below, showing the suspension-mounted stage with docking bay, optical bench, and scanning detector head.
Figure 5B:
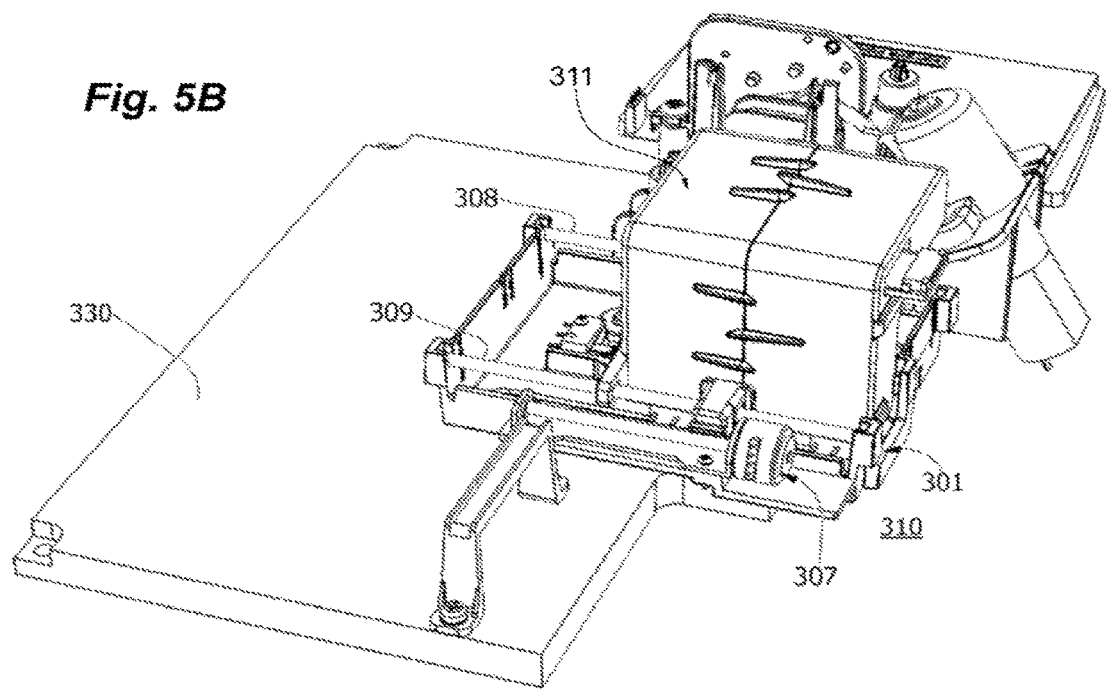

FIGS. 5A and 5B are front and rear interior CAD views from above, showing the suspension-mounted stage with floating chassis 301 with optical bench and detector head 311, and docking bay occupied by a microfluidic cartridge 200. The floating stage is suspended from a saddle shaped support, docking saddle 400, which is rigidly bolted to the inclined mounting plate 330. Also shown is a gear rack 401 that provides clamping pressure, as will be described in more detail below. In FIG. 5B, the guiderails (308,309) and stepper motor 307 of the optical bench are readily recognized. The inclined mounting plate 330 is populated with pumps, vacuum and pressure storage tanks, solenoids and pneumatic control circuitry, which are not shown for clarity of presenting cartridge docking mechanism and scanning detector head.

Figure 6A:
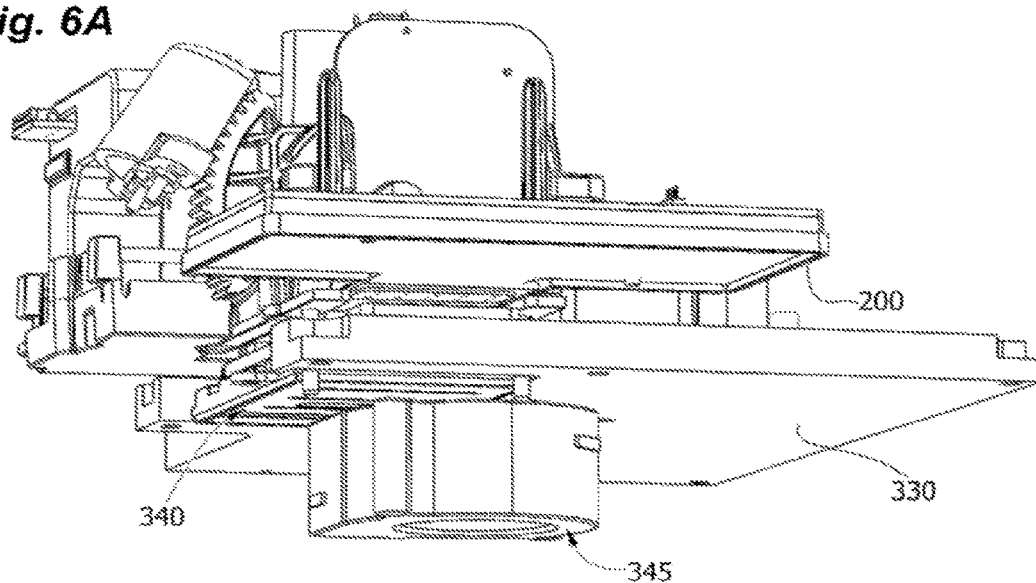
FIG. 6A is a front interior perspective view from below the docking bay, showing the underside heater module and cooling fan.

FIG. 6A is a front interior perspective view from below the docking bay, showing the underside heater module 340 and cooling fan 345. It can be seen that on insertion of the microfluidic cartridge 200 into the docking bay, the heater module 340 is brought into alignment with the underside of the cartridge on alignment pins 510 and resting on step 511 as shown in FIG. 6B.

Heating System

Figure 6B:
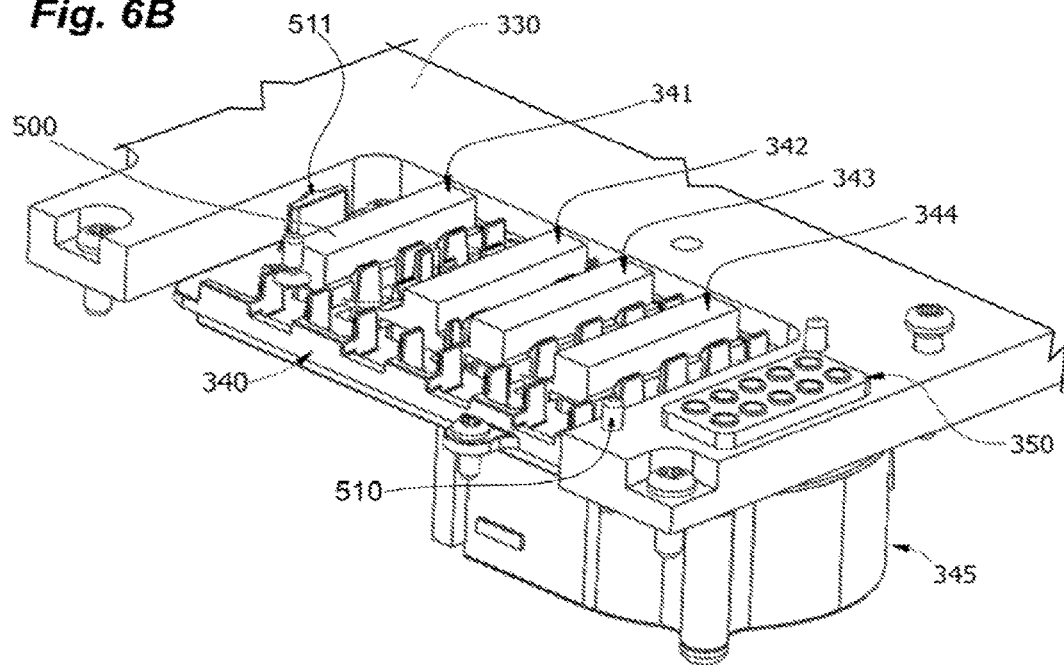
FIG. 6B is a detail of the heater module with heating block elements and mirror face.

FIG. 6B is a detail of the heater assembly 340 with heating block elements ("thermal elements" 341,342, 343,344) and mirror face (500). The superior aspect of the heater module consists of one or more heating blocks, each of which forms a thermal interface with a defined zone on the underside of the microfluidic cartridge for proper operation of the biochemical or molecular biological reactions that occur in the enclosed channels and chambers of the cartridge during the assay. These reactions can be as simple as immunobinding or hybridization, or as complex as nucleic acid amplification or enzymatic dehydrogenation coupled to the formation or consumption of nicotinamide adenine dinucleotide and adenosine triphosphate, or cascading clotting factors, and generally require relatively stringent temperature control for optimal reactivity and specificity. The heating blocks (341, 342,343,344, although the invention is not limited to this configuration) may be spring-mounted and are urged upward in opposition to the downward pressure of the clamping mechanism to establish a high thermal diffusivity contact zone for heat transfer. Each heating block is in thermal contact with a resistive (Coulombic) heating element, generally by means of a compliant thermal pad for good thermal conductivity. Each heating block contacts a thermal window in the microfluidic cartridge. Each window is generally a thin layer of a flexible plastic film, may be less than 3 mils in thickness, and most commonly of a compliant transparent material such as polyethylene terephthalate (Mylar®), although optionally of a cyclic polyolefin or polyimide with good optical transparency, while not limited thereto (see U.S. Pat. No. 7,416,892, which is co-assigned), and also having good thermal conductivity. Thus in one embodiment the invention is a thermo-optical interface for reflective transillumination of a detection chamber in a microfluidic card while controlling or modulating the temperature of a liquid sample in the detection chamber. This feature is of benefit for performing a reaction or reactions associated with an analyte while monitoring an optical signal associated with the analyte. In one exemplary application, thermal melt curves are used to verify FRET hybridization results.

Figure 20:
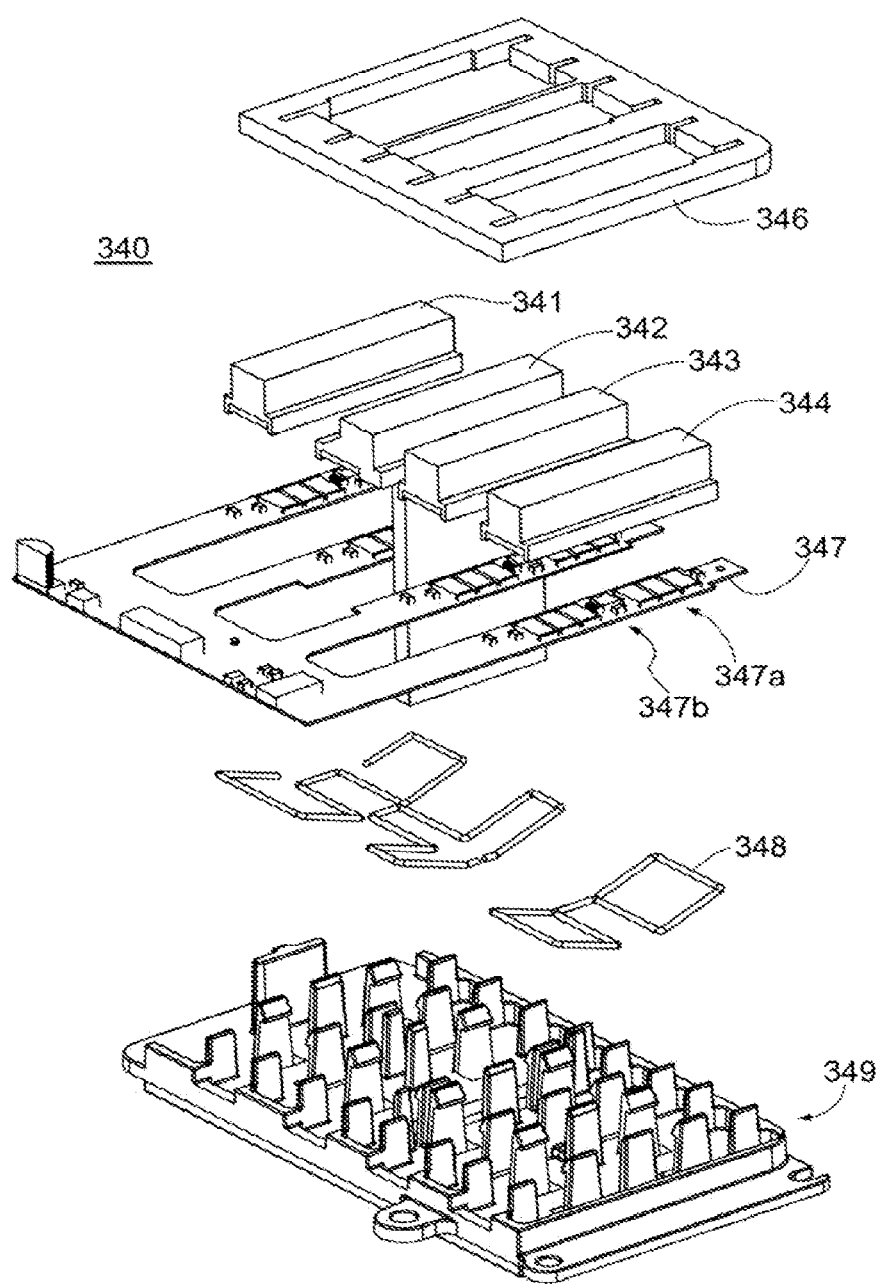
FIG. 20 shows the heater module assembly in exploded view.

Also shown is the fan housing 345, which is used to dissipate heat from heat sinks below the heating blocks and as an adjunct for PID control of temperature in the blocks in combination with resistance heating circuits (FIG. 20). A second fan (FIG. 22) is used to cool the reaction chambers of the assay cartridge, as will be described below.

Heating block 341 in this case is modified by fabrication with a polished chromium mirror face 500 on the upper aspect which contacts and aligns with thermo-optical windows in the microfluidic card 200 during the assay. The thermo-optical window in this case corresponds to a detection chamber enclosed in the cartridge body. The mirror face reflects light from the detector head 311, which scanningly transilluminates the cartridge, back into the objective lens 315, and also reflects any fluorescent emission from the cartridge detection chambers back into the detector head and from there to the detection sensor, which is typically a photodiode, as will be discussed in more detail below. Heating block 341 in this example differs from the other heating blocks, and is generally machined from aluminum, then polished and coated with an underlayer of copper under nickel before application of the chromium mirror face. Electropolishing and/or buffing may be used to form a highly reflective optical finish on the chrome surface. The optically flat superior surface of the block aids in heat transfer and improves sensitivity of fluorescence assays. Happily, the use of the mirror permits simultaneous heating and optical interrogation of the fluid contents of the detection chamber, as is useful for example in optically assaying melting curves.

Other heating zones may be modified similarly to permit optical monitoring with simultaneous temperature control or modulation. The configuration of heating zones and mirrors may be modified or adapted for particular assay/cartridge requirements, and is not limited to the configuration shown here.

FIG. 6B also shows pneumatic interface port 350, here with ten outlets, each independently ported to a source of positive or negative pressure from the pneumatic distribution manifold of the host instrument and independently under the control of a programmable host controller. These outlets interface and seal to mated inlets in the underside of the microfluidic card, and a timed pattern of intercommunicating pneumatic pressure, vacuum and pressure pulses are routed through the pneumatic interface to drive and control the assay in the cartridge.

Figure 7A:
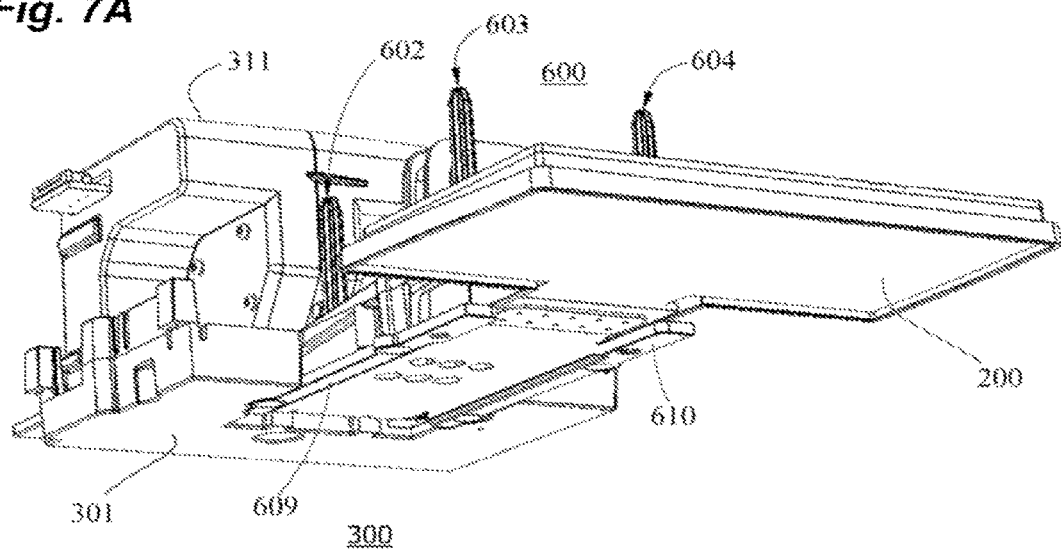
FIGS. 7A and 7B are perspective views of the floating stage with insertable cartridge in place in the docking bay. For clarity, the docking saddle and accessory mounting elements have been removed.
Figure 7B:
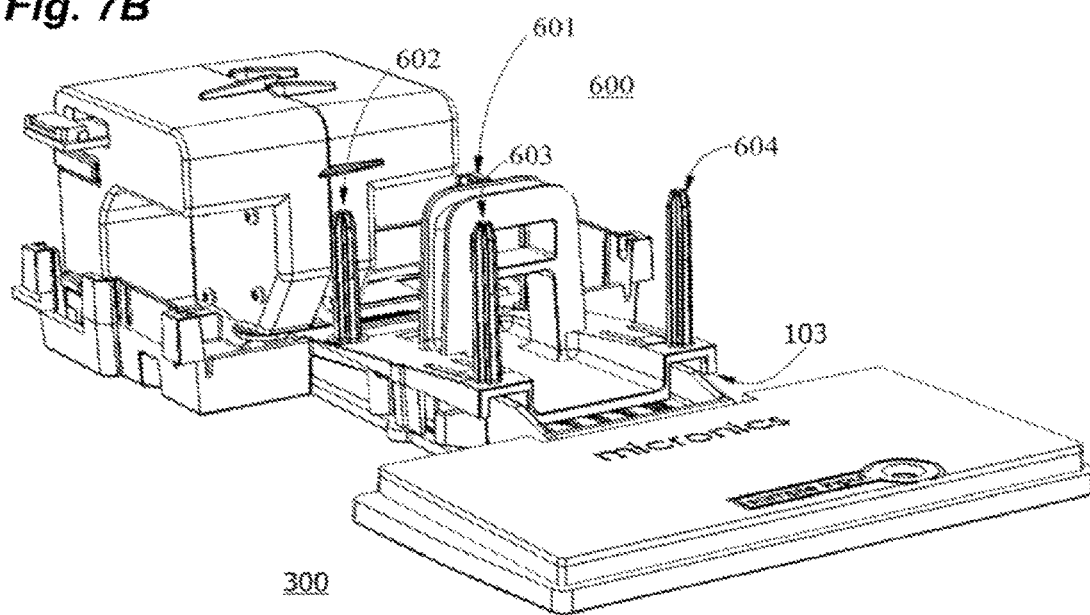

FIGS. 7A and 7B are perspective views of the floating stage subassembly 300 with insertable cartridge in place in the docking bay 103. For clarity, the docking saddle 400 and accessory mounting elements have been removed. It can be seen in FIG. 7A how the inferior surface of the microfluidic cartridge 200 is shaped to be contacted with the mated superior surfaces of the heater module 340 of FIG. 6B. The cartridge is secured and supported under the floating stage 301 by two attached lateral flanges 609 and 610, which are bolted in place and guide insertion.

Clamping Mechanism

In FIG. 7B, four vertical posts (601,602,603,604) forming the male elements of the four-point suspension 600 are apparent on the anterior section of the floating stage 300. These posts are fitted with coil springs (603a in FIG. 8) and inserted into cylindrical suspension housings (605, 606,607, 608) formed as part of the docking saddle member 400. Suspension 600 serves to suspend the floating stage 300 and optical scanning assembly as will be described in more detail in the next figure, FIG. 8. The entire optics bench and docking bay subassembly (shown in FIGS. 7A and 7B) floats on this suspension and is rigidly brought into contact with the rest of the instrument only on downward action of the clamping mechanism as will be described in FIGS. 9 and 10.

Figure 8:
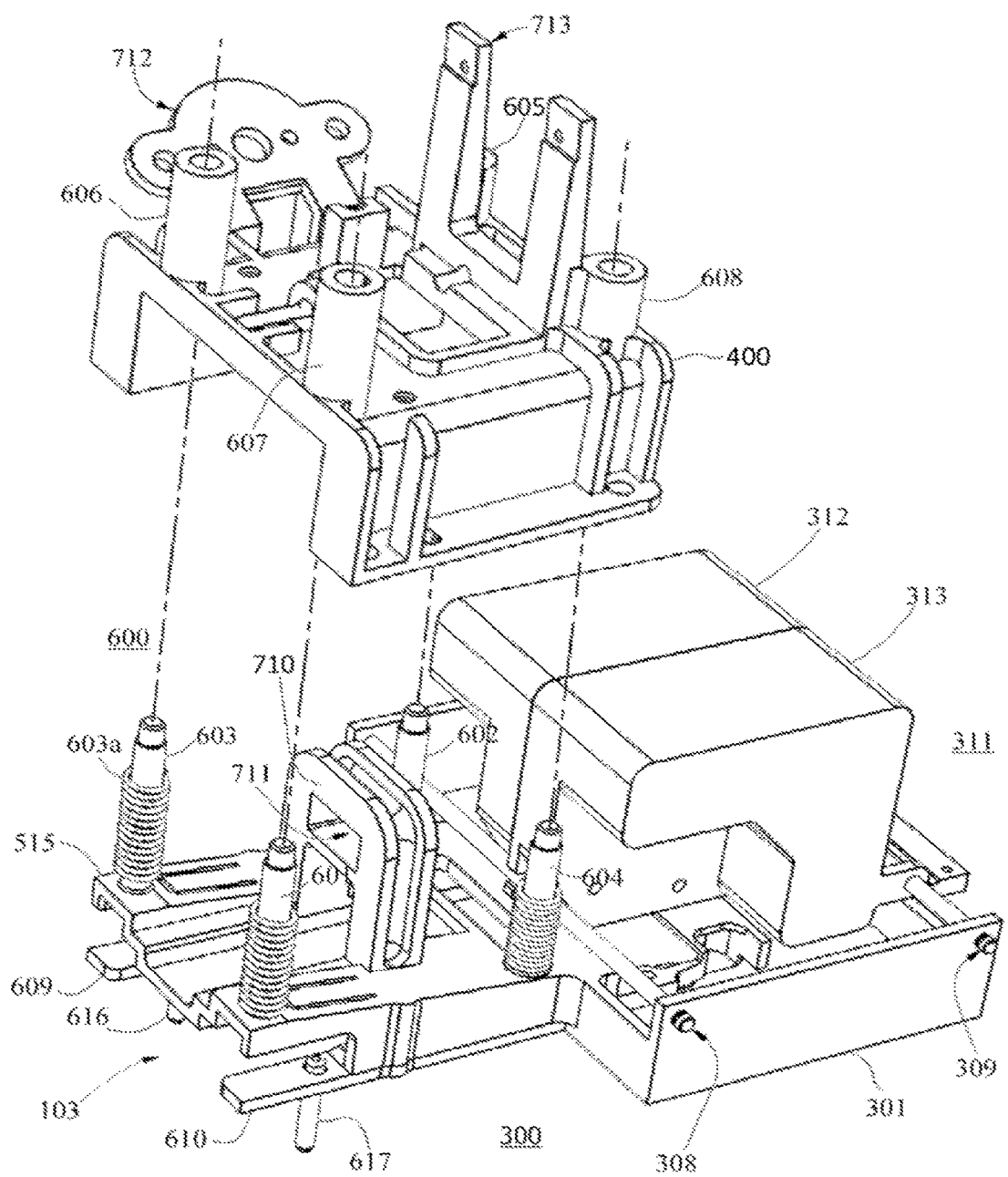
FIG. 8 is a detailed view of the docking bay and floating stage suspended from the underside of the docking saddle. The floating stage is fitted with a four point spring suspension.

FIG. 8 is an exploded view of the floating stage 300 with detector head 311 and docking bay 103 suspended from the underside of the docking saddle 400. The floating stage is fitted with a four point spring suspension with coil springs (replicates of 603a) on each of the four supporting posts (601,602,603,604). Each post is received in a mated suspension housing (605, 606,607,608) of the docking saddle. The microfluidic cartridge 200 is not shown, but it can be seen in this view that the docking bay is configured for receiving the nose of the cartridge at the projecting lip 515 of the docking bay, so that the cartridge rests on lower lateral flanges (609,610). Alignment pins (616,617) ensure that the docking bay seats true when pressed down against the heater module 340. The posterior section of the floating stage, which contains the guiderails (308,309) and detector head 311 for fluorescence scanning, is free of any support other then at the docking saddle and is cantilevered from the docking saddle during operation. The role of guiderails in supporting motion of the scanning detector head 311 is apparent in this view.

The docking saddle is provided with brackets 712 and 713 for attaching the clamping mechanism 800 as will be discussed below, and a bar code reader as is useful in automated operation. Linker arm 710 with slot 711 is engaged by the clamping gear mechanism as discussed below and the floating stage 300 raised or lowered as a single assembly. Linker arm 710 operatively presses the cartridge against the heating blocks.

Figure 9A:
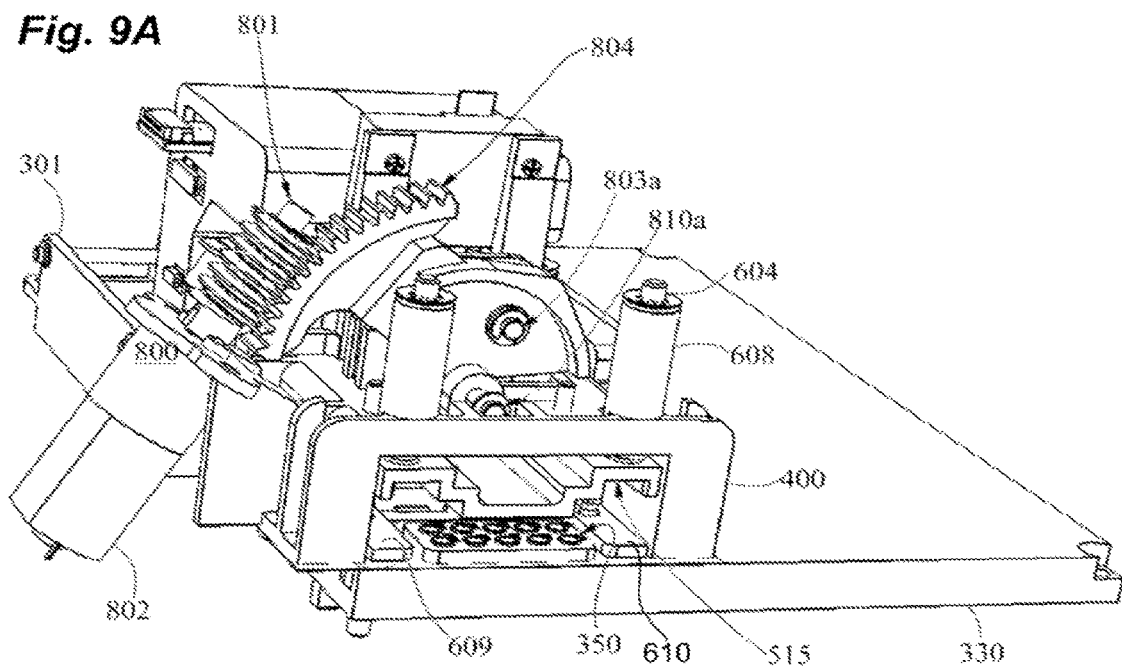
FIGS. 9A and 9B are anterior subassembly views of the clamping mechanism.

FIG. 9A is a frontal view of the clamping mechanism. The bridging shape of the docking saddle 400 is seen to rest above the anterior nose 515 of the floating docking bay 103. Immediately under the docking bay mouth is the pneumatic interface port 350, visible between lateral flanges 609 and 610 forming the channel for receiving the microfluidic cartridge 200. During docking of the loaded cartridge, the function of the clamping mechanism is to urge the floating stage and spring-mounted chassis 301 with inserted cartridge downward onto the pneumatic interface port and heater module as described above.

Docking saddle 400 is bolted on mounting plate 330, and floating stage chassis 301 is suspended on the four-point suspension 600. The suspension springs apply a downward pressure on the floating stage, which is opposed by the suspending action of clamping assembly 800 when in the raised position. Then, when clamping the cartridge, clamp gear piece 804 is driven by worm gear 801 and worm gear motor 802, driving travelling axle 803 in a downward arc. The axle pin 803a is attached to a cam block (901, visible in FIG. 9B). Linker arm (710, visible in FIGS. 8 and 10A) follows the cam-action of the clamping gear 401 and slider block 901 up or down on the four-point suspension. When disengaging the cartridge, the action is reversed. Worm gear motor 802 is run clockwise, raising pin 803a and cam block 901, thus lifting the linker arm 710, which is part of the stage chassis assembly 301, and then reversed (double arrow). When the stage chassis is in the uppermost resting position, the microfluidic cartridge can be removed from the instrument. Mechanical fiducials or alignment pins are used to register the cartridge in the instrument docking bay during the assay.

Figure 9B:
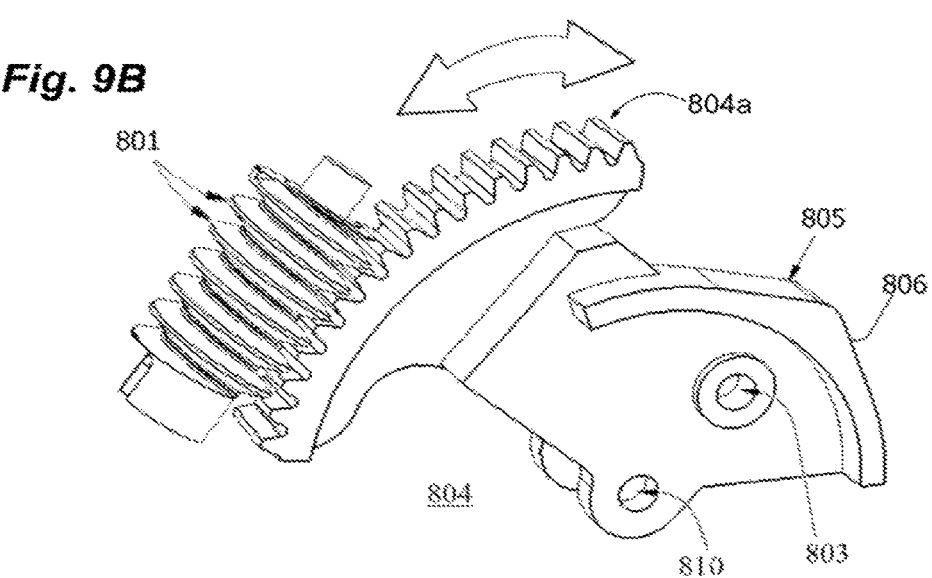

FIG. 9B is a detailed view of the front side of the clamp gear piece 804 with gear comb 804a and worm drive gear 801, showing also cam follower surfaces 805 and 806 on the anterior edge of the gear member that are used by pressure switches to monitor the position of the gear and actuate coordinated mechanical functions by the host controller. For simplicity, the pressure switches are not shown. Axle 810 is the center of rotation for the piece and rotates on pin 810a. Axle 803 travels during rotation of the gear piece, driving a slider block which engages with the stage chassis as shown in the following figure.

Figure 10A:
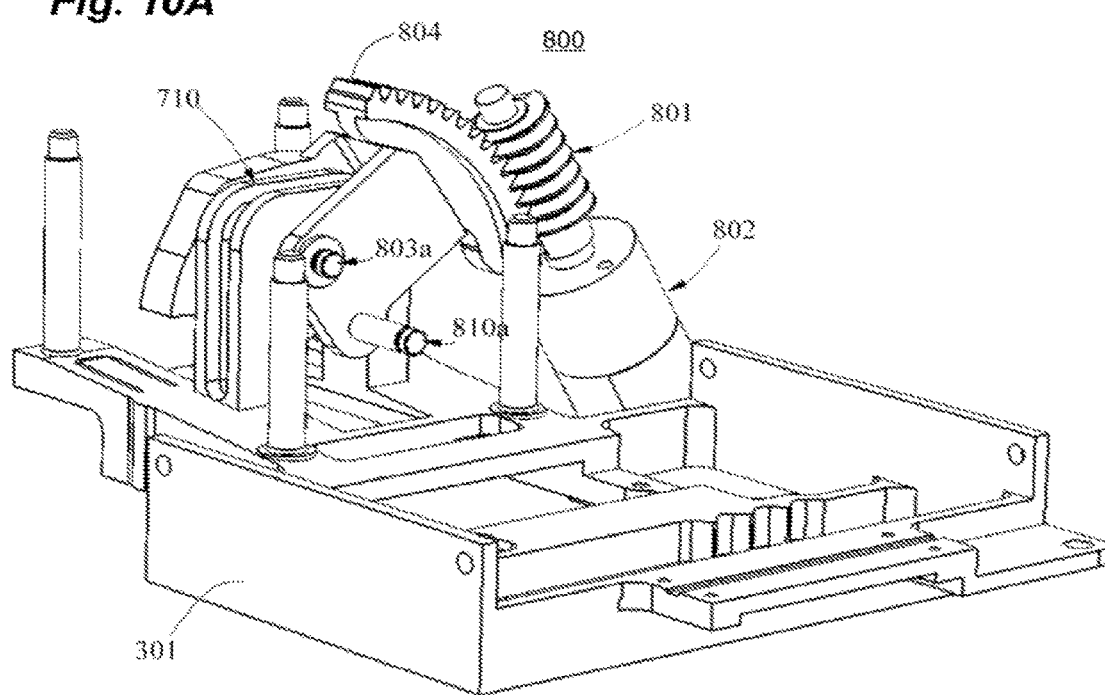
FIGS. 10A and 10B are posterior subassembly views of the clamping mechanism.
Figure 10B:
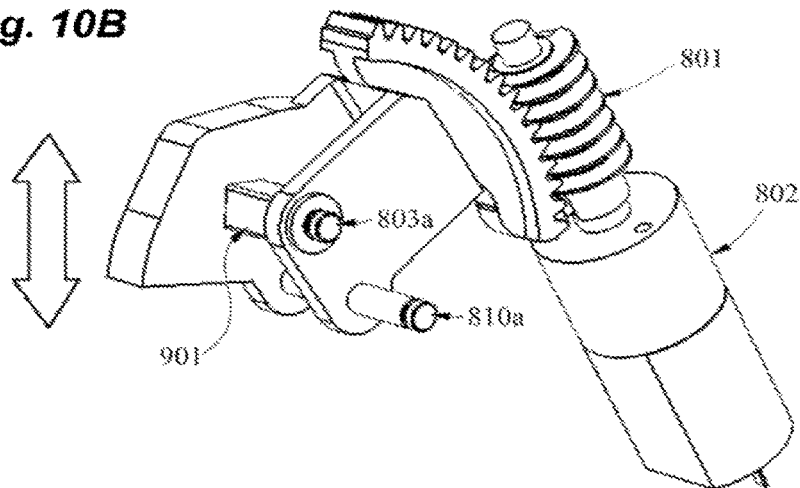

FIGS. 10A and 10B are mechanical drawings showing the action of the clamping mechanism assembly 800. The purpose of the clamp gear-driven cam is to raise and lower the floating stage 301. The clamping gear piece 804 pivots on stationary axle 810, so that travelling axle 803 scribes an arc upward or downward, propelling the linker arm 710 up or down vertically (double arrow). Slider block 901 captive on pin 803*a* slides left to right in a slot 711 in the linker arm (710, see FIG. 8) to accommodate the lateral vector of the motion of the clamp gear while raising or lowering the floating stage 300. The upward movement of the floating stage is opposed by springs 603*a* as shown in the preceding figures. FIG. 10B is a detailed view of the rear side of the clamp gear piece 804 and worm drive gear 801 showing the central axle 810*a* and eccentric cam block axle 803*a* and cam slider block (901).

The mechanism illustrated here is not limiting, insofar as the invention can be realized in alternate ways, for example by clamping up from the bottom rather than down from the top, or by magnetically clamping rather than mechanically clamping. Other spring means may be selected from coil spring, leaf spring, torsion spring, helical spring, and alternatives such as pneumatic canisters (e.g. gas springs) and elastomeric materials or other equivalent means known in the art.

Figure 11A:
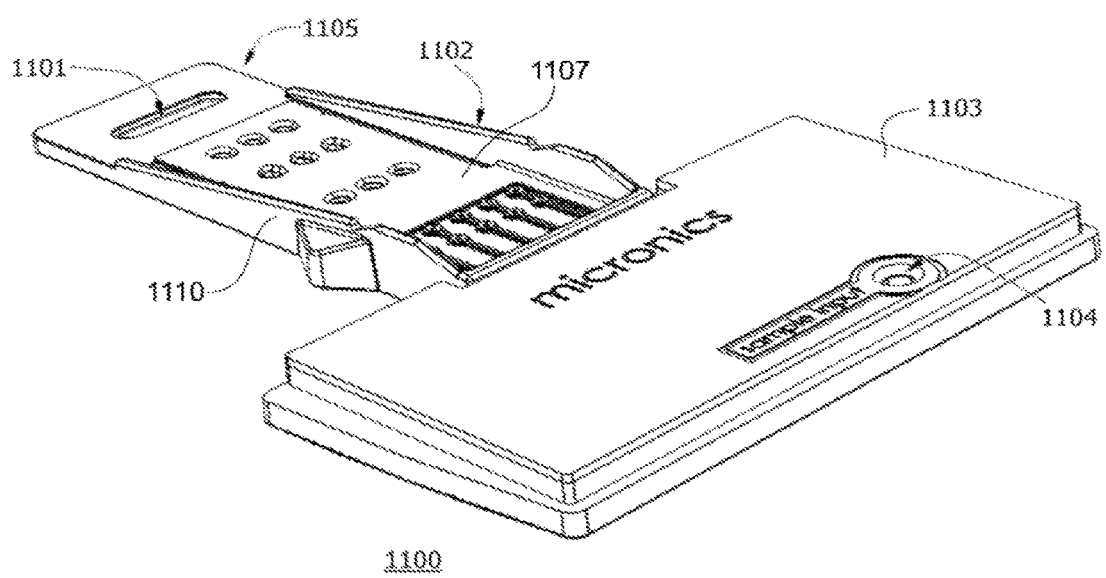
FIGS. 11A and 11B are perspective views of an insertable microassay cartridge for use with the detection system of the invention.
Figure 11B:
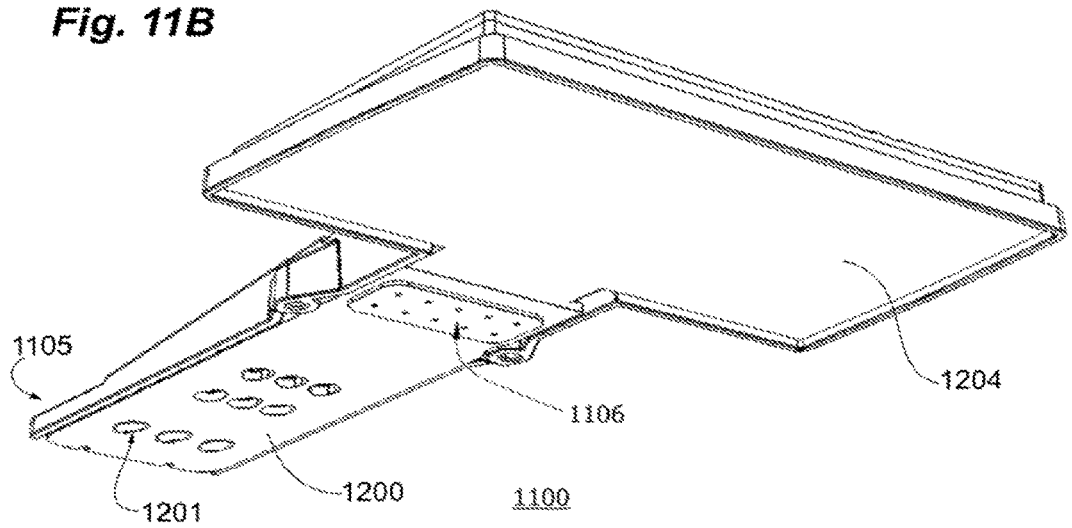

FIGS. 11A and 11B are perspective views of an insertable microassay cartridge 1100 for use with the apparatus of the invention. The cartridge shown here consists of a housing 1102 and coverplate 1103 with internal workings. Port 1104 is for receiving a liquid sample and anterior nose 1105 is for inserting into the docking bay of the host instrument. Window 1101 in the cartridge housing is an optical window formed over the sample wells 1201, as shown in FIG. 13. Gasket 1106 is for sealedly interfacing with the pneumatic interface multiport 350 of the host instrument. Shown from underneath is the inboard circuit card 1200 and the outboard circuit card 1204.

Pneumohydraulic Systems

Figure 12:
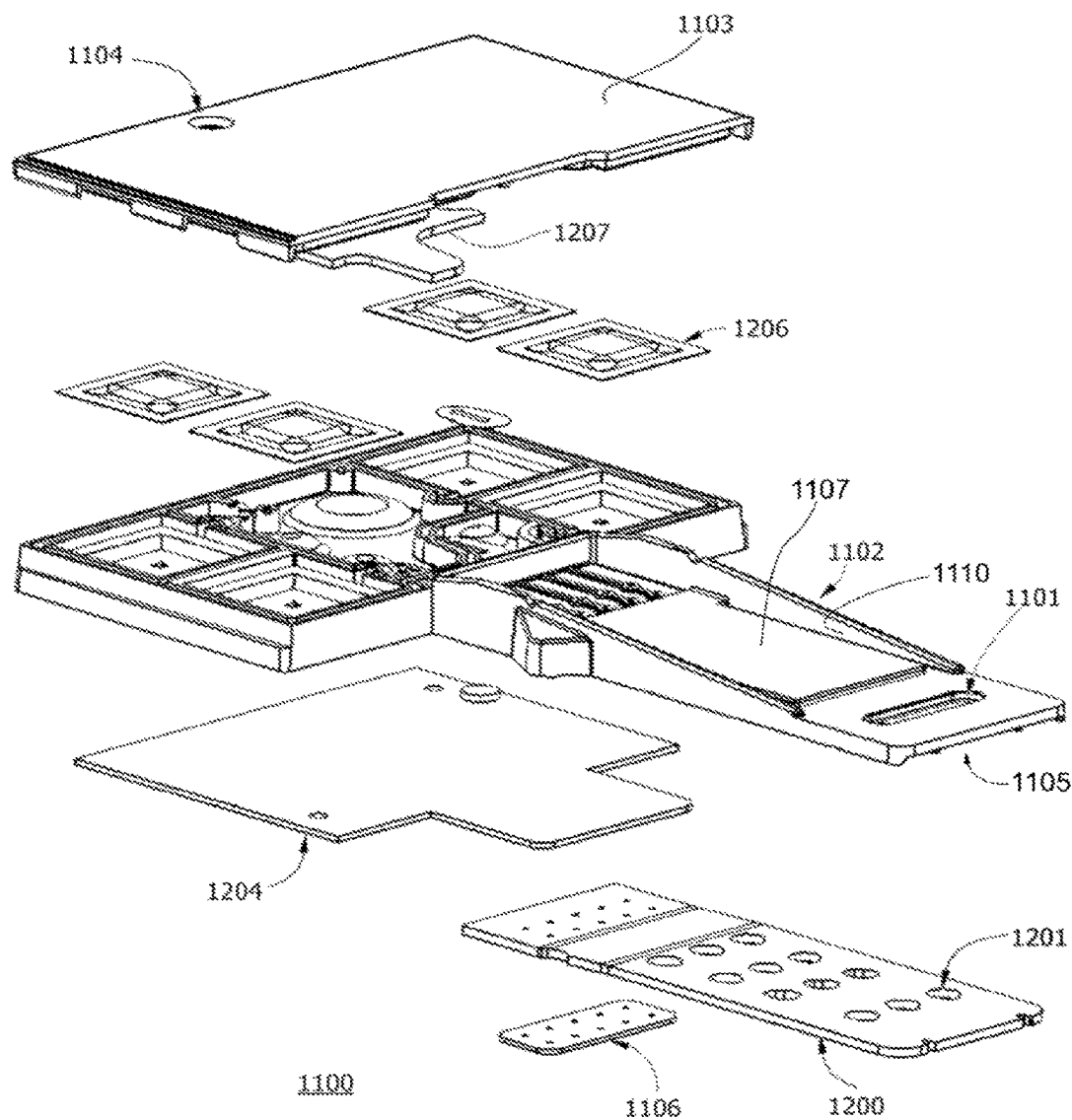
FIG. 12 is an exploded view showing the internal components of a microassay cartridge.

FIG. 12 is an exploded view showing the internal components of a microassay cartridge 1100. This particular cartridge 1100 is designed for PCR with FRET or molecular beacon detection. It is preferably left to the skill of the artisan to determine the details of the cartridge design and analytical reactions to be employed according to the diagnostic application and specific requirements to be met, and the following detailed description is supplied only for illustration.

Sample is added through inlet port 1104. An optical window 1101 on the nose of the housing nose 1105 inserts into the host instrument and is aligned so that the windows of the FRET or molecular beacon detection chambers 1201 of the microassay inboard circuit card 1200 are scanned by the detector head, which follows a linear path that transects the optical window longwise. Added processing related to sample preparation is supplied on outboard card 1204. All liquid reagents are enclosed in sealed rupturable pouches 1206 and are dispensed when needed under pneumatic control. Other reagents are provided on-card in dry form. Fluid waste is sequestered in an adsorbent batting 1207 that is sealed in place under the plastic coverplate 1103. The details of any particular biochemical or molecular microassay are beyond the present scope, but microassay circuit 1200 with internal microassay channels and wells for thermocycling and amplifying a nucleic acid target includes detection chambers 1201 for FRET detection of any resultant amplicon.

The pneumatic supply directed through 10 ports in gasket 1106 is fluidly connected to circuitry in both card 1200 and 1204. During initial sample processing in card 1204, pneumatic elements in card 1200 are actuated, but to no effect because the card is empty. Then when processed sample is transferred to card 1200 for analysis, pneumatic elements in card 1204 are actuated, but to no effect because the card is no longer needed. Serendipitously, this achieves multiplex valve logic without the need for extra pneumatic ports to control the two cards 1200, 1204 separately. Ten ports are found to be sufficient for most assays and are associated individually with separate pressures for pumps, valves, and vents, including both positive pressure and suction pressure, without the need for additional complexity and redundancy in the external pneumatics supply manifold contained in baseplate 330.

Figure 13A:
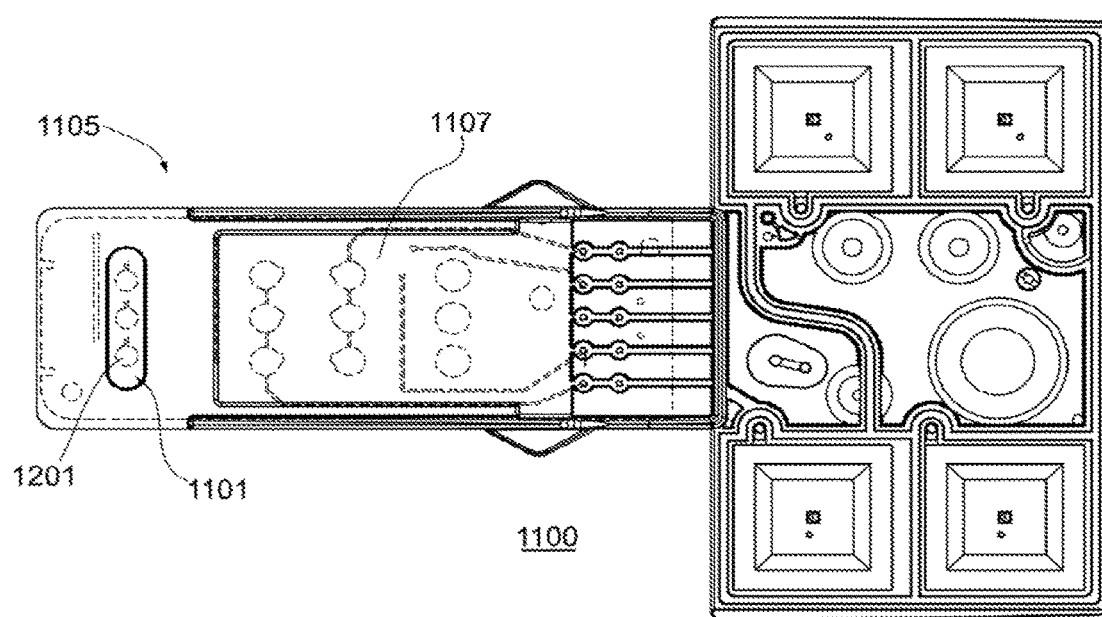
FIGS. 13A and 13B are plan and elevation views of an insertable microassay cartridge for use with the detection system of the invention.
Figure 13B:
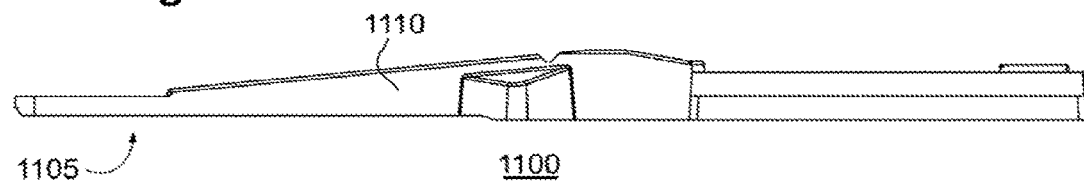

FIGS. 13A and 13B are plan and elevation views of an insertable microassay cartridge 1100 for use with the apparatus of the invention. Shown are optical windows 1101 on anterior nose 1105 of the cartridge (the nose inserts into the hose instrument and the optical windows are scanned by the detector optics). Also shown is platen surface 1107 for compressing the cartridge against heater assembly 340 and gasketed pneumatic control interface port 350.

Figure 14A:
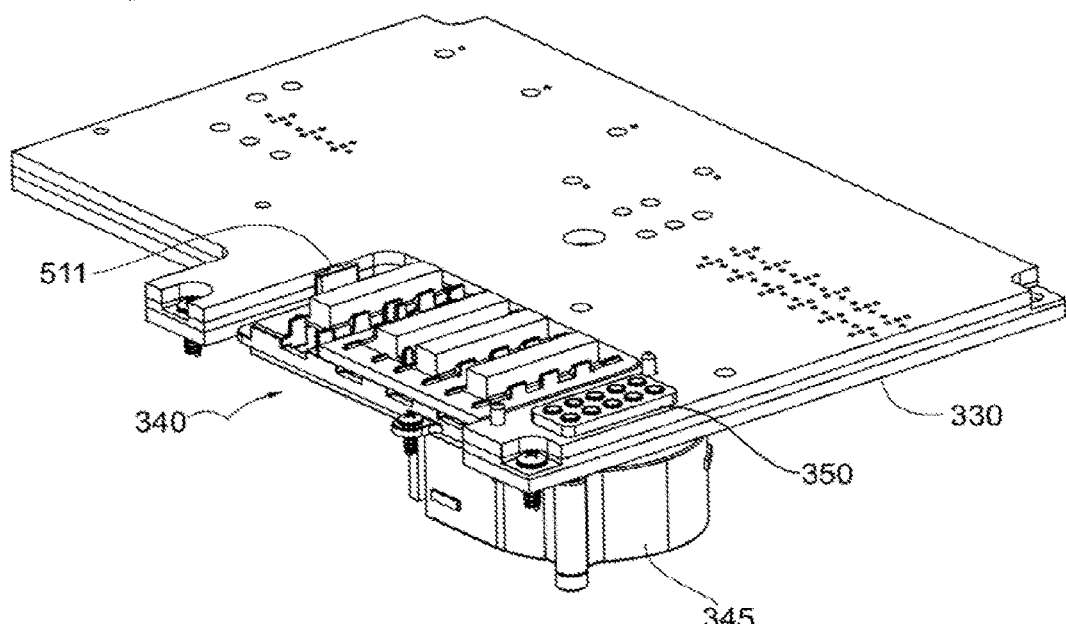
FIG. 14A isolates the mounting plate with internal pneumatic manifold, pneumatic interface multiport, and heater module.
Figure 14B:
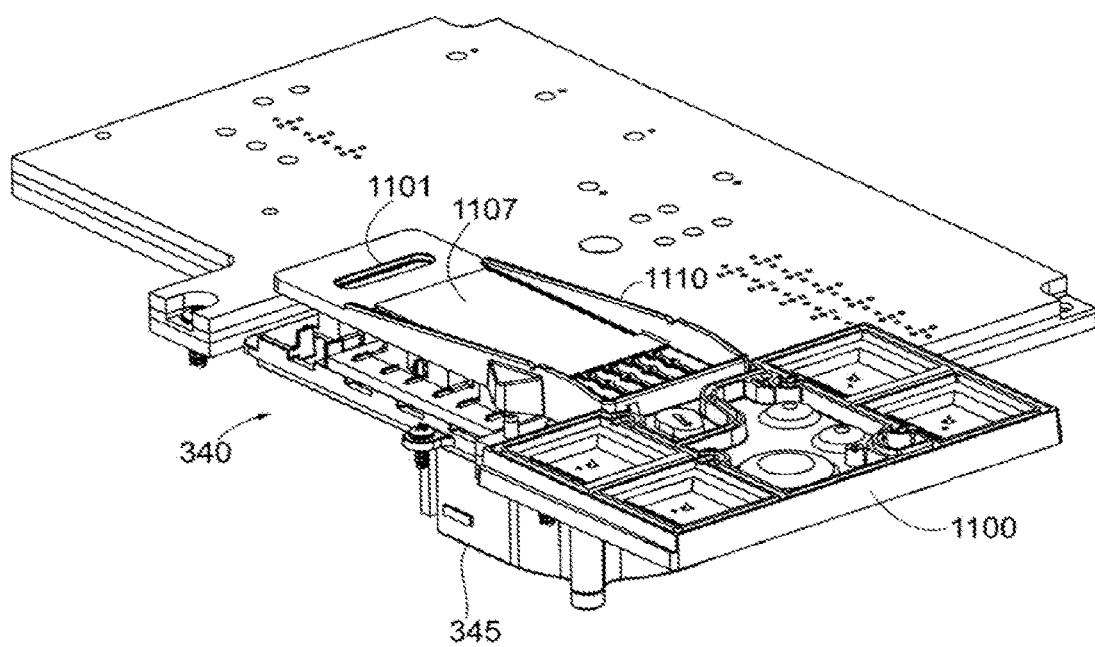
FIG. 14B depicts the position occupied by a microassay cartridge when in use.

The cartridge as shown is a disposable cartridge 1100 that inserts into a docking bay 103 in the host instrument when in use. Lateral ribs 1110 of the cartridge housing are for structural reinforcement and aid in the docking process. FIG. 14A is a perspective view of the inclined mounting plate 330 with enclosed, internal pneumatic manifold, heater module 340, and pneumatic interface multiport 350; FIG. 14B depicts the microassay cartridge when docked in the host instrument. In this view, the cartridge is fluidly engaged onto the pneumatic control interface multiport and is thermally contacted with the four zone heaters of heater module 340. Pressure on platen surface 1107 urges the cartridge against the thermal and pneumatic interfaces. The mounting plate includes an internal pneumatic control manifold that supplies regulated pneumatic pressure to the cartridge through the pneumatic interface multiport 350. In a complete instrument, mounting plate 330 is populated with pressure regulators, accumulators, and solenoids for controlling card pneumatics.

FIG. 15 is an exploded view of the nose 1105 of a microassay cartridge 1100, the nose containing the optical window 1101 and the inboard card member 1200.

Nested inboard 1200 and outboard circuit cards 1204 share a common pneumatic control interface (1111*a*, 1111*b*), aligning here with sealing gasket 1106, and share ports by fluidly connecting inputs through vias to both the inboard and outboard fluidic circuits. The outboard fluidic circuit in this case is responsible for sample preprocessing; the inboard circuit receives the preprocessed sample and analyzes it for a target analyte. Reduced interface complexity is achieved by multiplexing the pneumatic supply ports in the pneumatic interface between the inboard and outboard cards. The pneumatics may be used first for a fluidic operation in the outboard circuit, and then for a fluidic operation in the inboard circuit, a surprising solution to the problem of managing complex circuitry economically.

More generally, the pneumatic interface array comprises a plurality of pneumatic ports fluidly connected by vias fluidly joining a pneumatic circuit in a first circuit card to a pneumatic circuit in a second circuit card, such that the plurality of pneumatic ports are enabled to receive a plurality of pneumatic pulses applied according to programmable instructions and to multiplex those pneumatic pulses to fluidic circuit elements of the first circuit card and the second circuit card, thereby reducing the number of ports required to operate said first and said second hydraulic circuits. For example, a pneumatic pulse applied to the pneumatic interface at a first via forces processed liquid sample through the fluid junction from the outboard circuit card to the inboard circuit card, such as is useful when the first card is designed for extracting nucleic acid from a sample and the second card is designed for amplifying and detecting a molecular target, as will be described in more detail below.

Bosses 1108 have a narrow cross-section to limit unwanted heat transfer in the inboard card, and also serve to transfer compressive loading to a defined circumference around the larger pneumatic diaphragm members. Pin receiving holes 1109a, 1109b are used to align the cartridge in the docking bay 103 on pins 510a, 510b when loading a new cartridge into the host instrument.

The particular cartridge illustrated is designed for PCR with thermocycling and FRET detection. The outboard card 1204 is intended for isolating a nucleic acid fraction from a sample. Fluidic circuit card 1200 with internal channels and chambers (1115, 1116) for thermocycling, and amplifying a nucleic acid target includes sample wells 1201 for FRET detection of any resultant amplicon. Also depicted are chambers 1114 for cDNA synthesis. Three parallel assay channels are shown. Other circuit configurations may be used with the microassay detection system of the invention and the assays are not limited to three channels or to nucleic acid detection by PCR.

FIG. 16 is a plan view of the mounting plate 330 without microassay cartridge, showing the position of a sectional view through the pneumatic interface multiport 350. Also shown are alignment pins 510 for receiving the cartridge and the heater assembly 340. Other holes are ports intended for use in mounting pneumatic system components in fluidic communication with a pneumatic manifold extending through the mounting plate, which may be made of layered acrylic for example that has been fused by solvent welding or made by a process of three-dimensional printing.

Figure 17:
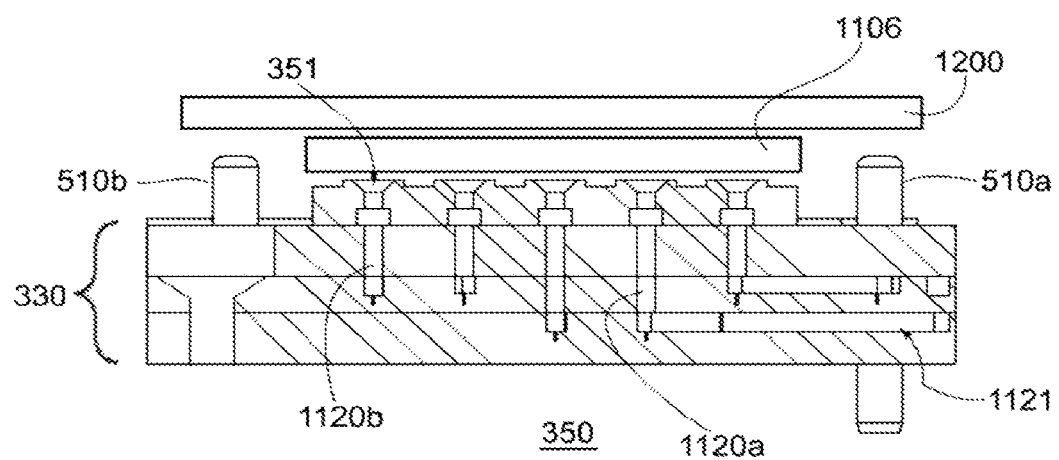
FIG. 17 is a cross-sectional view through the pneumatic interface multiport.

FIG. 17 is a sectional view through the pneumatic control interface 350 at the section cut in FIG. 16, showing ports for engaging vias (cf 1120a, 1120b) leading to pneumatic channels in the inboard card 1200. The ten ports 351 connect through the vias to the pneumatic manifold enclosed in mounting plate 330, of which pneumatic channel 1121 is representative. Also shown are cartridge registration pins 510a, 510b for seating the pneumatic interface port of the card against the card pneumatic control interface 350.

The card 1200 shown here in block outline has internal pneumatic workings which operate in response to pressurized gas pulses applied from the pneumatic distribution manifold 330 via pneumatic interface multiport 350. Internal pneumatic workings in the card include a valve tree operable under control of valve logic supplied by the host controller, diaphragm pumps for moving fluids through the circuitry, and fluid reservoirs for dispensing fluids under pneumatic control. The need for multiple ports relates to the way in which valve logic is laid out on the card and the need for multiple pressures. Pneumatic supply at both a positive and a negative pressure is generally needed, and several intermediate pressure levels have been found to be advantageous. Pressures that have been found to be useful include +10 psig for operating pumps, −5 psig for opening valves (such as the diaphragm valves described in WO Publ. No. 2002/081934), and zero pressure vents, while not limited thereto. As shown here, as many as ten pneumatic interconnects with the cartridge may be engaged. Depending on the complexity of the cartridge, fewer or more ports may be used by resizing or reconfiguring the pneumatic interface if desired.

Separating the pneumatic channels of the microassay cartridge 1100 and the corresponding ports of the pneumatic manifold 350 is a silicon rubber gasket 1106, or a generally compliant elastomeric gasket, which seals the pneumatic interconnections under compression when the cartridge is loaded in the instrument and spring pressure is applied. Gasket 1106 serves as a single-use sealing gasket and is advantageously supplied with the disposable cartridge, not as part of the instrument as per conventional wisdom. By including the gasket with the disposable cartridge 1100, a better and cleaner seal at the pneumatic interface is obtained and the need to periodically replace the gasket is eliminated. Gaskets are generally formed of silicone rubber or other compliant material.

Using the pneumatic circuits of the invention, the circuitry may also be multiplexed by supplying multiple pneumatic sources in the host instrument, where pneumatic supply circuits in the connecting manifold 350 may be switched from one pneumatic pressure to another, such as from a positive pressure to a negative pressure, without the need for additional pneumatic circuits. Thus each manifold subcircuit in the baseplate 350 may be operated at a plurality of pressure states. In this way it is possible to multiplex distribution of stronger pneumatic "states" to circuit elements operative with a stronger pneumatic pressure and weaker pneumatic states to circuit elements operative with a weaker pneumatic pressure via a common pneumatic interface port array. Analogously, it is possible to multiplex distribution of stronger pneumatic "states" to circuit elements operative with a stronger pneumatic pressure and vacuum pneumatic states to circuit elements operative with a vacuum pressure card via a common pneumatic interface port array. By joining a first circuit card and second circuit card with a common pneumatic interface, dual functionality of the pneumatic circuitry is achieved.

Pressure states are generally selected from a range of positive and negative pressures, including while not limiting to −5 psi, +10 psi, +12 psi, +15 psi, +20 psi, +7 psi, and 0 psi, where higher pressures are used for rupturing reagent packs, for example, and negative pressure are used for opening valves, and so forth. These pressures may be supplied from buffered pressure reservoirs. Dial up variable pressure supplies may also be used. The pneumatic states are supplied to the cartridge through manifold subcircuits under microprocessor control. Each assay consists of a series of steps to be executed according to pneumatic valve and pump logic needed to move the fluid through the hydraulic circuitry. Vents are also a necessary part of the circuit and pressurizing, reversing pressure, and venting are all within the capacity of the instrument and associated microassay circuitry according to the requirements of each individual assay type.

Figure 18:
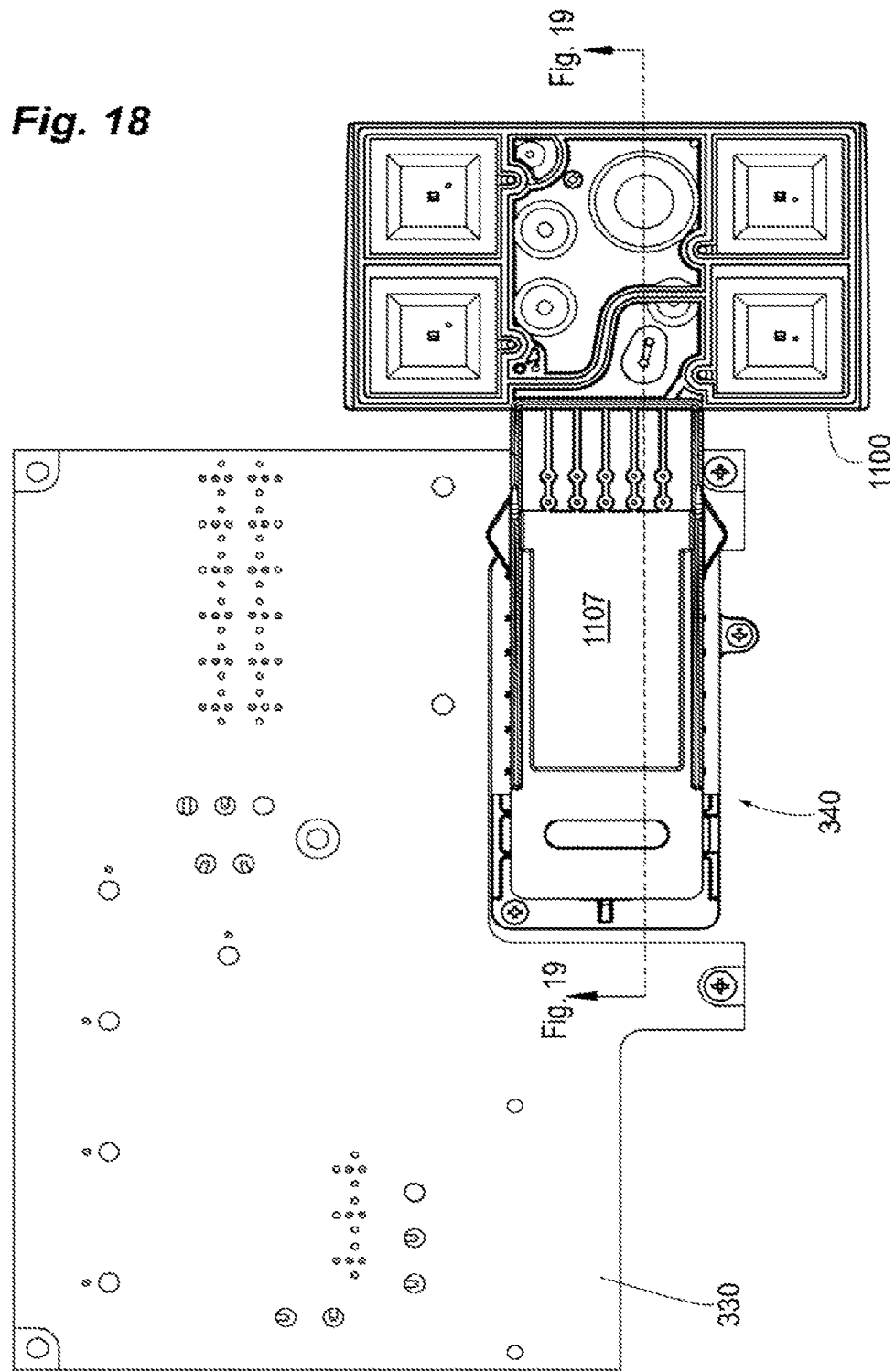
FIG. 18 is a plan view of the mounting plate with microassay cartridge, showing the position of a sectional view through the cartridge and heater module.

FIG. 18 is a plan view of the mounting plate 330 with superimposed cartridge 1100 in position for use (heater module 340 and pneumatic interface 350 contacting the underside of microassay cartridge 1100 are under the cartridge); showing the position of a sectional view cut through the cartridge and heater module.

Temperature Control Systems

Figure 19:
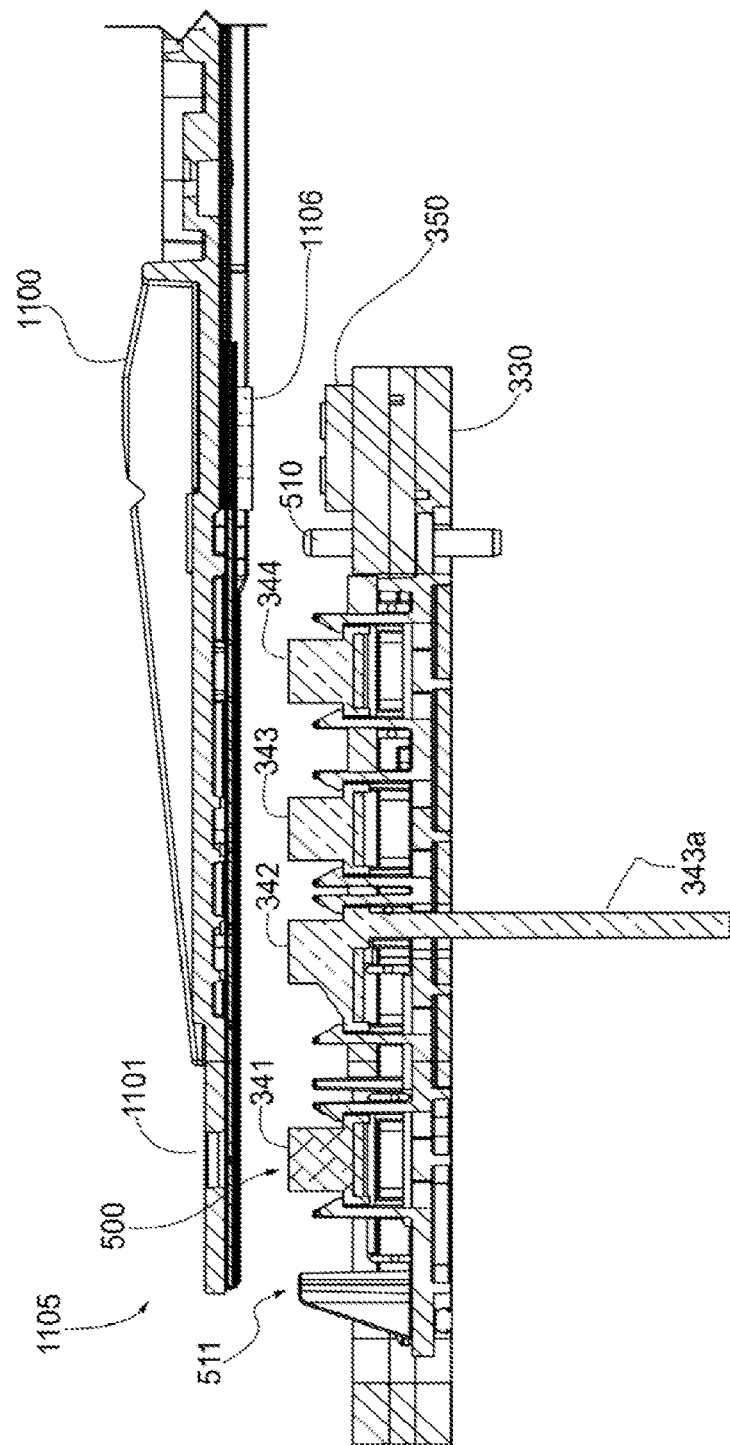
FIG. 19 is a cross-sectional view through the heating manifold and microassay cartridge.

FIG. 19 is a view of the heater module and the nose 1105 of cartridge 1100 in section, referencing the cross-section position marked on FIG. 18. The cartridge is raised above heating blocks 341-344 for purposes of labeling. The pneumatic interconnect module 350 (two rows of ports are indicated) engages disposable gasket 1106 of the cartridge, which was described functionally with reference to FIGS. 17 and 15. Also shown are four resistive zone heating blocks (341, 342, 343, 344) configured to contact individual chambers of the nucleic acid amplification circuit. Paired registration pins 510 align the cartridge housing so that the thermal surfaces of the blocks properly engage the fluidics. Step 511 supports the nose 1105 of the cartridge.

Zone heating block 341 is a thermo-optical interface and comprises a mirror face 500 contacting the fluidic circuit member. An optical window 1101 in the cartridge housing aligns with the mirror face and the detector head slides along rail 308, 309 (FIG. 4) so that the objective lens assembly 315 of the detector head 311 runs down the middle of the long axis of heating block 341. Detection wells in the circuit are positioned to line up on the thermal block and mirror face under the optical window.

Block 341 is temperature controlled for FRET determinations. Resistive heating block 342 is adjusted to a double stranded nucleic acid denaturing temperature before the assay is started, and block 343 is set to an annealing temperature. The annealing block 343 is provided with a cooling fin 343a and a blower 345 so that hot fluid conveyed from the denaturing chambers can be rapidly cooled, thus speeding the thermocycling time. Block 344 is used for cDNA synthesis if needed.

The fluidic circuit may include a pair of fluid chambers overlying heating blocks 342 and 343. The paired chambers include pneumatically actuated diaphragms operated cooperatively as described in U.S. Pat. Nos. 7,955,836 and 7,763,453 (which are co-assigned) for reciprocating fluid flow between the denaturing and annealing temperatures as is useful for amplification of nucleic acids by thermocycling. Each heating block is spring loaded and presses against the underside of the fluidic circuit. The springs shown here are wire springs chosen for their compactness.

FIG. 20 is an exploded view of the heater module. Four heating blocks are shown, each block associating with a printed circuit strip 347 having resistive heating elements (347a) and a centrally positioned thermistor (347b), the resistive heaters being under PID-type feedback loop control. Supporting circuitry on the printed circuit is rendered schematically and is controlled from the host controller.

Each block floats on a spring support 348 and is provided with compliant electrical connections to move freely in a limited vertical range. The blocks are thermally insulated for each other by an insulator jacket 346 with cut-out pockets. The heating blocks are clipped into slots formed in a supporting mounting plate 349. The wire springs 348 are configured to urge the block against the compliant plastic undersurface of the card 1200 (FIG. 15) with a mild force to decrease resistance to heat transfer.

Figure 21:
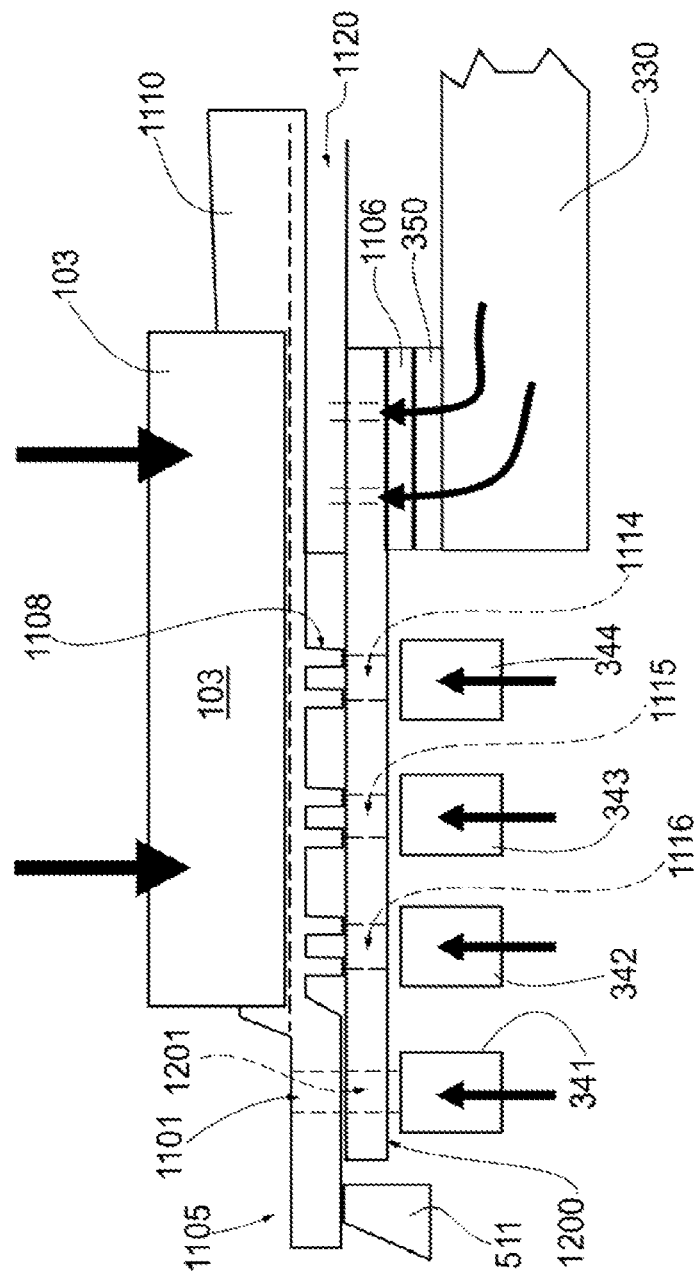
FIG. 21 is a schematic of spring forces exerted on the cartridge in the docking bay.

FIG. 21 is a schematic depicting the balance of clamping and spring forces responsible for thermal contact between the cartridge and the heating blocks. As shown with reference to FIGS. 5 through 10, the docking bay 103 of floating stage 301 is mounted with a 4-point suspension 600 such that springs mounted on each of four corner posts (601, 602, 603, 604) are biased to press down on the cartridge once the cartridge has been seated. The clamping mechanism 800 is worm gear driven and squeezes the cartridge against registration pins 510 and step 511 in the heater module. Each heating block is a floating member which is urged upward against the undersurface of the inboard circuit card by independent spring members under each block. Wire springs mounted in the heater module press the blocks up against the underside of the inboard fluidic member 1200 and gasket 1106 to seal the card pneumatic interface against multiport 350 mounted on the pneumatic distribution manifold 330. In this way, the cartridge is locked in place by the stronger suspension springs of the clamping assembly and the heating blocks are thermally contacted with the inboard card by weaker springs of the heater module assembly, requiring less precision in manufacturing. The cartridge is sandwiched in the docking bay by the two opposing spring forces. Lateral reinforcing ribs 1110 strengthen the cartridge; ensuring that the more pliant the inboard circuit cards are in thermal contact with the heating members. The downward spring suspension force is about 5 psi and upward spring force is about 1 psi across the surface of the heating member, the springs acting cooperatively to clamp the cartridge and to press the heating blocks against the undersurface of the inboard card where heating is intended. Also shown for illustration are card 1200 features including cDNA well 1114, annealing well 1115, denaturing well 1116, and detection well 1201 aligned under optical window 1101.

Also shown in FIG. 21, bosses 1108 are formed on the inside surface of the cartridge housing abutting the fluidic chambers. The bosses concentrate the spring loading forces around fluidic diaphragm elements where compression is needed to ensure low thermal resistance between the fluid contents of the circuit and the underlying heating blocks. These bosses 1108 are configured for low thermal cross-section and are formed by removing mass from the housing that would otherwise increase parasitic heat losses and thermal capacitance around the cDNA synthesis and thermocycling chambers. Low thermal cross-sections are also presented laterally because the inboard fluidic member is suspended under the cartridge housing with an air gap above the amplification circuits, thus reducing conductive heat losses and thermal crosstalk between the zone heaters. An insulative jacket 346 inserted between the heating blocks is also used to isolate and maintain each thermal zone at the correct temperature and avoid convective thermal crosstalk between the resistive heating elements.

Figure 22:
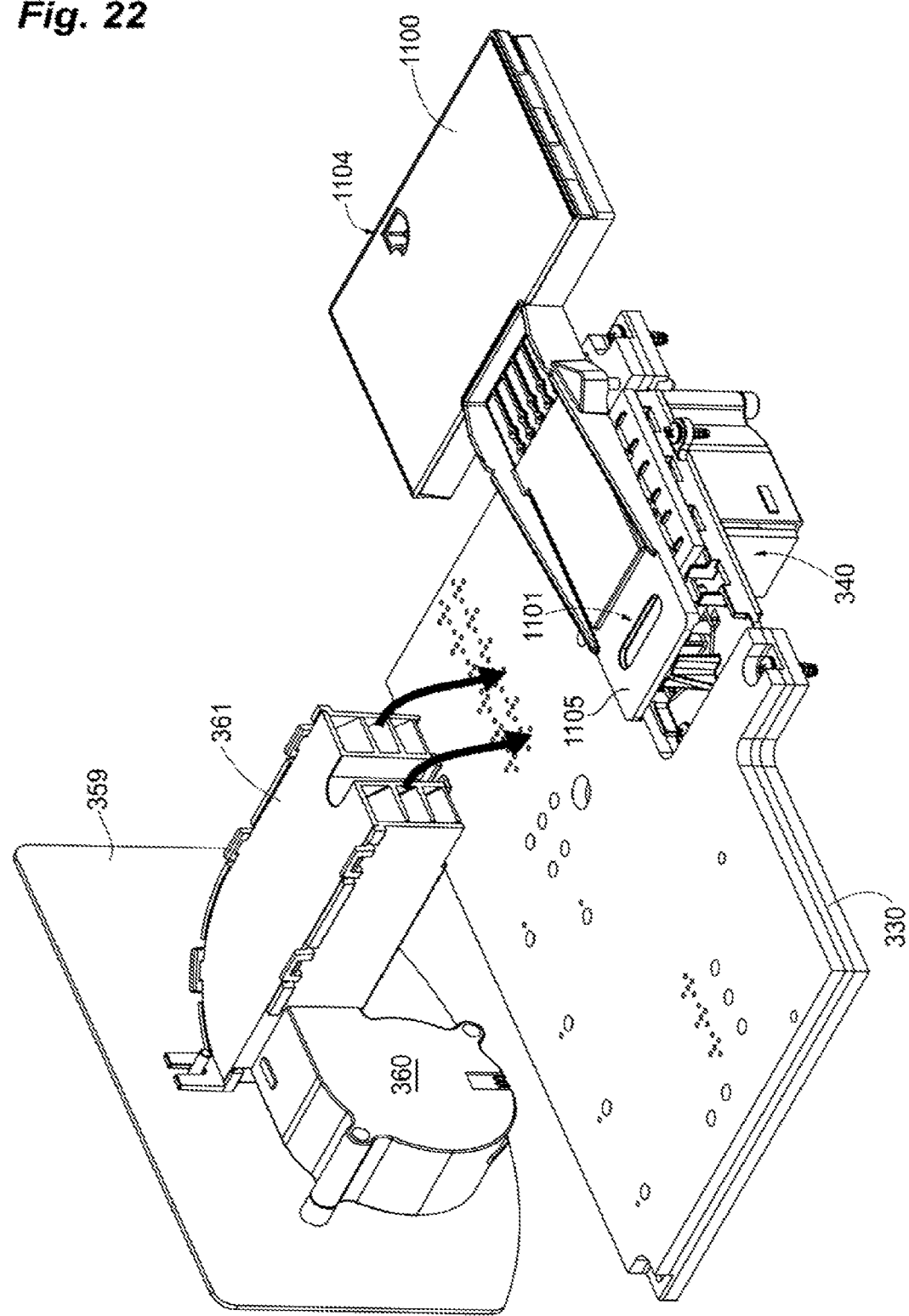
FIG. 22 is a partial assembly of the apparatus showing a case-mounted blower with fan outlet directed at the nose of the cartridge and heater module.

The nose 1105 of the microassay cartridge containing the sample wells is also formed to be thin to avoid excess thermal mass. A blower 360 shown in FIG. 22 is directed via baffled duct 361 onto the nose of the cartridge and is useful for FRET determinations. In FRET, a molecular beacon is mixed with single stranded amplicons in a detection chamber at a temperature above the melting temperature of the target analyte species. The temperature is then reduced using forced cool air while fluorescent emissions are collected. The blower is mounted on an external wall 359 of the instrument chassis.

In one illustrative embodiment, as the mixture cools, molecular beacon anneals to the target sequences, quenching fluorescence in the probe. Real time monitoring of the fluorescence results in a melt curve that can be used to validate the identity of the target amplicons. To perform the test, zone heater 341 is brought to a temperature above the melting point of the target species, the heater is turned off and blower 360 is turned on and is directed at nose 1105 of the cartridge around and underneath the optical window 1101. Temperature in the reaction mixture and fluorescence are monitored. Temperature falls very rapidly in response to the circulating air while changes in fluorescence are optically monitored, allowing replicate FRET determinations to be rapidly performed on each sample well.

Thus in one embodiment, the invention is a method for performing a FRET melt curve determination, comprising a) heating a sample chamber containing a FRET probe and a target nucleic acid sequence to a temperature above the melt temperature of the duplex probe; b) turning off said heating; and, c) using a shielded detector head having an autonomous ODAP daemon, scanning the detector head across a sample chamber while monitoring a change in fluorescence of the FRET probe in response to a change in temperature of the sample chamber caused by turning on a fan and directing a stream of ambient air onto the sample chamber, thereby rapidly cooling said sample chamber while monitoring fluorescence. Analysis of the derivative of fluorescence intensity as a function of temperature yields a melting point characteristic of the amplicon of interest. It has proved possible to make these determinations in less than a minute using the low thermal mass of the cartridges of the invention. The heating block 341 may be provided with a cooling fin and independently air cooled to accelerate the measurement, if desired, but generally this has not been needed.

Optical Systems

Figure 23:
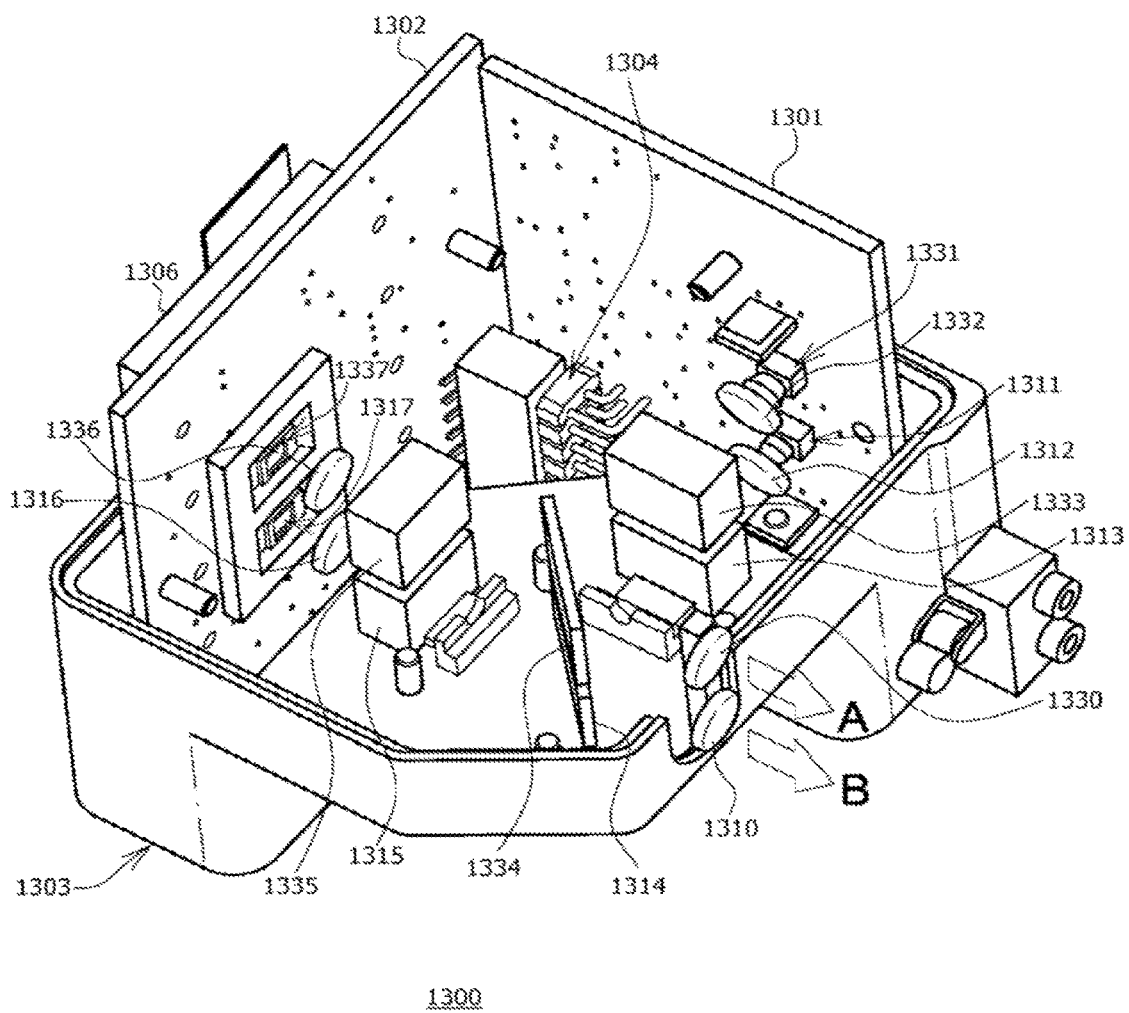
FIG. 23 is a perspective view of a detector head with dual optical channels and electronically isolated circuit boards for excitation and emissions detection. One half of the housing is removed in order to view the internal components.

FIG. 23 is a perspective view of a dual channel detector head 1300 with two optical channels and electronically isolated circuit boards (1301,1302) for excitation and for emissions detection respectively. In this view, the upper half of the housing 1303 is removed in order to show the internal components of the detector head. The dual channels are marked by objective lenses (1310, 1330) and optic pathways A and B (open arrows marked A and B). The SMD LED excitation light sources (1311, 1331) are mounted on a source LED printed circuit board (1301), which is connected at right angles to sensor PCB (1302) via an edge-type resistive pin-connector (1304). The photodetection components are mounted on the sensor PCB (1302). A Faraday cage element (1306) is used to shield the photodiodes (1317) and (1337) and surrounding high gain amplification circuitry.

Fluorescent excitation is provided in the target channel (Arrow A) by a surface mounted LED (1331) which is chosen to match the excitation spectrum of the target fluorophore. Source LED (1331) emits a divergent light beam, and the radiated light beam is then collimated by source excitation lens (1332). Source lens (1332) is a planoconvex lens having its flat surface facing the LED. The collimated light beam may then be passed through an excitation bandpass filter (1333), the purpose of which is further explained in the description associated with FIG. 20. The collimated, filtered excitation light beam is then reflected from a dichroic mirror element or beamsplitter (1334), which is installed at a forty-five degree angle to the incident beam, and is passed through a planoconvex objective lens (1330) and through an external window in the detector housing (Arrow A). After passing lens 1330, the excitation light is focused through a detection chamber (not shown, see FIGS. 14-17) embedded in a microassay cartridge, which contains a sample liquid with any target fluorophore. The path length of the excitation light through the sample liquid is doubled by use of a back mirror behind the microassay cartridge. The target fluorophore is excited by the incident light beam. The emission of the fluorophore is generally at a longer wavelength than the excitation wavelength and is shifted by an amount equal to the Stokes shift of the target fluorophore.

A portion of the returning emission from the target fluorophore in the detection chamber is collected by planoconvex sampling lens 1330 and is collimated before striking dichroic mirror 1334. Optionally, a Fresnel lens may be use to further reduce the working distance between the lens and the sample to optimize collection of emitted light, which is further enhanced by back mirror mounted on a heating block behind the detection chamber. Because dichroic beamsplitter 1334 has a wavelength cutoff between the excitation and emission wavelength, the dichroic mirror 1334 now acts as a pass-band beam splitter for the emitted fluorescent light beam and a stopband filter for the excitation light. It transmits the emitted fluorescent light while reflecting reflected excitation light and any ambient light entering the light path through the objective lens window. Emitted light passing through the dichroic beamsplitter 1334 then passes through an emission filter 1335, the purpose of which is further explained in the description associated with FIG. 20. Light exiting emission filter 1335 then passes through planoconvex sensor lens 1336, where it is focused onto the surface of a photosensor 1337 which is surface mounted to PCB 1302 and is protected from electrical noise by Faraday cage 1306.

The above described optical pathways are repeated in a second (control) channel having control excitation LED 1311, planoconvex excitation lens 1312, excitation filter 1313, dichroic beamsplitter 1314, objective lens 1310, control emission filter 1315, planoconvex sensor lens 1316, and control photodiode 1317. Outputs from both photodiodes are amplified by three-stage trans-impedance amplifiers built into the board next to the photodiodes and grounded to an embedded microprocessor on the sensor PCB via carefully shielded pins from the amplifiers.

In one embodiment, as exemplified by the use of fluorescein and Texas Red as fluorophores, excitation LED 1331 is a 470 nm LED with band-pass excitation filter 1333 for delivering essentially monochromatic light of 485±12 nm used for the target channel and a 590 nm LED 1311 with band pass filter 1313 was used for the control channel. The excitation LEDs are modulated or "strobed" on and off using a strobe rate of 130 Hz to filter AC power-related noise at 50 or 60 Hz and at harmonic frequencies associated with fluorescent overhead illumination, also filtering phantom signal related to stray ambient light and electrical noise that may be present at 30 or 60 Hz. Local feedback sensors are used to monitor and stabilize source LED output intensity. Detection monitoring of fluorophore emission is coordinated with movement on rails of the detector head under power of a stepper motor controlled by a host controller. An embedded microprocessor and associated circuitry in the detector head is provided with RAM memory, ROM memory, an A-D converter, a three-stage trans-impedance amplifier, and signal processing and command sequence firmware to handle these functions.

Each of the photo-sensors 1317 and 1337 are mounted on a common PCB 1302. The output signal legs from each of these photo-sensors are connected directly to a pre-amp or first stage of respective tri-stage trans-impedance amplifiers (not shown). PCB 1302 makes extensive use of hardware noise-reduction components, in particular an embedded ground plane and a Faraday Cage 1306 to minimize the unwanted effects of any RF or electromagnetic interference on the input signals. The amplifier is shielded from electronic noise by a Faraday cage, a bypass capacitor, a signal conditioning pre-amplifier, a separate ground plane, a metallized detector head housing, or a combination thereof, and the amplifier is in close electrical proximity to the sensor. Optical signal acquisition, preconditioning, amplification and digitization is controlled by an autonomous daemon operating in a shielded environment. The combination of these hardware noise-reduction elements with optical data acquisition, digitization and processing method under local control in the detection head, leads to a detector design which is essentially immune from the effects of unwanted noise. The tri-stage amplifier may be configured for a gain of up to $10^{14}$, and is selectably configured for gain of $10^2$, $10^3$, $10^6$, $10^{10}$, or $10^{12}$, as desired.

Figure 24A:
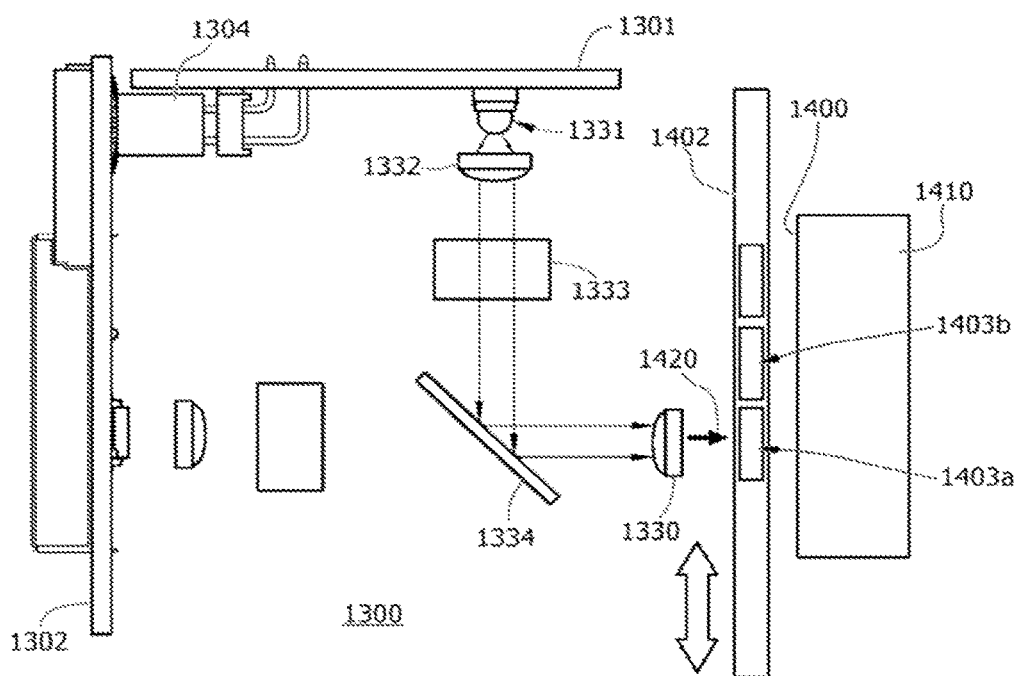
FIGS. 24A and 24B are schematic views of the internal optical components of a fluorescence detector with dual optical channels, heating block-mounted mirror and microfluidic cartridge. Excitation optics are mounted on one circuit board and detection optics on another to reduce noise interference.
Figure 24B:
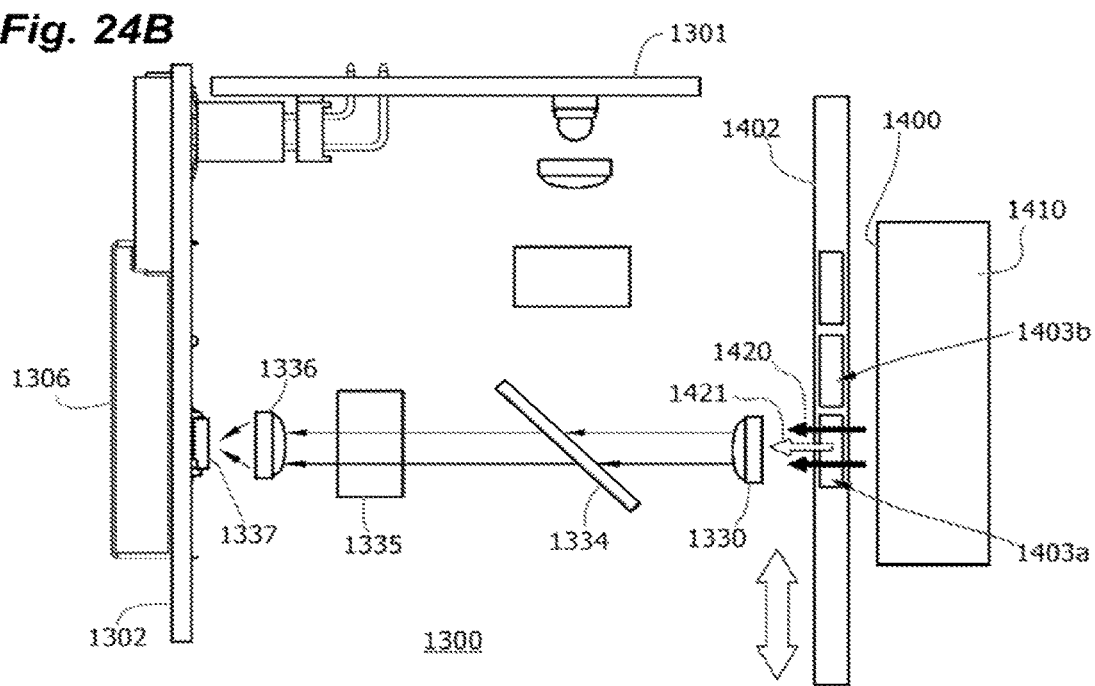

We have surprisingly found that packaging of signal processing in the scanning head achieves an isolated, low noise environment with improved signal-to-noise ratio and sensitivity by minimizing signal pathlengths and permitting effective use of Faraday shielding where necessary, such as around the sensor diode leads and at the junction between the excitation and sensor circuit boards. Optionally the detector housing may be fabricated from aluminum or coated with a conductive polymer and grounded to further shield the internal electronics from unwanted interference. Advantageously, higher signal amplification is realized in this environment, FIGS. 24A and 24B are schematic views of the internal optical components of a fluorescence detector head 1300, showing the external optical interface with optical windows in a microassay cartridge 1402 and back mirror 1400 mounted behind the cartridge on the surface of a heating block 1410 that is used to control or ramp the temperature in detection chambers enclosed in the cartridge. Unconventionally, multiple independent optic pathways or "channels" are formed in a single detection head and share electronic PCBs and downstream signal processing circuitry, but excitation optics are mounted on one circuit board and detection optics on another to reduce noise interference. The two boards are electrically coupled by a corner mounted pin junction 1304 and are electronically isolated using bypass capacitors mounted on separate ground planes.

Shown in FIG. 24A is the optical transition for the excitation of a fluorophore in a detection or sample well (1403a or 1403b) embedded within a microassay cartridge 1402. The head is a scanning head and moves across microassay cartridge 1402 (double arrow). Light from excitation LED 1331 on PCB 1301 is collimated by lens 1332 and made essentially monochromatic by band-pass filter 1333. Any fluorophore or fluorophores in detection well 1403a (whether the control or the target fluorophore) are excited by incident light 1420 focused on the sample by objective lens 1330. In FIG. 24B, the emission of the fluorophore(s) is collected by objective lens 1330 and transmitted to sensor 1337 after passing through dichroic beamsplitter 1334, emission filter 1335 and sensor lens 1336. Sensor 1337 is in direct electrical contact with the base of a high gain transistor that amplifies the output signal and is shielded in a Faraday cage 1306. The emitted fluorescent light is generally at a longer wavelength according to the Stokes shift of the fluorophore, enabling the emitted light to pass through dichroic bandpass mirror 1334 and emission band-pass filter 1335 without losses. Mirror face 1400 is used to increase the amount of excitation light on the target, doubling the excitation path length, and to improve emission collection efficiency. The light returned from sample chamber 1403a to objective lens 1330 is thus a mixture of emitted and reflected fluorescence 1421 and reflected excitation light 1420. Light traps (not shown) are provided to capture stray reflections. Reflected light 1420 does not pass dichroic mirror 1334 and is returned to the source, and does not interfere with the measurement of emission intensity at sensor 1337. The optic elements of a single channel, including excitation source, source collimating lens, excitation filter, dichroic mirror, objective lens, excitation filter, sensor lens, and detector with amplifier make up an optics module having an essentially monochromatic source wavelength and a highly specific sensor for detecting fluorescence at a particular wavelength characteristic of the target (or control) fluorophore. One optics module or channel may be used for an assay target, the other module for a control channel. Tandem mounted optics channels may be used to collect data on a plurality of fluorophores, where electrical processing is multiplexed through an embedded microprocessor under control of a resident daemon before transmission to the host instrument. As shown, each of the two channels shares circuitry on each of the two circuit boards, but has separate optics. Optionally, additional channels may be incorporated into the detector head by a process of duplication of the optical elements shown.

The microassay cartridge 1402 is movable (double arrow) relative to detector head 1300 and motorization of the detector head or cartridge tray or mounting chassis permits scanning: a transect across cartridge 1402 permits measurements to be made on sample chambers 1403a and 1403b, for example. By using multiple detection optics modules mounted side-by-side in a detector head, the sample chambers can be scanned for multiple fluorophores in series.

According to one embodiment, the excitation electronics are mounted on a printed circuit board (1301) and the detection electronics are mounted on a second PCB (1302). An edge-connector 1304 electrically joins the boards. Faraday cage 1306 protects the sensor and associated high gain amplifier from stray electromagnetic noise. Mirror 1400 is fabricated on the upper surface of heating block 1410, which also functions in heat transfer and controls the temperature of the sample fluid during the assay. The temperature of heating block 1410 can be ramped during scanning, for example as in a FRET melt determination with temperature and motor functions under control of the host controller while optical data is acquired by the embedded processor in the detection head in an autonomous process.

Figure 25A:
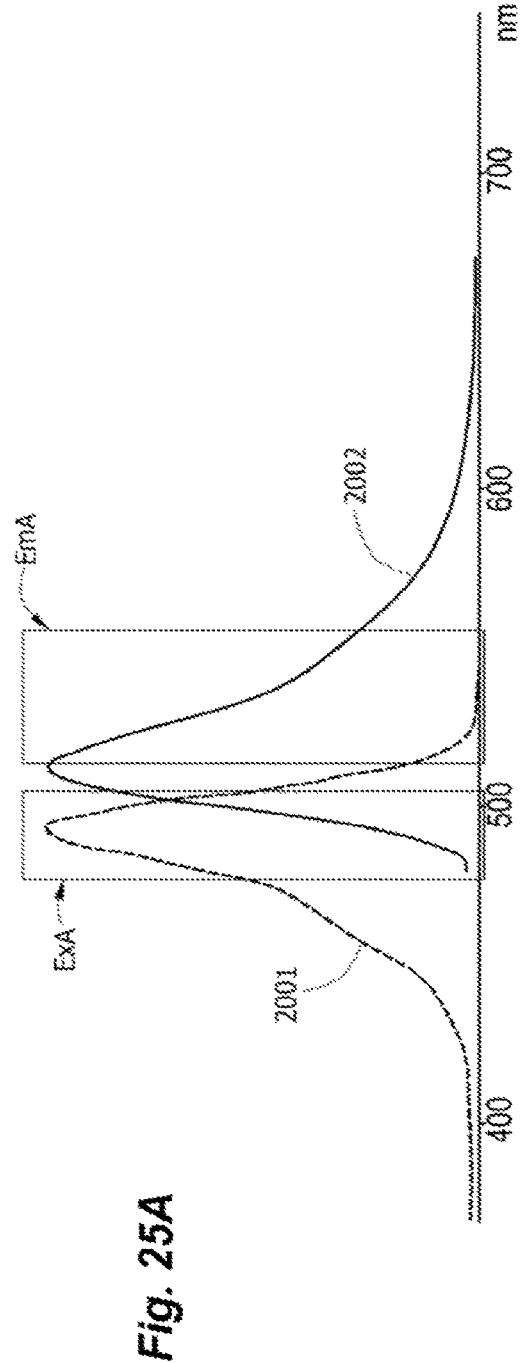
FIGS. 25A and 25B show emission and excitation wavelengths for two fluorophores in a liquid sample, and illustrate dual head optical isolation for removal of crosstalk.
Figure 25B:
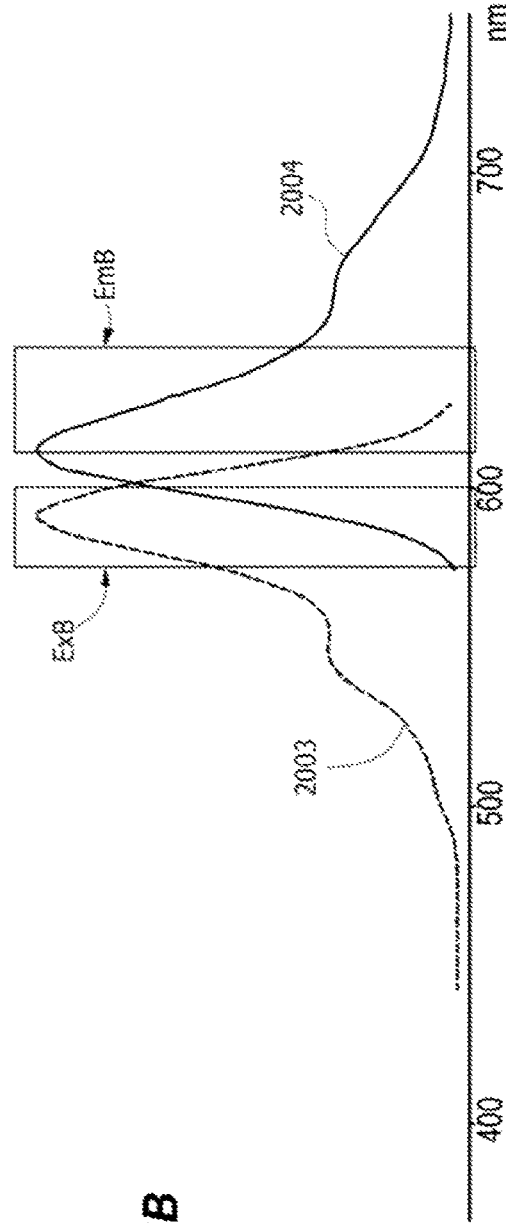

FIGS. 25A and 25B show the excitation and emission spectra of a typical system of mixed fluorophores for the target and control, here illustrated by fluorescein and Texas Red. Shown in FIG. 25A, curve 2001 is the excitation spectrum for fluorescein (dashed line); curve 2002 is the emission spectrum (solid). Shown in FIG. 25B, curve 2003 is the excitation spectrum for Texas Red (dashed line); curve 2004 is the corresponding emission spectrum (solid). Here control is Channel B (FIG. 25B) and target is Channel A (FIG. 25A), but the assignment is arbitrary.

Boxed area ExA indicates the wavelength band that is allowed to pass through the target excitation bandpass filter 1333. Box EmA indicates the emission pass band that is allowed to pass through the target emission bandpass filter 1335. Box ExB indicates the wavelength band that is allowed to pass through the control excitation bandpass filter 1313. Box EmB indicates the emission pass band that is allowed to pass through the control emission bandpass filter 1315. The boxes indicate the presence of stopbands on either side of the maxima. It can be seen from FIGS. 25A and 25B that, given the spectra for these two fluorophores and optical filters having the passband characteristics configured as shown, the following error conditions are corrected: a) Long wavelength excitation light from the target LED 1331 (greater than the wavelength of the LED peak excitation) cannot be mistakenly confused for target fluorescent emission, due to these longer wavelengths being cut off by the LED excitation filter 1333; b) Long wavelength excitation light from the control LED 1311 (greater than the wavelength of the LED peak excitation) cannot be mistakenly confused for control fluorescent emission, due to these longer wavelengths being cut off by the LED excitation filter 1313; c) Target fluorescent emissions cannot be inadvertently triggered by the (excitation filtered) control LED 1311. This error condition would otherwise lead to the control photosensor 1317 receiving unwanted contemporaneous signals from both the target and control fluorophores; and d) Control fluorescent emissions cannot be inadvertently triggered by the (excitation filtered) target LED 1331. This error condition would otherwise lead to the target photosensor 1337 receiving unwanted contemporaneous signals from both the target and control fluorophores.

Assay Validation

Serendipitously, the autonomous detector head functions can be multiplexed in dual head and multi-head detectors containing separate optical channels for detection of individual fluorophores, such that each channel comprises an LED for irradiating excitation light, at least one lightpath having an excitation filter, emission filter, dichroic mirror tuned to enable the detection of emissions from a fluorophore in a defined passband, an objective lens for condensing said excitation light and for collecting said emissions, a sensor for receiving any passband emissions, and a high gain amplifier for amplifying the output from the sensor, wherein each LED is configured to irradiate light in a frequency range so that the irradiation frequencies of the channels do not overlap, each optical channel is configured so that the emission passbands of the channels do not overlap; and the outputs of said amplifiers of said plurality of channels are multiplexedly digitized and tabulated in volatile memory under control of an autonomous daemon resident in firmware executed by a microprocessor embedded within the detector head.

For assay validation, two sensor channels (or more) are provided for monitoring two or more fluorophores, the two sensor channels are configured so that the emission passbands from each fluorophore do not overlap. In a preferred embodiment, a first detection channel is for the purpose of detecting a target signal and a second detection channel is for the purpose of detecting a control signal, and an assay result is reported if and only if a valid control signal is reported.

This system has proved useful in validation of assay protocols calling for paired collection of "biplex" or multiplex target and control signals. Where, as for FDA CLIA waiver requirements, both target and control templates are amplified in parallel, a positive control signal must be present before an assay result on a test sample can be reported or billed. In the absence of a detectable control signal, any target signal detected is not a valid result. If this condition is met, under the Clinical Laboratory Improvement Amendments of 1988 (CLIA), regulations governing simple, low-risk tests can be waived and the tests performed without oversight in physicians' offices and various other locations. In order to meet these CLIA waiver requirements, it is necessary that the fluorescence detector be able to detect not only the presence, for example, of a target infectious organism amplified by PCR but also of an endogenous human control organism co-existing with the target and amplified by the same PCR reaction or a PCR reaction conducted in parallel in the instrument.

Such an approach requires that the fluorescent detector used for such a molecular diagnostic assay may have the capacity to determine the presence of both the target and the control fluorophores as a "biplex" amplification reaction mixture in a common detection chamber. In one aspect, a positive amplification control fluorophore is used which has fluorescent excitation and emission spectra which is positioned to be well resolved (in wavelength) by selective band pass filters from the fluorescent excitation and emission spectra for the target fluorophore (see FIGS. 25A-25B for example). However, according to the present invention, it proved possible to achieve superior resolution by using a dual head detector and by scanning each detection chamber twice, once with each head, detecting first the control fluorescence signature, then the target sample fluorescence signature—each scanning pass requiring separate excitation and emission optics. A benefit was found by configuring these detectors with fully separated and independent light paths. In this aspect of the invention, the use of the duplex head design ensures that the presence of an amplification control fluorophore in a sample does not inadvertently create a signal in the target channel due to "crosstalk". Such a situation would result in the sample being classed as a "false positive". Conversely, it is also important that there is no crosstalk from the target channel to the control channel, which is likely when multiple signals share a common optical path. Such a situation could result in the positive amplification control being inadvertently deemed present, when this may not be.

These principles are exemplified by the use of fluorescein or equivalent fluorophore as a molecular probe for the target, and Texas Red or equivalent fluorophores as a molecular probe for the control. A dual head detector, with one detection channel optimized for detection of fluorescein and the other detection channel optimized for Texas Red, each with separate excitation and detection optics, was found to be surprisingly sensitive, accurate and robust for assaying biplex amplification mixtures. Separate fluorescence readings are made by the resident daemon for each optical channel. Surprisingly, this procedure both improved resolution and minimized cross talk but did not contribute to higher noise or loss of sensitivity due to the mechanics of moving the detector head.

Figure 26A:
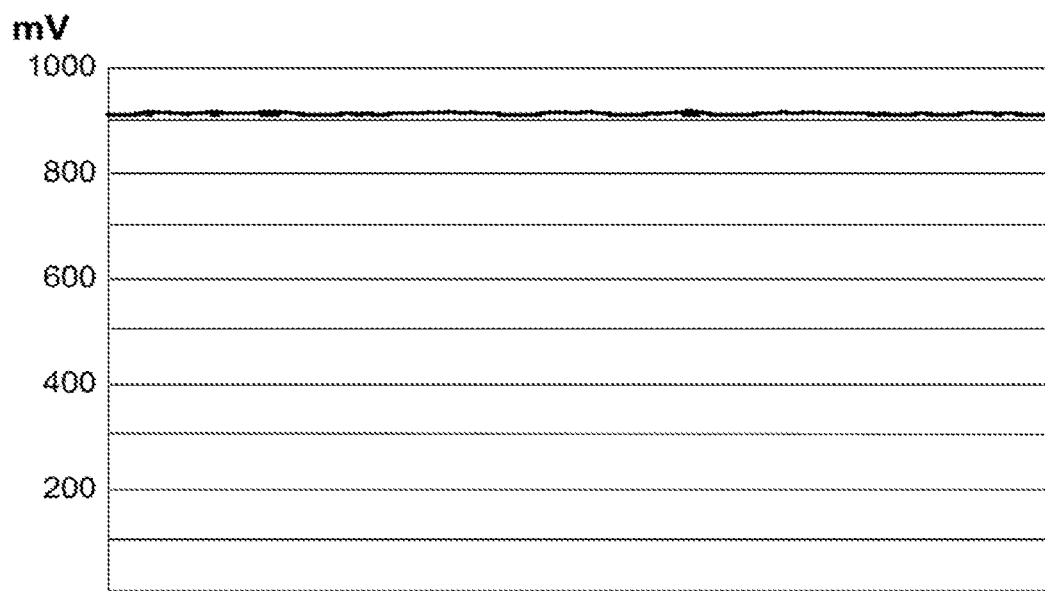
FIGS. 26A through 26D are views of electronic traces from the amplifier of the detector head under assay conditions with control and target signals.

FIG. 26A is a plot of the signal level received by the target channel of the detector in the case where a fluorescent target (in this instance indicating the presence of malarial nucleic acids from a molecular diagnostic assay) is present in the detection chamber embedded within a microfluidic cartridge. In this case it can be seen from the trace that the target channel receives a fluorescent signal from the detection chamber in the range 900 mV. The "malaria positive" signal in this case from the target channel is equal to approximately 14 times the "background" signal level of an empty detection chamber. The traces are smooth and indicate the low level of electronic noise in the amplification circuit within the shielded detector head.

Figure 26B:
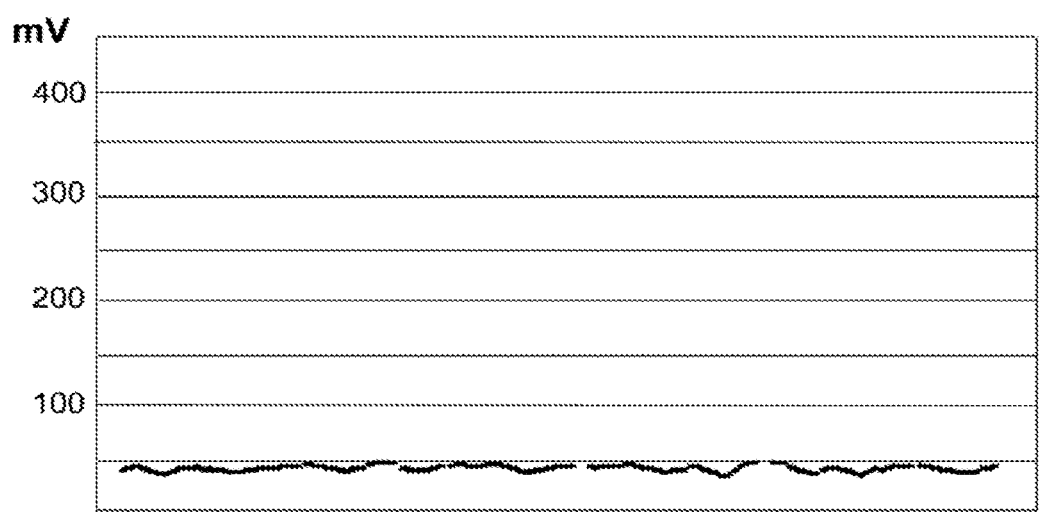

FIG. 26B is a plot of the signal level received by the control channel of the detector in the case where a fluorescent target (in this instance indicating the presence of malaria from a molecular diagnostic assay) is present in the detection chamber. In this case it can be seen from the trace that the control channel has an output in the range 40-50 mV, essentially equal to pre-scan baseline, as is indicative of a negligible level of crosstalk between the target optical channel and the control optical channel when scanning a detection well having only a target signal and no control fluorophore.

Figure 26C:
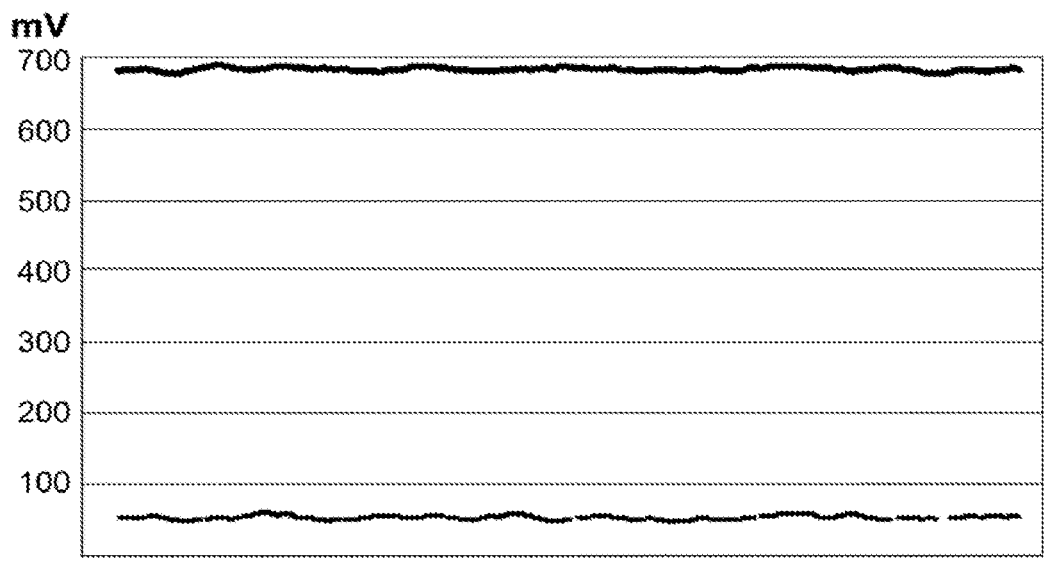

FIG. 26C is a plot of the signal level received by the target optical channel of the detector in the case where a fluorescent target (malaria, Texas Red fluorophore) and a fluorescent control (endogenous human control, fluorescein fluorophore) are amplified together as a mixture in a single detection chamber embedded within a microfluidic cartridge. In this case, the upper trace shows that a target signal level of approximately 680 mV was received in a first optical channel, where the target signal is associated with Texas Red-tagged malaria amplicon. This is equivalent to a level of approximately 10.5 times the signal from a blank detection chamber (lower trace). This indicates the detector functions correctly in identifying the presence of the "malaria positive" component of the biplex sample.

Figure 26D:
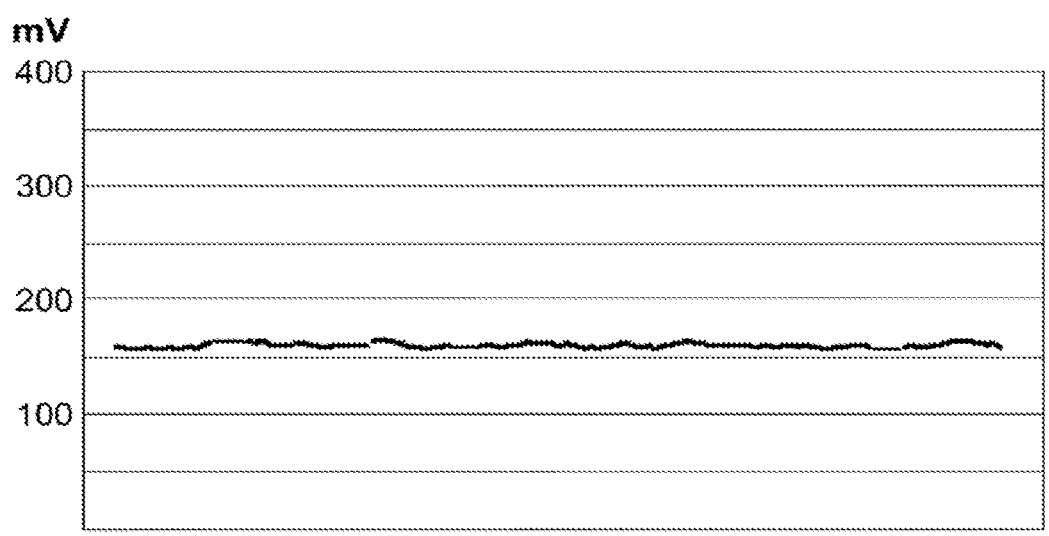

FIG. 26D is a plot of the signal level received by a second optical channel of the detector in the case where a fluorescent target (malaria) and a fluorescent control (endogenous human control) are present together in the detection chamber embedded within a microfluidic cartridge. The biplex sample mixture is the same as for FIG. 26C, and the signal is associated with a fluorescein-tagged endogenous control amplicon, demonstrating no crosstalk from the target amplicon and good signal stability and freedom from electrical noise.

In this case, the trace shows that a signal level of approximately 160 mV was received by the control optical channel. This is equivalent to a level of approximately 3.6 times the signal from a blank detection chamber. This indicates the detector functions correctly in terms of identifying the presence of the "control positive" component of the biplex sample in a separate optical channel. Thus target amplicons and control amplicons are detected in a single well, as is indicative of a successful "biplex" assay per the CLIA waiver requirements.

Because excitation is not performed with white light, but is instead performed at a wavelength specific for an individual fluorophore, quenching of the second fluorophore is not an issue. The systems described here use a combination of physical methods and signal processing methods to achieve robust assay performance such as is needed for reliable operation outside the controlled environment of a clinical laboratory.

Figure 27:
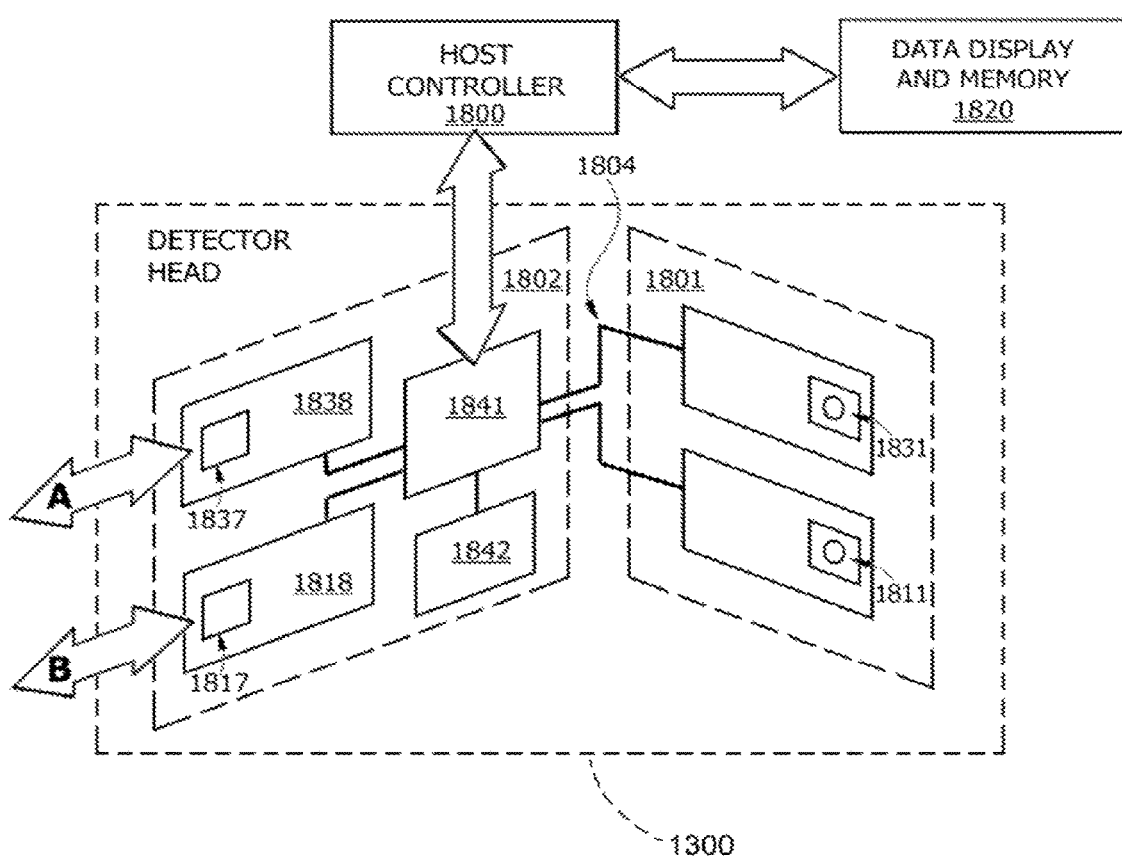
FIG. 27 is a block diagram of the detector head electronics used for controlling the fluorescent excitation, and receiving, processing, and digitally communicating fluorescence emission signals to the host instrument.

FIG. 27 is a block diagram of the detector head 1300 electronics and optics used for controlling the fluorescent excitation and for receiving, processing and digitally communicating fluorescence emission signals to the host instrument. Optical channels are again identified by open arrows A and B and terminate in sensors 1817 and 1837. Channel A is taken as a control channel and channel B as a target analyte channel, but the roles are interchangeable. The electronic functional blocks in each channel, source (1811, 1831 and associated circuit block) and sensor (1817,1837 and associated circuit block) are identical (with the exception that channels A and B are configured for different wavelengths).

The detection system can be configured for wavelengths in the UV, visible region, and near infrared spectrum. Available light sources having near monochromatic output, filters, chromophores and fluorophores allow for tuning excitation and emission passbands in the range of 300 to 900 nm. For applications in fluorescence detection mode, which is one of the preferred operating modes of the invention, the apparatus can be configured for specific fluorescence dyes with excitation spectrum in the UV and visible spectrum and for emission in the UV, visible and near infrared spectrum. While a red shift is more typical, up-converting fluorophores may also be used.

Within the detector head 1300, each of the LEDs associated with source excitation circuits (1811, 1831) are modulated by a square wave at a frequency of 130 Hz. The reason for this modulation is related to noise reduction measures from the following potential noise sources: 1) 50/60 Hz AC mains; 2) 100/120 Hz second mains harmonic from the fluorescent lights; 3) Third and higher harmonics of 50/60 Hz AC; 4) Differential frequencies (rumble) of 130 Hz and higher; and 5) Wide band white noise from the photodiode sensor, first stage feedback resistor, and amplifier. In order to retrieve a useful signal from the noisy source, the following mitigation methods are employed: 1) Fast sampling and averaging of taken data in order to avoid aliasing and at the same time limit noise bandwidth; 2) Modulation of the LED light at 130 Hz and correlation with the detected fluorescence signal at 130 Hz in order to reject all uncorrelated components (a 130 Hz modulating frequency was selected to provide at least 10 Hz difference from the 50/60 Hz mains and harmonics at 100, 120, 150 and 180 Hz and higher); and 3) Further filtering and processing of the correlated data to eliminate electromagnetic noise from mains power supplies of either 50 Hz or 60 Hz or harmonics thereof. The excitation LEDs are turned on and off using a 130 Hz square wave driven by FAN5612 LED-drivers. Each driver is capable of sinking current up to 120 mA (40 mA on each of three outputs) at the required frequency. The clock frequency of the detector head microprocessor is used to strobe the excitation LEDs and to synchronize pulse collection in the sensor diodes. These features are found to produce a quiet output from the sensors in the absence of specific fluorescence signal and enable higher amplification.

The circuit board 1801 for the source LEDs can support multiple LEDs, and the circuit board 1802 for the sensor circuit can support multiple photodiodes. The excitation and detection circuit are electronically isolated using bypass capacitors on separate PCB boards (1801, 1802) on separate ground planes to further reduce any possible crosstalk through pin junction 1804. Each photodiode is shielded and intimately associated with a multiple stage high gain amplifier (1818, 1838) and the two circuit boards are electronically isolated with separate grounds. In the detector head, electrical output from the sensor optics is conditioned in a preamplifier and fed into a three-stage amplifier. Each of three outputs from the amplifier has a multiple log scale gain, with the highest amplification factor being up to $10^{14}$. The three outputs are fed into A/D converters integrated into the embedded microprocessor, and one digital output (the output selected by firmware) is bussed as a digitized score to memory.

Advantageously, the isolation of the analog and digital signal processing circuitry within a shielded detection head realizes low noise conditions that permit very surprisingly high gain factors, up to $10^{14}$, and in selected embodiments between $10^{12}$ and $10^{14}$ in three stages. By localizing the digitization electronics within the detection head next to the sensors, amplified signals having high gain are achieved with a surprising lack of noise interference. Buffered and filtered reference voltages are also supplied to the op amps to ensure maximum stability in amplified signal output, which is digitized in an A/D converter associated with the embedded microprocessor 1841; thus digitization occurs within the scanning detector head.

While the above is a description of the hardware, the actual operation of amplifier electrooptics and the signal processing algorithms in the detector head is conducted by an "ODAP daemon" coded in the firmware, which functions as a "virtual machine". The daemon is essentially a set of instructions, but is resident in the detector head in nonvolatile memory digitally associated with the embedded microprocessor and operates independently, once called out, of the host controller. The firmware, a dedicated on-board instruction set for control of signal acquisition and the optoelectronic functions of the scanning detector head, is typically resident in a socketed EEPROM chip 1842. The daemon controls the embedded microprocessor 1841 in the detector head. After digitization of the amplified signal, the daemon is capable of further signal processing, for example comparing optical data with background scans and/or making a complex determination as to whether the fluorescence is a positive assay result before reporting data to the host system for display to the user.

Surprisingly we have found that the two processors, the host controller and the embedded microprocessor in the detector head, can be coordinated so that the ODAP daemon is able to construct a spatial map of the sample area while the detector head is moved under external control of the host controller. ODAP functions proceed autonomously in collecting signal data, for example, while the host controller performs a melt/anneal subroutine on the temperature in the detection chamber, so that assay reprogramming in the host controller routines does not affect or impact the operation of data acquisition and reporting under control of the daemon, a distinct advantage where, depending on a barcode read from the assay cartridge, any of several assay protocols may be performed by the host controller.

One advantage of using an embedded microprocessor 1841 inside the detector head is that a proprietary method of "optical data acquisition and processing" (ODAP) may be programmed into the firmware in the detector head to eliminate noise before transferring a clean, digitized signal to the host controller. The ODAP daemon is thus an independent subroutine or subroutines that is invoked by the host processor when needed—but that once initiated the daemon and associated optoelectronics run autonomously under independent control of the embedded firmware. In practice, it has proved possible to complete the entire analysis within the detector head and to simply communicate a summary score or assay result to the host instrument. Unlike analog signals, digital transmissions from the detector head to the host instrument are not susceptible to interference caused by the noisy analog machinations occurring within the instrument housing.

As currently realized, the ODAP daemon runs continuously and autonomously as the detection head is scanned linearly across the cartridge. "Daemon" refers here to the operation of a programmable instruction set for optical data acquisition and processing that is stored in firmware which is executed by an embedded microprocessor as an autonomous background process rather than under the direct control of an interactive user or by the host controller. The daemon is in part a virtual machine which operates and controls electronic circuitry that is localized in the detector head so that it can be protected from external electronic noise associated with host operations.

Thus the invention includes a method for automating a microassay, which comprises operationally dividing the assay into fluidic, electromechanical, and thermal processes controlled by a host controller and optoelectronic processes controlled by an autonomous daemon resident in a scanning detection head, where the motion of the scanning detection head is controlled by the host controller and any optical signal acquisition and processing is controlled by the autonomous daemon.

By way of illustration and example, three detection chambers, each for analyzing a liquid sample, are disposed in an optical window that is scanned by the detection head. Scan time is about 30 sec and the scan length is divided into about 500 steps. The detector is operating at 130 Hz, but the digitization rate is higher, so that 12000 to 24000 measurements of fluorescence may be taken during each scan. Sensor diode output is stored and averaged so that the dark half-cycle can be subtracted from the light half-cycle as the LED is strobed at 130 Hz to eliminate non-specific photodiode output. The dataset is further processed under control of the on-board firmware in 100 ms increments. Thus the digitized score tabulated in local memory in the detection head consists of a processed signal acquired over 100 ms and corresponds to one or only a few steps in the linear scan, depending on the characteristics of the stepper motor and the length of the scan. The "spot size" corresponding to the signal is thus fairly small but not so fine as a high resolution digital pixel. Each digital score has a value that corresponds to all the amplified current accumulated during the LED ON time intervals less any ambient signal during the LED OFF time intervals.

The daemon is synchronized to track stepper motor actuations and accumulates a table of fluorescence output scores versus scan distance (position) over the width of the optical window. By performing a baseline scan prior to assay, any "new" signal (i.e., any change over baseline) that results from dyes, chromogens or fluorophores associated with the assay reactions is then quantitated. After background subtraction is complete, a threshold value may also be used to further filter signal changes over baseline if desired.

Data sampling, filtering, digital smoothing and conditioning, may be achieved by a combination of hardware and firmware means, the firmware referring to the daemon instruction set. Programmable statistical analysis of the digital scores acquired during a scan across a sample well may be parametric or non-parametric. From each dataset specific to each sample well, the distribution of the scores over the scan transect is a better predictor of the assay truth value ("positive" or "negative" for target analyte or control) than an average, a median or a mode value taken over the well. A result based on a distribution function having many points is also superior to an optically averaged signal taken by interrogating the well at low resolution. Averages can lead to false negatives, whereas we have found that a pattern of high signal spikes, even if localized to a particular part of the well, is highly likely to correspond to a positive assay. The firmware is configured to assess and correlate the intensity of the digital scores and the frequency of signal spikes with expected ranges for positive versus negative assay results. Datasets may be considered as population statistics, where a population of 30 measurements, ranked according to intensity, for example, is compared to a distribution expected according to a null hypothesis according to statistical analysis of variation. Statistical tools for assessing the data non-parametrically are also applicable and may be encoded in firmware. Thus in a preferred embodiment, the on-board capabilities of the detection head encompass outputting an assay result as a digital "one" or "zero" corresponding to whether an analyte has been detected, true or false, and also the status of the corresponding controls. Surprisingly, we have found that aberrations in the datasets due to bubbles and other irregularities can be managed by a conversion to a 1-bit digital score, generally under control of the daemon with embedded firmware.

Inputs into the embedded microprocessor are multiplexed so that several target analytes and controls may be assayed simultaneously. The detector head is provided with at least two or more optical channels, each having independent excitation optics and emission optics which are operative at discrete wavelengths. White excitation light is not used to eliminate possible crosstalk between different fluorophores in a multiplexed assay, such as when a target fluorophore and internal control fluorophore are mixed in a common liquid sample. The use of "one pot" conditions for target and control results from the need to prove that conditions for a positive control signal are present in each sample well (avoiding false negatives). But by separating target and control channel optics, crosstalk that could lead to false positive tests or test rejection due to invalid control results was eliminated.

For comparison, the host controller 1800 is responsible for the operator interface, including display of results, and for operation of mechanical and pneumatic functions required to perform an on-cartridge assay and detector head scan. A separate clock in the host controller is used to drive the stepper motor during scanning. To correlate detector head position with fluorescence signals acquired during the scan, stepper motor activity is monitored by the firmware in the detector head.

Well position recognition is achieved by an "edge detection" process operated under control of the embedded daemon in the scanning detector head. In a first instance, a pair of mechanical switches is mounted on the underside of the detector head with leads digitally communicating to the embedded controller. In a first scan of an empty cartridge, the detector head glides along its rail under host instrument control of a stepper motor, and when a first mechanical switch is tripped by a detent formed in the instrument chassis alongside the rail, then an electronic signal is sent to the daemon. The daemon is programmed to initiate its activities and will start capturing stepper motor data from the host instrument and using this data to map an x-axis transect across the optical windows of the cartridge, where each step of the motor corresponds to a position and a distance increment n defined by the stepper motor such that ($x_i=x_0+(ni)$) for any distance $x_i$ from a reference point $x_0$. The daemon also stores optical output during the first scan. Thus the daemon tabulates a position $x_0$ and an intensity $I_0$ datapair and continues to increment $x_i$ as the stepper motor advances the detector head. By virtue of discontinuities in the cartridge optics that are associated with sample wells, an optical scan of the cartridge along the x-transect results in signals that are useful for well edge detection. These signals are characterized by a peak where a positive slope is separated from a negative slope by a peak condition $dx/dt=0$, or by a sudden step change (drop or increase) in the baseline optical output as the detection head crosses over a nearside edge of the well. If a threshold value is crossed, then the edge effect associated with the entry into the well is scored by the daemon as a well start position having an x-coordinate (motor step number) on the linear map or x-transect. Because the detector head is mounted on a rigid guideway, the x-transect path can be reversed, and the scanning head can precisely retrace its route in a subsequent scan across the well from the same start point $x_0$. In this way, a definite physical distance is established by the mapping process from the position on the rail where the mechanical detent was tripped to the well edge. Similarly, a farside edge of a well is identified. The background optical readings of the empty well between the nearside edge and the farside edge positions are then processed and stored as a representative background signal. This process is repeated for all wells, and is repeated again for each optical channel in the detector head. With appropriate offsets, the mechanical switches may be used for more than one channel, so that an x-transect is collected for each optical channel during a single scan. Similarly, multiple wells may be scanned one at a time as the scanning head scans along the optical window.

The detector head then returns to its rest position, and on command, starts a scan that will detect any changes in optical output associated with a sample filling the wells. The daemon collects data from the detection wells according to the predefined well edge positions in memory and performs calculations to evaluate changes in fluorescence (or other optical signal), associated with the contents of the wells. These data are further processed by signal processing algorithms operated by the daemon. Changes or lack of changes in fluorescence in each of the wells after introduction of sample may be indicative of the presence of a control signal and/or the presence or absence of a target analyte signal depending on the assay design.

Edge detection may include filters such as a triangular filter or other signal filters known in the art. Fidicials associated with the edges of the cartridge wells may include colored layers deposited or laid down around the wells, physical edges that result in optical scattering, cassette materials having autofluorescence, and so forth, as are known in the art. Thus the mapping routine may alternatively be indexed to a fiducial associated with the cartridge body or a sample well such that an initial reference point is established optically, electrically or mechanically. A set of datapairs for the initial position $x_0$ and associated intensity $I_0$ is recorded. Subsequent datapairs ($x_i,I_i$) are collected as well mapping proceeds stepwise ($x_i=x_0+(ni)$) where n is the number of steps of a stepper motor and i is a step distance. Algorithms are used to detect signal changes characteristic of sample well edges and these are indexed so that one or more sample wells in a scanning transect are indexed. Thus a pre-scan may be performed and digitized baseline optical signal data collected; then the sample wells are flooded with liquid containing the analytes of interest and a second scan is performed: the difference between the two scans is representative of the target analyte and/or control analyte of interest. Signal processing and digitization and subsequent analysis are performed under the control of the autonomous daemon within the detector head.

Figure 28A:
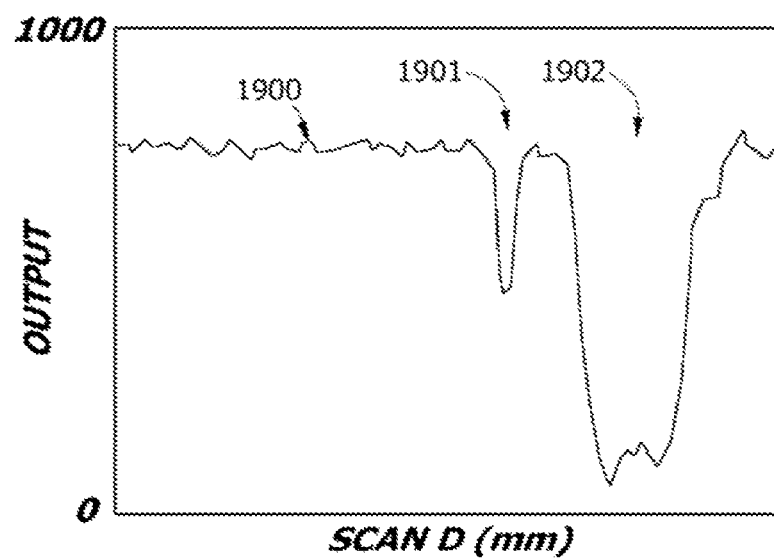
FIGS. 28A and 28B are representations of raw input and digitized output showing digital removal of bubble interference.
Figure 28B:
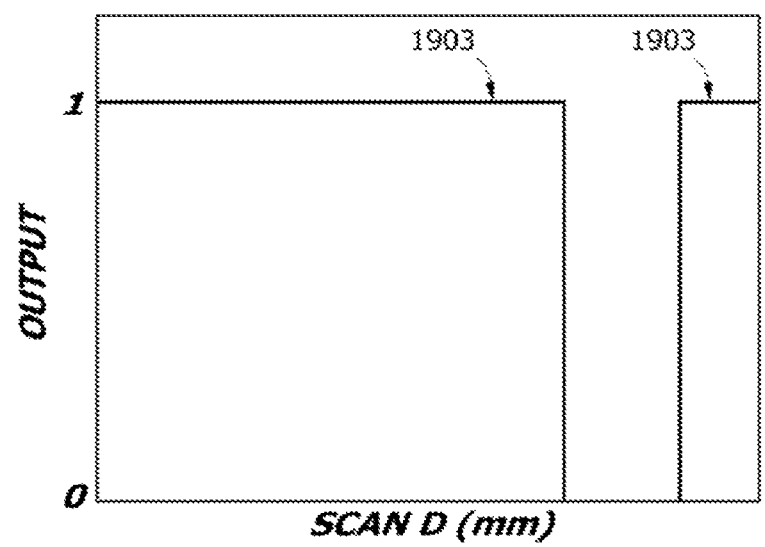

FIGS. 28A and 28B are representations of raw input and digitized output and demonstrate a method for digital removal of bubble interference by the daemon. In FIG. 28A, output (1900) from the photodiode after amplification is represented. The level of noise is generally low, but signal deteriorates at 1901 and 1902 due to the presence of two small bubbles in the detection chamber (1501, see FIG. 29), for illustration. The daemon applies a threshold to the output signal and scores the signal "high" (i.e. a one) if the signal is above the threshold and "low" (i.e. a zero) if the signal is below the threshold. Because no signal output can be above the threshold except in the presence of a fluorophore matched to the emission optics and filters, any positive signal (1903) is a positive assay for the presence of fluorophore. The threshold comparator can be adjusted based on experience with clinical samples in the assay. Thus a "1-bit" digital transformation of the scanning image data removes any interference from bubbles. We have found surprisingly that when a fluorophore is present but multiple bubbles fill the chamber, light refracted around or through the bubbles will result in a positive signal. The system is thus very error resistant and robust for qualitative testing, such as is needed in diagnostic assays for infectious disease. The signal comparator is a digital function of the microprocessor and firmware embedded in the detector head and is independent of host controller function.

Host Controller Functions

Again with reference to FIG. 27, the host controller 1800 is responsible for actuating the daemon, but does not control its operations. During operation of the daemon, the host system multitasks to perform various assay functions such as temperature and pneumatics control, detector head scanning, user interface operability, and fault monitoring.

Among other functions, the host controller actuates system hardware for controlling pneumatic logic and pulse train routines needed to perform the assay, including valves and diaphragm pumps in the microassay cartridge, any resistive or Peltier-type heating elements associated with thermal cycling of the sample, and optionally may perform melt curves in the detection chamber by actuating resistive heating elements during melting and a blower during cooling (FIG. 22). Optional components interfacing with the host controller include a bar code reader for sensing information printed on the insertable microassay cartridges.

The host controller is provided with non-volatile memory and programmable instructions for coordinating the steps of an assay process and for transforming and formatting a signal, result or other data from the embedded daemon into a machine-readable or graphically displayable report in a form that will be made available to the user. A graphical user interface 1820 for displaying test data can be integrated into the detection system as shown here or can be connected to it through data lines or wireless interfaces as part of a network, intranet or internet. Generally, a serial asynchronous communications interface is provided for communication with the host controller on the instrument motherboard or on an external network.

Similarly, results, data, error codes, status updates, and so forth can be sent via common electronic interfaces and data lines such as USB, RS232 or FireWire and via a wireless transmission system such as IR-transmission, Bluetooth, GSM, GPRS, and RSID. Programming, reprogramming, calibration, and recalibration as well as system diagnosis of the device is possible via common electronic interfaces and data lines such as USB, RS232 or FireWire and via a wireless transmission system such as IR-transmission, Bluetooth, GSM, GPRS, RSID, and so forth.

Decoupled Optics

Figure 29A:
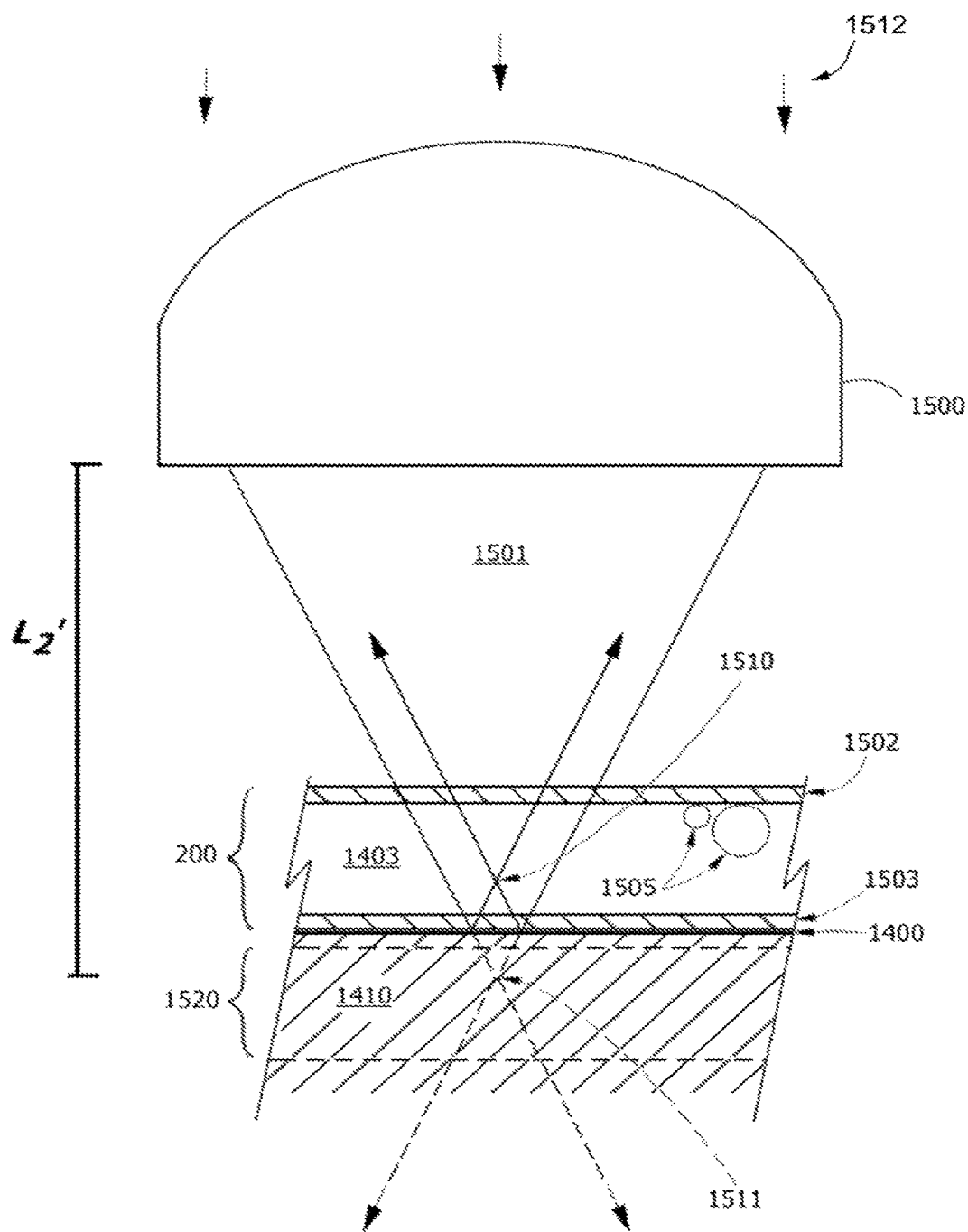
FIG. 29A is a representation of an excitation cone and planoconvex objective lens relative to the cartridge detection chamber and mirror-faced heating block.

FIG. 29A is a representation of a planoconvex objective lens 1500 in excitation mode. Excitation cone 1501 is shown relative to the cartridge detection chamber 1403 and heating block 1410 with mirror face 1400. The convergent excitation cone is formed by diverging rays illuminating the objective lens from the source, whereby the focal position distance L2' is greater than the native focal length L2 of the lens. By convention, the native back focal length L2 of the lens is determined using collimated light. Shifting the focal position is termed "decoupling", and was achieved in this instance by moving the source closer to the source lens, but more generally decoupling can be achieved by using non-collimated light.

Interposed between the lens 1500 and the mirror face 1400 is a microassay cartridge 200 with detection chamber 1403. The detection chamber is bounded by an upper optical window 1502 and a lower thermo-optical window 1503. In operation, the intervening volume is taken up by a liquid sample, shown here with two entrained bubbles 1505. The focal cone is seen to reflect from the mirror face, forming a real image (1510, solid rays) of the source in the detection chamber and a virtual image (1511, dashed rays) of the source below the mirror face. The back focal position L2' is thus generally equal to or greater than the distance between the lens and the mirror. Excitation light striking the mirror is reflected as a focused beam in the fluid volume of the detection chamber, thus doubling the length of the light path of the excitation light through the sample and increasing the excitation fluorescence yield. The back focal position L2' is not equal to the back focal length L2 of lens 1500; the two are decoupled, generally by illuminating the lens with a divergent beam from the source 1512.

Figure 29B:
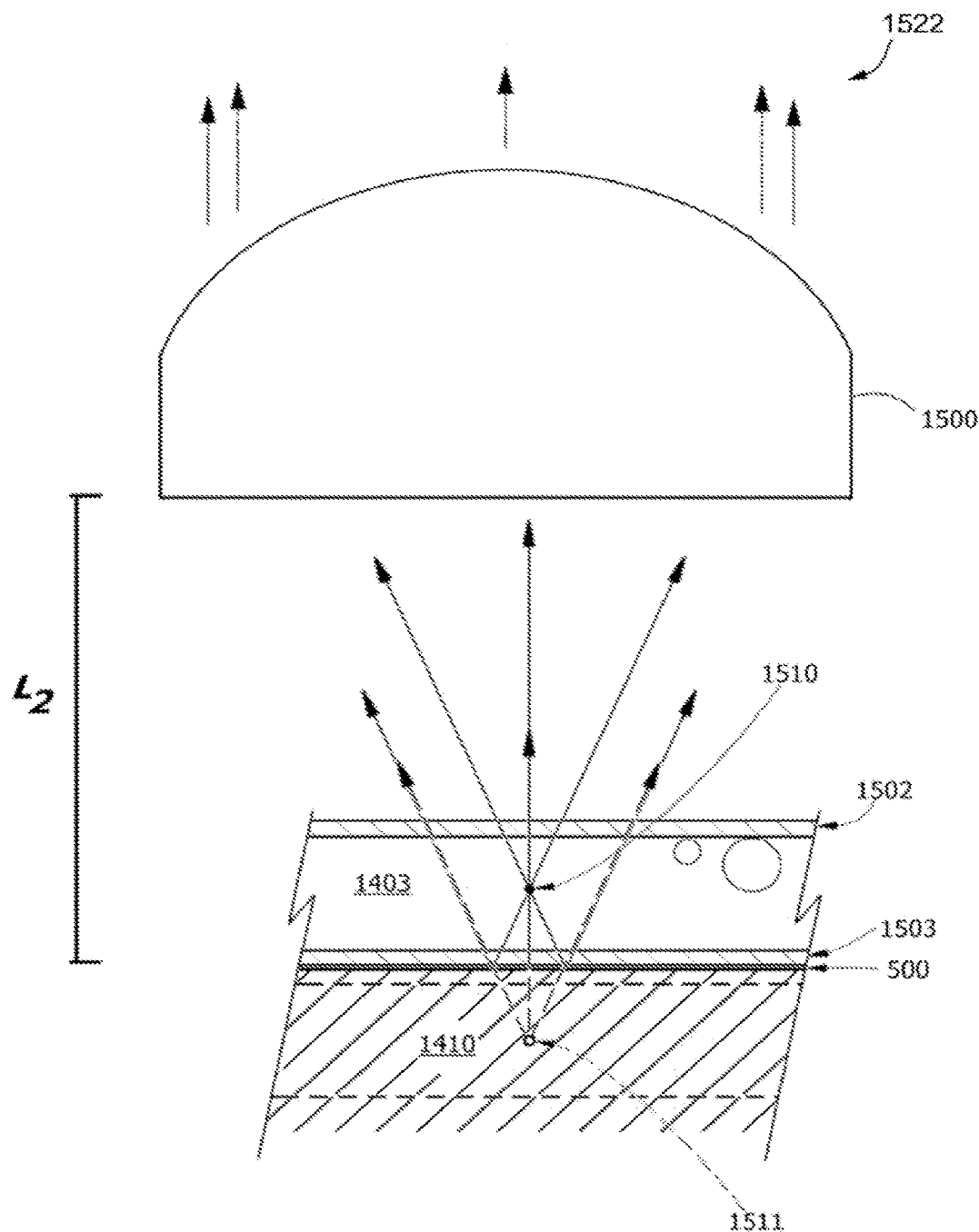
FIG. 29B is a representation of emission collection with a planoconvex objective lens at short working distance relative to the cartridge detection chamber and mirror-faced heating block. Shown are primary and reflected fluorescent emissions.

FIG. 29B is a representation of the objective lens of FIG. 28 in emission collection mode. Shown are primary and reflected fluorescent emissions (solid and dashed lines from a real image 1510 and a virtual image 1511). Again shown are bubbles in the chamber 1403. Rays striking the planar back surface of the objective lens 1500 will be collimated (1522) and transmitted to a detector. The quantity of fluorescence signal captured depends on the angular and numerical apertures of the lens. The native back focal length of lens 1500 is L2. The back focal position of the lens can be manipulated or "decoupled" relative to the native focal length of the lens (L2 versus L2') by repositioning the source as shown in FIGS. 30 and 31 or by changing the shape or refractive index of the source lens.

Figure 30:
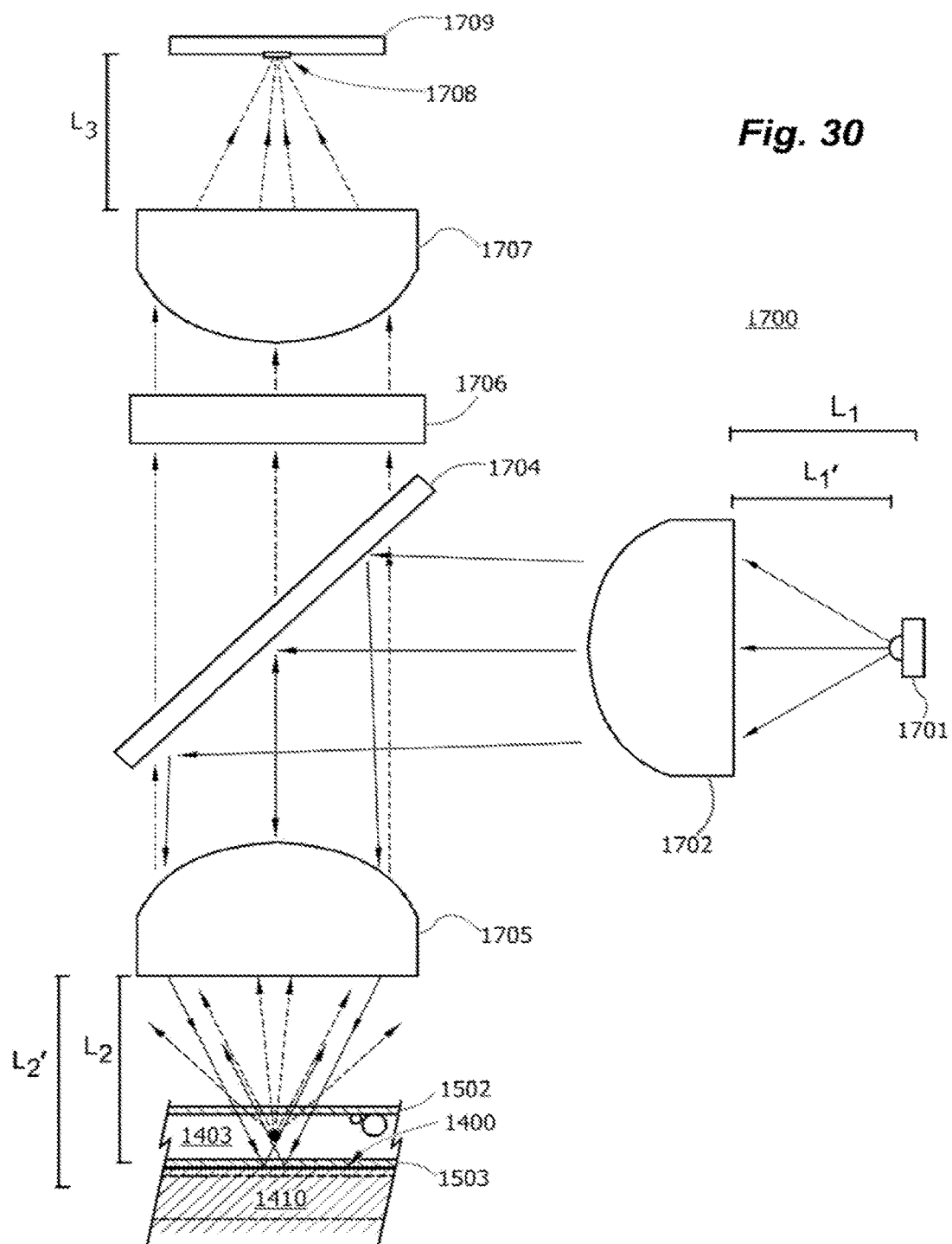
FIG. 30 is a schematic representation of an optical pathway with decoupled excitation and emission optics where L1'<L1 and the source beam is divergent.
Figure 31:
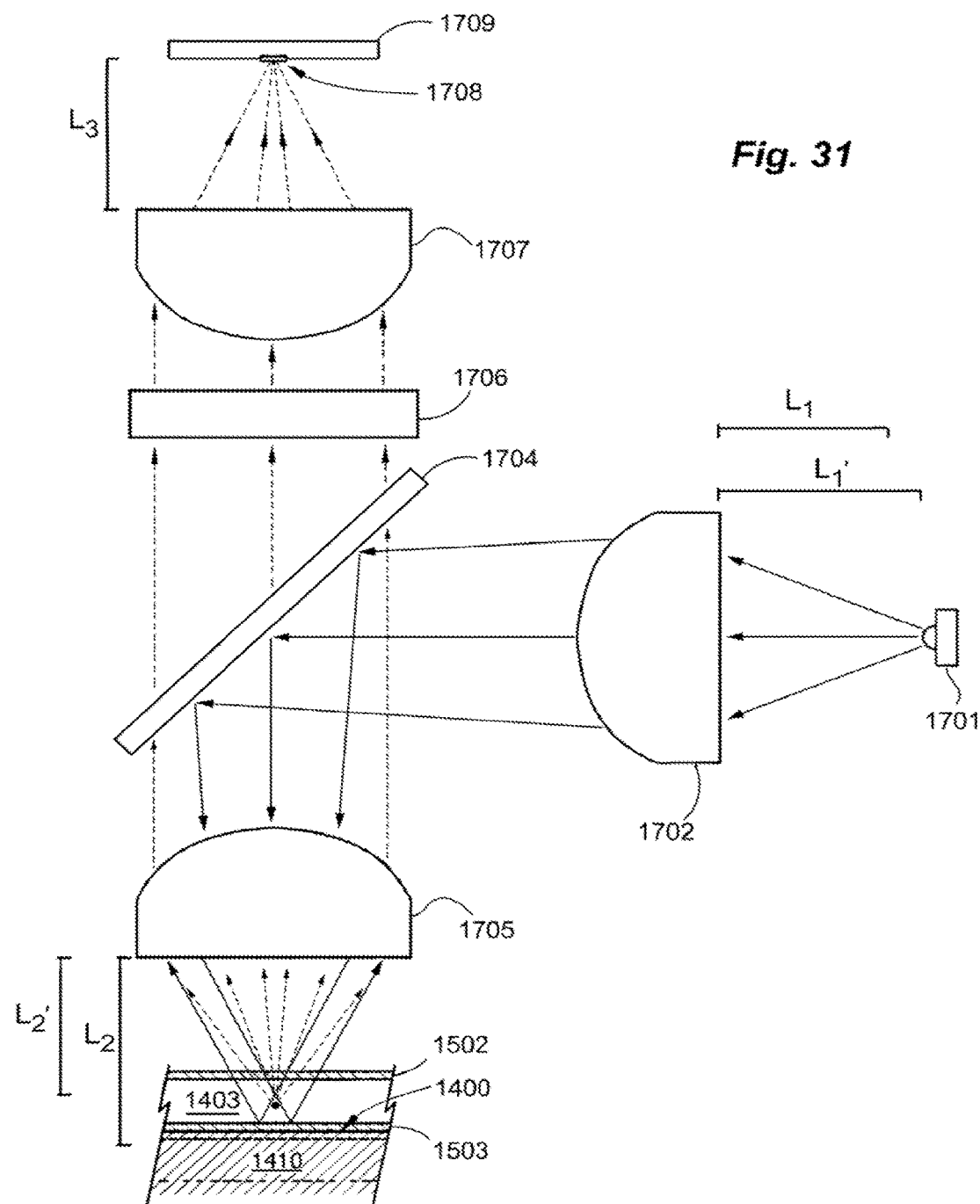
FIG. 31 is a schematic representation of an optical pathway with decoupled excitation and emission optics where L1'>L1 and the source beam is convergent.

FIG. 30 is a schematic representation of an optical pathway 1700 with decoupled excitation and emission optics. In this figure, excitation rays are shown as solid lines and emission rays are shown as dashed lines. Here the light source 1701 may be an LED as shown, an SMD LED without lens housing and reflector ring, an SLED, a pumping laser diode, a ridge-waveguide (Fabry Perot) laser diode, a tunable laser, and so forth, such source of illumination preferably having a narrow bandwidth. LEDs of various narrow bandwidths are available, for example with peak emission at 630 nm (red), 470 nm (blue), 525 nm (green), 601 nm (orange), 588 nm (yellow) and so forth. White light LEDs may be used if desired, but generally the LED output is matched with the fluorophore of the target in the assay and an optional excitation barrier filter (not shown) may be used to sharpen the bandpass as required. Light output of light source 1701 is transmitted by source lens 1702, shown here as a planoconvex lens, although molded aspheres may also be used, before striking dichroic mirror element 1704, where the excitation beam is reflected onto objective lens 1705. The excitation cone striking a sample fluid volume 1720 in microassay cartridge 1402 is shown with solid lines. Unconventionally, the focal point of the excitation cone has been projected past the sample chamber and back mirror 1400 by moving the source 1701 closer to the source lens 1702 (i.e., shortening distance L1' in order to increase distance L2', where distance L1 would be the native back focal length of lens 1702). As distance L1' is shortened, the source rays striking the objective lens are not collimated by the source lens and are caused to diverge, thus increasing distance L2'. The native back focal length of objective lens 1705 is L2, where L2 is less than or equal to the distance separating the back of the objective lens and the mirror, i.e., preferably is within the plane of the sample chamber, so that any emissions from a fluorophore in the sample chamber and any reflected emissions forming a virtual image of the fluorophore in the mirror will enter the objective lens. The emissions cone has a focal point that is decoupled from the focal point of the excitation light (which is focused behind the mirror). Fluorescent emissions within the focal plane L2 and any virtual image of light originating in the focal plane are effectively collimated by the objective lens, are effectively transmitted through dichroic mirror 1704, bandpass filter 1706, and are then focused by sensor lens 1707 onto sensor 1708, which is typically mounted on a PCB or other solid support 1709. Lens 1707 has a back focal length L3 that generally is equal to back focal length L2 of objective lens 1705. However, a larger lens 1707 may be used to better utilize the surface area of the sensor 1707, which is for example a photodiode or CCD chip. Optimization of signal may require independent adjustment of each lens according to the principles of decoupled optical systems outlined here, and may use non-collimated excitation light, contrary to the teachings of the prior art.

The cone of excitation light emerging from objective lens 1705 and the cone of emission light entering objective lens 1705 on a common optical axis are operably decoupled at different focal points (indicated by focal positions L2' versus L2 respectively). A distance separates the actual focal plane of the excitation light and the native focal length of the objective lens. The objective lens will capture light in a broad plane of origin of the fluorescent emissions when excited using a mirror and an extended focal position of the excitation cone 1501. This phenomenon, termed "decoupling" was found to increase capture of fluorescent emissions when a back mirror is used, and controverts earlier teachings in favor of the confocal approach of the prior art.

While the teachings of the prior art strongly support making the excitation and emission confocal, there is in fact a previously unseen advantage in decoupling the focus of the source from the emission cone and using a back mirror 1400. Emitted light arises from a greater area and depth throughout the sample cartridge, thus overcoming any lack of signal from dead spots or inhomogeneities as would be due to small bubbles, unmixed areas, or quenched probe. Greater reliability is achieved at the expense of some selectivity for excitation originating at the point of focus, but spatial selectivity for excitation is in fact not desirable in an assay device. This is a technological advance in the art.

To summarize, in certain embodiments L2' may be greater than L2 and L3. L1 advantageously may be configured so that the cone of excitation light falls behind the sample chamber 1403 and most preferentially close to or behind the back mirror 1400. In a preferred embodiment, the focal point of the excitation cone falls on or behind the back mirror. The objective lens is configured, generally, so that emitted light is efficiently collected and collimated for projection onto the detection sensor by a symmetrical cone of emitted light from sensor lens 1707 (i.e. L2=L3).

Accordingly, in another embodiment the apparatus of the invention employs lenses configured so that excitation optics and the emission optics are decoupled. In a first embodiment of this apparatus, the light source is positioned at a distance L1' from the source lens, where L1'<L1, whereby the excitation optics and emission optics are decoupled by transitioning the excitation cone to a focal position L2' at or behind the mirror face, such that L2'>L2. More generally, the source lens is configured to form a diverging beam of light incident on the objective lens, thereby positioning the excitation cone at a focal position L2', whereby L2'>L2.

Advantageously, L2 is configured to be symmetrical to L3 (i.e., L2=L3), so that the operation of detector 1708 is optimized and robust. The sensor photodiode is preferentially configured to be large enough with reference to the cone of focus of lenses 1705 and 1707 to accommodate some degree of misalignment without loss of assay validity.

In an alternate embodiment of decoupled optics, the native focal point of the objective lens and the actual focal point of the excitation light are separated by a distance such that L2>L2'. This is illustrated in FIG. 31, where the source 1701 is moved away from the source lens 1702 such that the native back focal length of the lens is exceeded (L1'>L1). The effect of such a repositioning is to cause rays emitted from the source lens to converge as they approach the objective lens 1705 as shown, and the ultimate effect is to shorten L2'. By placing the excitation cone focal position directly in the middle of the sample chamber 1403 between optical windows 1502 and 1503, and by using a mirror 1400, excitation of fluorophores in the sample liquid is achieved. But in this instance of the use of decoupled optics, the objective lens is also moved closer to the sample chamber and the native back focal length of the lens L2 is now positioned behind the mirror. The effect of this is to increase the apparent angular aperture of the lens, i.e., by moving the lens closer to the fluorophores, more light is collected and redirected to the sensor. As before, collimated output from the objective lens is focused on sensor 1708, and thus typically L2 can equal L3. Thus the principles of decoupling are shown in FIGS. 30 and 31 to encompass two complementary methods for using non-collimated excitation light to optimize signal collection efficiency when used with the mirrored thermo-optical interface that is also an aspect of the invention.

Decoupling is useful not only in assays where differentiation of a positive or negative assay result is required, but also in assays were some level of quantitation is required, as for example schizont or merozoite copy number in the case of Plasmodium falciparum. It should be recalled that the original purpose of confocal optics, as articulated by its inventor, Minsky in 1957 (U.S. Pat. No. 3,013,467), was to create a three-dimension image of a thick solid specimen by rastoring a focal point of excitation across and through the specimen (xyz axis rastoring) while monitoring emission only from the area of the specimen where the excitation cone is focused at any given time. In contrast, in a fluid mixing specimen that is generally homogeneous, an opposite effect is desired, that of measuring the overall fluorescence of the specimen with the highest possible fluorescence capture. In systems where multiple measurements are taken during a traverse of the specimen, statistical methods can be used to overcome interferences such as caused by bubbles, and a strong positive signal, regardless of where it originates in the sample chamber, is likely to indicate a positive assay result. Thus by reformulating the problem, we have been able to design a novel optical system with back mirror, with decoupling of the focal plane of excitation and emission, with the happy result that fluorescence detection is more sensitive and more robust in the presence of occasional interferences.

Figure 32A:
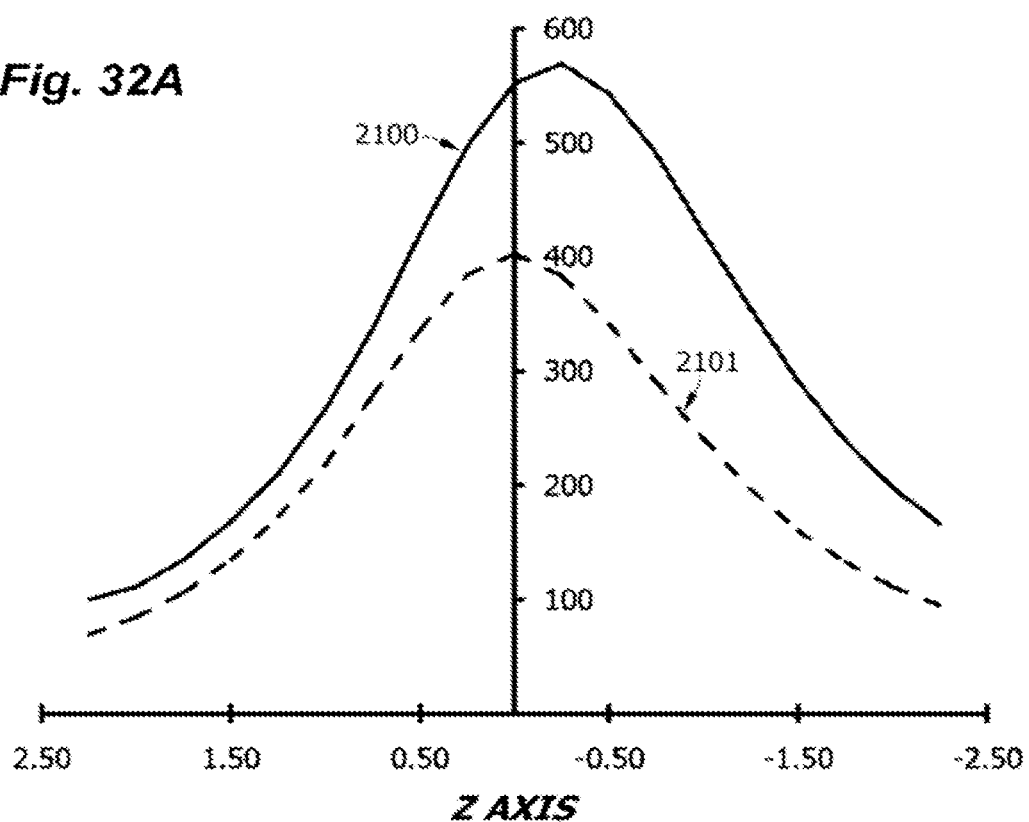
FIG. 32A plots experimental results demonstrating enhancement of signal output by varying the height of the objective lens above the mirror.

FIG. 32A plots experimental results demonstrating enhancement of fluorescent signal output by varying the height of the objective lens above the mirror. Briefly, fluorescent beads (Thermo Fisher Scientific, part number G0300, Pittsburg Pa.) were inserted into a microassay detection chamber and the detection chamber mounted under the objective lens 315 of the detector. Using a digital micrometer, the height of the detector head above the microassay cartridge was then varied to construct the plot. In a second paired experiment, the mirrored surface was removed. The solid line (2100) shows the effect of varying the lens height in the presence of a mirror on the heating block; the dashed line (2101) shows the effect of varying lens height in the absence of a back mirror. As can be seen, the presence of the mirror seems to shift the optimal emission maximum behind the mirror plane (i.e. a composite of the real and virtual fluorescent emissions captured in the lens).

Figure 32B:
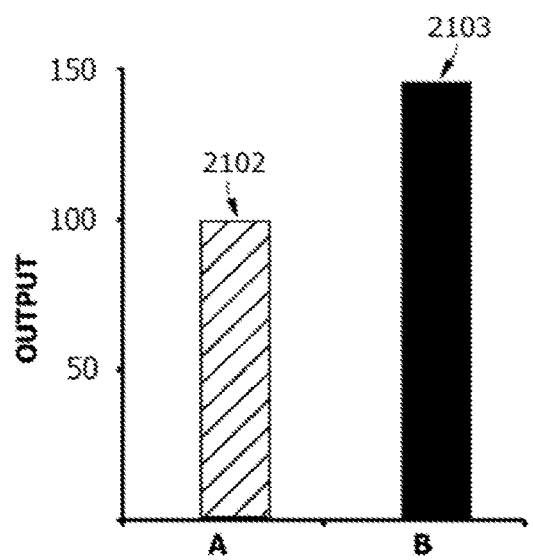
FIG. 32B graphs the integrated output signal strength with and without the back mirror. Output signal was found to be optimized by focusing the excitation beam at a focal point behind the mirror as shown in FIG. 29A and collecting emissions at a shorter working distance as shown in FIG. 29B.

FIG. 32B is a bar graph showing the output signal strength with (2103) and without (2102) the back mirror. Output signal was found to be optimized by focusing the excitation beam at a focal point behind the mirror as shown in FIG. 29A and collecting emissions at a shorter working distance as shown in FIGS. 29B and 30.

In a second experiment, the detection chamber is filled with a liquid sample containing a soluble fluorophore and pumped through the chamber at constant rate to avoid quenching artifact. The detector head height is then varied as before and the optimal detector height determined. In related experiments, the working distance of the light source from the source lens is also varied in order to optimize sensitivity and limit of detection. We learn that optimal configuration is not achieved when the objective lens is centered in the detection chamber and the other lenses are made confocal. When a mirror is used, decoupled optics achieves advantageous results, a technological advance in the field.

Figure 33A:
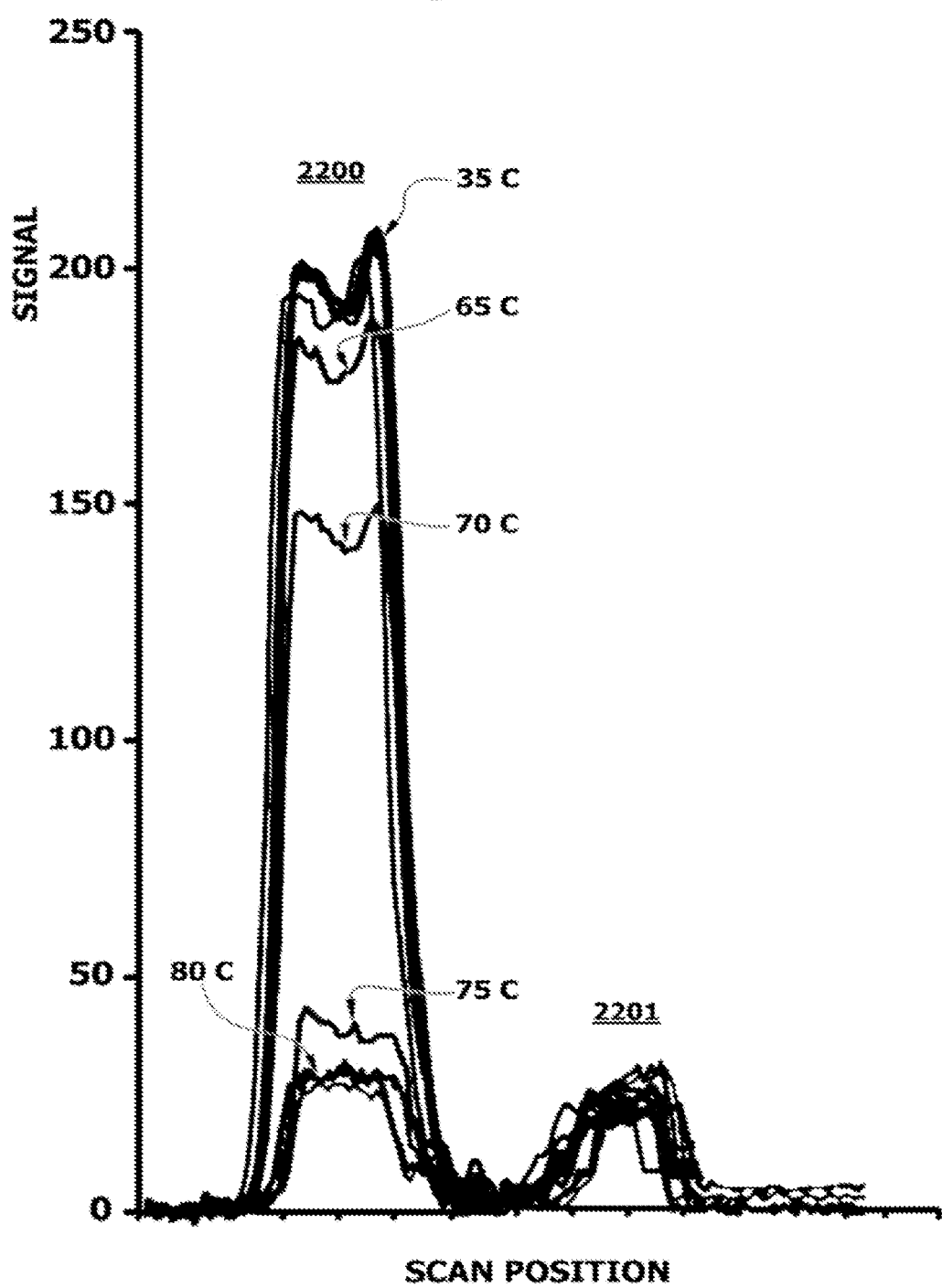
FIG. 33A demonstrates nested thermal melt curve data for a positive assay result and control, showing fluorescence resulting from a molecular beacon hybridized to an amplicons as a function of temperature.
Figure 33B:
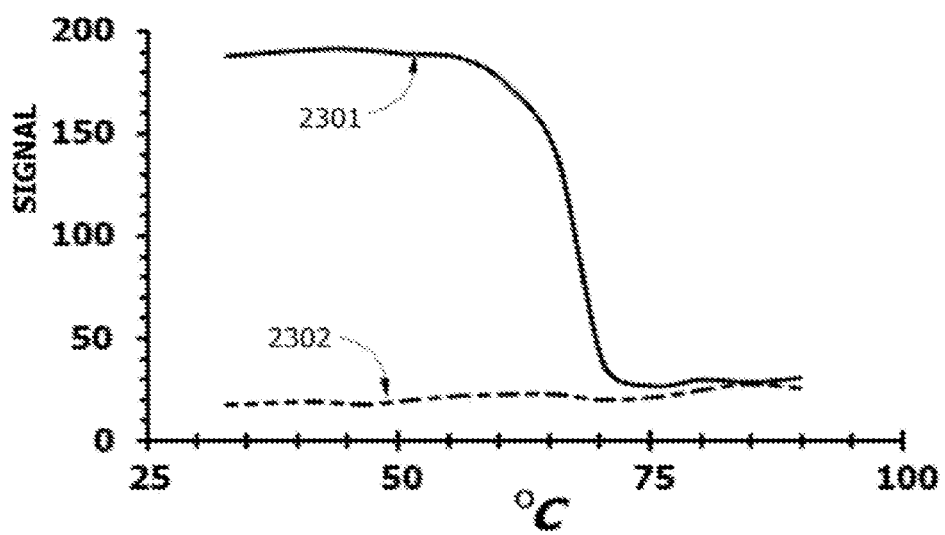
FIGS. 33B and 33C analyze the thermal melt profile, calculating a first derivative indicative of the $T_m$.
Figure 33C:
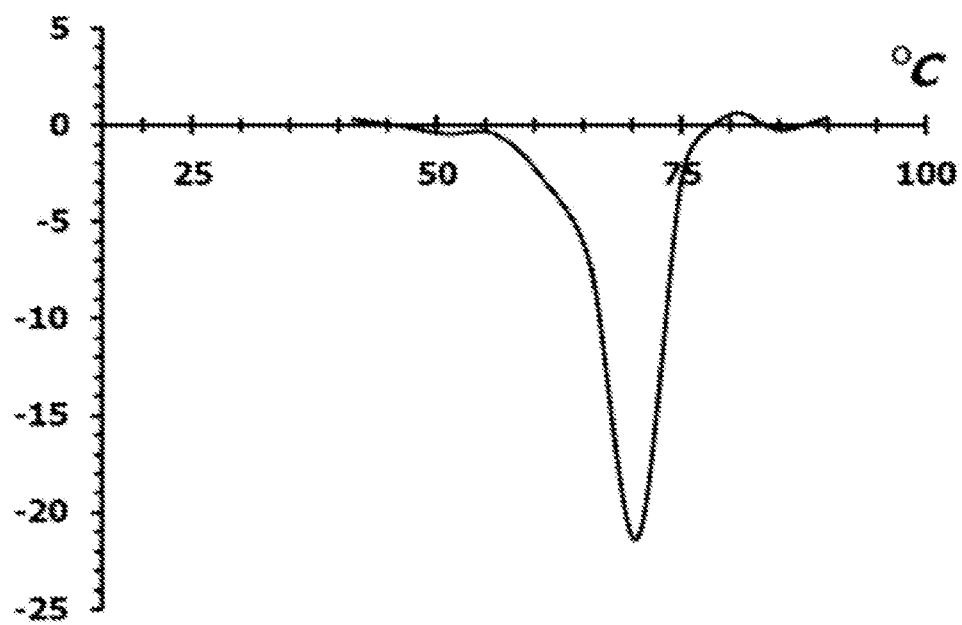

FIG. 33A shows scanning data collected for a molecular beacon hybridized to an amplicon. The scanning axis transects detection wells (2200, 2201) representing positive and negative test conditions respectively, and it can be seen that signal is limited to the detection wells. The sample is scanned repetitively as the temperature in the detection or sample chamber is systematically varied. The scans are overlaid in the plot to illustrate the spatial resolution of the data. Fluorescence scans for 35° C., 65° C., 70° C., 75° C. and 80° C. test conditions are marked. Test plots at 40, 45, 50, 55, and 60° C., and the 85 and 90° C. plots were not well differentiated, as expected, and are not individually marked. It can be seen that fluorescent signal is a function of temperature. Fluorescence quenching is observed to increase as the double stranded probe-target is melted, i.e., signal is greatest at 35° C. and is essentially not present at 80° C. In FIG. 33B, the data is plotted for signal versus temperature for the positive (2301, solid line) and negative (2302, dashed line) test conditions. In FIG. 33C, a first derivative is plotted, indicating a FRET melt temperature of about 70° C.

Example I

In this example, the apparatus of the invention is shown to be useful in diagnosis of infectious disease by detection of the nucleic acids of a pathogen in a human sample such as blood. Using on-board dry and liquid reagents, a blood sample is processed and DNA associated with Plasmodium falciparum is detected in about 30 minutes or less. DNA purified from the sample is subjected to PCR using two chambers with dual temperature zones as described in U.S. Pat. Nos. 7,544,506, 7,763,453, and 7,955,836, which are co-assigned. Amplicon is then detected using a FAM fluorescence-tagged molecular beacon directed at the amplified target. Optionally, a control consisting of a California Red-tagged RNAase P leukocyte exon sequence, with multiplex amplification, is used to validate the assay. A representative thermal melt curve obtained using the thermo-optical interface of the invention is shown in FIG. 33B.

Example II

The apparatus of the invention is useful in the diagnosis of coagulopathies. Using on-board dry and liquid reagents, a blood sample is assayed for Coagulation Factor VIIa deficiency by incubating plasma with a fluorogenic substrate such as (D-Phe-Pro-Arg-ANSNH-cyclohexyl-2 HCl; F.W.=777.81, Haematologic Technologies, Essex Junction Vt.) where ANSN is fluorophore 6-amino-1-naphthalenesulfonamide, which lights up when the amide bond between the dye and the peptide is cleaved. Tissue Factor (TF) is obtained from Calbiochem (LaJolla Calif.) and incorporated into phosphatidylcholine or phosphatidylserine vesicles before use. TF is used in excess. A 100 uL substrate reaction mixture consisting of 20 mM Hepes buffer, pH 7.4, 0.15 M NaCl, with 5 nM TF and containing 20 uM EDTA is incubated with a plasma sample for 10 min to form the active enzyme complex. The ANSH substrate is then added. The rate of hydrolysis of substrate is linear over the normal range of Factor VIIa, and can be determined from a standard curve. Descriptions of assay development may be found in US Pat. Appl. Publ. No. 2009/0325203 and other experimental literature.

While the above is a description of certain embodiments of the present invention, it is possible to use various alternatives, modifications and equivalents. Therefore, the scope of the present invention should be determined not with reference to the above description but should, instead, be determined with reference to the appended claims, along with their full scope of equivalents. The appended claims are not to be interpreted as including means-plus-function limitations, unless such a limitation is explicitly recited in a given claim using the phrase "means for."

All of the U.S. patents, U.S. patent application publications, U.S. patent applications, foreign patents, foreign patent applications and non-patent publications referred to in this specification and/or cited in an accompanying application data sheet, including but not limited to U.S. Patent Application No. 61/745,329, are incorporated herein by reference, in their entirety. Aspects of the embodiments can be modified, if necessary to employ concepts of the various patents, applications and publications to provide yet further embodiments.

What is claimed is:

1. A host instrument for removably receiving a microassay cartridge, said instrument comprising:
    a supporting baseplate;
    a docking bay for receiving-if the microassay cartridge, wherein said docking bay is mounted on said baseplate;
    a pneumatic control manifold disposed within said baseplate, said manifold having disposed thereon a pneumatic interface port array within said docking bay;
    attached to said baseplate within said docking bay, a heater assembly comprising at least one heating member with spring mount and with superior surface dimensioned for interfacing with an undersurface of said cartridge;
    a first fan for convectively dissipating heat from a cooling member disposed on said heating member;
    a second fan for convectively cooling a sample well disposed in a nose of the microassay cartridge wherein the second fan includes a blower mounted on an external wall of an instrument chassis of the host instrument; and
    a baffled duct connected to the second fan and directed onto the nose of the microassay cartridge;
    wherein said docking bay comprises a clamping mechanism configured to reposition the cartridge within the docking bay from first position above the pneumatic interface port array to a second position wherein said cartridge is operatively engaged with said pneumatic interface port array, and further wherein said spring mount is configured to press an undersurface of the microfluidic cartridge in said second position against said superior surface of said heating member.

2. The host instrument of claim 1, wherein said spring mount exerts a spring force of about 1 psi over a heat transfer surface reversibly contacting said cartridge and said heating member.

3. The host instrument of claim 1, wherein said docking bay with clamping mechanism is configured to simultaneously engage the pneumatic interface port array of the baseplate with mating ports of the microassay cartridge and to press the cartridge against the at least one spring-mounted heating member.

4. The host instrument of claim 1, wherein said host instrument is configured for pneumatically controlling the operations of the microassay cartridge via said pneumatic control manifold while clamped in said docking bay against the heating member.

5. The host instrument of claim 1, wherein said clamping mechanism is configured for disengaging said cartridge from said pneumatic interface port array and said heating mechanism of said baseplate so that said cartridge may be removed from said docking bay.

6. The host instrument of claim 5, wherein said cartridge comprises a single-use gasket configured to sealingly join said cartridge to said pneumatic interface port array of said docking bay.

7. The host instrument of claim 1, wherein said heating member is electropolished and chrome plated.

8. The host instrument of claim 1, wherein said heating member is resistively heated.

9. The host instrument of claim 1, wherein said second fan is configured for performing a thermal annealing function by cooling said sample well while the sample is fluorescently monitored.

* * * * *

UNITED STATES PATENT AND TRADEMARK OFFICE
CERTIFICATE OF CORRECTION

PATENT NO. : 10,436,713 B2  Page 1 of 1
APPLICATION NO. : 15/804869
DATED : October 8, 2019
INVENTOR(S) : C. Frederick Battrell et al.

It is certified that error appears in the above-identified patent and that said Letters Patent is hereby corrected as shown below:

Claim 1, Column 44, Line 20:
"receiving-if the microassay" should read: --receiving the microassay--.

Claim 1, Column 44, Line 33:
"microassay cartridge wherein" should read: --microassay cartridge, wherein--.

Signed and Sealed this
Twenty-sixth Day of January, 2021

Drew Hirshfeld
*Performing the Functions and Duties of the*
*Under Secretary of Commerce for Intellectual Property and*
*Director of the United States Patent and Trademark Office*